(12) United States Patent
Cosford et al.

(10) Patent No.: US 7,569,592 B2
(45) Date of Patent: Aug. 4, 2009

(54) HETEROARYL SUBSTITUTED PYRAZOLE MODULATORS OF METABOTROPIC GLUTAMATE RECEPTOR-5

(75) Inventors: Nicholas D. P. Cosford, San Diego, CA (US); Chixu Chen, San Diego, CA (US); Brian W. Eastman, San Diego, CA (US); Dehua Huang, San Diego, CA (US); Benito Munoz, San Diego, CA (US); Petpiboon Prasit, San Diego, CA (US); Nicholas D. Smith, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 874 days.

(21) Appl. No.: 10/497,122

(22) PCT Filed: Dec. 13, 2002

(86) PCT No.: PCT/US02/40147

§ 371 (c)(1),
(2), (4) Date: May 26, 2004

(87) PCT Pub. No.: WO03/051833

PCT Pub. Date: Jun. 26, 2003

(65) Prior Publication Data

US 2005/0026963 A1 Feb. 3, 2005

Related U.S. Application Data

(60) Provisional application No. 60/341,382, filed on Dec. 18, 2001.

(51) Int. Cl.
*A61K 31/4439* (2006.01)
*A61K 31/4155* (2006.01)
*C07D 401/04* (2006.01)

(52) U.S. Cl. .................... 514/341; 514/406; 546/275.4; 548/364.1

(58) Field of Classification Search ................. 514/341, 514/406; 546/275.4; 548/364.1
See application file for complete search history.

(56) References Cited

U.S. PATENT DOCUMENTS

| 2,833,779 | A * | 5/1958 | Fields et al. ............. 546/275.4 |
|---|---|---|---|
| 6,660,753 | B2 | 12/2003 | Van Wagenen et al. |
| 7,087,601 | B2 | 8/2006 | Arruda et al. |
| 7,105,548 | B2 | 9/2006 | Cosford et al. |
| 7,112,595 | B2 | 9/2006 | Wagenen et al. |
| 7,253,190 | B2 | 8/2007 | Cosford et al. |
| 7,268,151 | B2 | 9/2007 | Cosford et al. |
| 2005/0085514 | A1 | 4/2005 | Cosford et al. |
| 2005/0153986 | A1 | 7/2005 | Chen et al. |
| 2006/0189661 | A1 | 8/2006 | Wagenen et al. |
| 2006/0193926 | A1 | 8/2006 | Cosford et al. |
| 2006/0194807 | A1 | 8/2006 | Cosford et al. |
| 2006/0217420 | A1 | 9/2006 | Cosford et al. |
| 2007/0027321 | A1 | 2/2007 | Kamenecka et al. |
| 2007/0149547 | A1 | 6/2007 | Bonnefous et al. |

OTHER PUBLICATIONS

Passarotti et al. "Antiinflammatory activity of some 4-substituted-5-amminopyrazole derivatives" Currents in Toxicology and Therapy, 1993, vol. 1, No. 2, pp. 89-93.*

M. A. Halcrow et al., "Syntheses, Structures and Electrochemistry of [CuL1(Lr)]BF4[LI=3- {2,3-Dimethoxyphenyl)-1-(2-pyridyl)Pyrazole; Lr=tris(3-arylpyrazolyl)-hydroborate] and [CuL1 2][BF4]2. Effects of graphitic Interactions on the Stability of an Aryl Radical Cation", J. Chem. Soc., Dalton Trans, 1997, vol. 21, pp. 4025-4035.

G. I. Denis et al., "Synthesis and Some Transformations of N-)Beta-Acylethyl) Aminopyridines and N-(Beta-Acylethyl) Aminoquinolines", Zhurnal Organicheskol Khimii, 1977, vol. 13, No. 1, pp. 199-204, Translated in V. Kapsukas Vil'nyus State University.

Database Caplus, Accession No. 1964:45681, Kost et al., Reactions of Hydrazine Derivatives. Zh. Obshch. Khim. 1963, vol. 33, No. 11, 3603-3613 (English abstract).

* cited by examiner

*Primary Examiner*—Rei-Tsang Shiao
*Assistant Examiner*—Joseph R Kosack
(74) *Attorney, Agent, or Firm*—J. Eric Thies; William Krovatin

(57) ABSTRACT

Pyrazole compounds substituted directly, or by a bridge, with a heteroaryl moiety containing N adjacent to the point of connection of the heteroaryl, are mGluR5 modulators useful in the treatment of psychiatric and mood disorders such as, for example, schizophrenia, anxiety, depression, bipolar disorder and panic, as well as in the treatment of pain, circadian rhythm disorders, and other diseases.

2 Claims, No Drawings

HETEROARYL SUBSTITUTED PYRAZOLE MODULATORS OF METABOTROPIC GLUTAMATE RECEPTOR-5

RELATED APPLICATION DATA

This is a National filing under 35 USC 371 of PCT/US02/40147, filed Dec. 13, 2002, which claims priority from U.S. Ser. No. 60/341,382, filed Dec. 18, 2001.

BACKGROUND OF THE INVENTION

Field of the Invention

The present invention is directed to pyrazole compounds substituted with a heteroaryl moiety. In particular, this invention is directed to pyrazole compounds substituted directly, or by a bridge, with a heteroaryl moiety containing N adjacent to the point of connection of the heteroaryl which are metabotropic glutamate receptor—subtype 5 ("mGluR5") modulators useful in the treatment of psychiatric and mood disorders such as, for example, schizophrenia, anxiety, depression, panic, bipolar disorder, and circadian rhythm disorders, as well as in the treatment of pain, Parkinson's disease, cognitive dysfunction, epilepsy, drug addiction, drug abuse, drug withdrawal and other diseases.

RELATED BACKGROUND

A major excitatory neurotransmitter in the mammalian nervous system is the glutamate molecule, which binds to neurons, thereby activating cell surface receptors. Such surface receptors are characterized as either ionotropic or metabotropic glutamate receptors. The metabotropic glutamate receptors ("mGluR") are G protein-coupled receptors that activate intracellular second messenger systems when bound to glutamate. Activation of mGluR results in a variety of cellular responses. In particular, mGluR1 and mGluR5 activate phospholipase C, which is followed by mobilizing intracellular calcium.

Modulation of metabotropic glutamate receptor subtype 5 (mGluR5) is useful in the treatment of diseases that affect the nervous system (see for example W. P. J. M Spooren et al., *Trendy Pharmacol. Sci.*, 22:331-337 (2001) and references cited therein). For example, recent evidence demonstrates the involvement of mGluR5 in nociceptive processes and that modulation of mGluR5 using mGluR5-selective compounds is useful in the treatment of various pain states, including acute, persistent and chronic pain [K Walker et al., *Neuropharmacology*, 40:1-9 (2001); F. Bordi, A. Ugolini. *Brain Res.*, 871:223-233 (2001)], inflammatory pain [K Walker et al., *Neuropharmacology*, 40:10-19 (2001); Bhave et al. *Nature Neurosci.* 4:417-423 (2001)] and neuropathic pain [Dogrul et al. *Neurosci. Lett.* 292:115-118 (2000)].

Further evidence supports the use of modulators of mGluR5 in the treatment of psychiatric and neurological disorders. For example, mGluR5-selective compounds such as 2-methyl-6-(phenylethynyl)-pyridine ("MPEP") are effective in animal models of mood disorders, including anxiety and depression [W. P. J. M Spooren et al., *J. Pharmacol. Exp. Ther.*, 295:1267-1275 (2000); E. Tatarczynska et al, *Brit. J. Pharmacol.*, 132:1423-1430 (2001); A. Klodzynska et al, *Pol. J. Pharmacol.*, 132:1423-1430 (2001)]. Gene expression data from humans indicate that modulation of mGluR5 may be useful for the treatment of schizophrenia [T. Ohnuma et al, *Mol. Brain. Res.*, 56:207-217 (1998); ibid, *Mol. Brain. Res.*, 85:24-31 (2000)]. Studies have also shown a role for mGluR5, and the potential utility of mGluR5-modulatory compounds, in the treatment of movement disorders such as Parkinson's disease [W. P. J. M Spooren et al., *Europ. J. Pharmacol.* 406:403-410 (2000); H. Awad et al., *J. Neurosci.* 20:7871-7879 (2000); K. Ossawa et al. *Neuropharmacol.* 41:413-420 (2001)]. Other research supports a role for mGluR5 modulation in the treatment of cognitive dysfunction [G. Riedel et al, *Neuropharmacol.* 39:1943-1951 (2000)], epilepsy [A. Chapman et al, *Neuropharmacol.* 39:1567-1574 (2000)] and neuroprotection [V. Bruno et al, *Neuropharmacol.* 39:2223-2230 (2000)]. Studies with mGluR5 knockout mice and MPEP also suggest that modulation of these receptors may be useful in the treatment of drug addiction, drug abuse and drug withdrawal [C. Chiamulera et al. *Nature Neurosci.* 4:873-874 (2001)].

International Patent Publication WO 01/12627 and WO 99/26927 describe heteropolycyclic compounds and their use as metabotropic glutamate receptor antagonists.

M. A. Halcrow et al., *J. Chem. Soc., Dalton Trans.*, 21:4025-4036 (1997) describes the synthesis of 3-(2,5-dimethoxyphenyl)-1-(2-pyridyl)pyrazole. G. Denys et al., *Kapsukasa, Zh. Org. Khim.*, 13(1):199-204 (1977) describes the conversion of 1-(2-pyridyl)-3-pyrazolines to 1-(2-pyridyl)-3-pyrazoles.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, and U.S. Pat. No. 5,736,297 describes ring systems useful as a photosensitive composition.

However, there remains a need for novel compounds and compositions that therapeutically inhibit mGluR5 with minimal side effects.

SUMMARY OF THE INVENTION

The present invention is directed to novel pyrazole compounds substituted directly, or by a bridge, with a heteroaryl moiety containing N adjacent to the point of connection of the heteroaryl, are mGluR5 modulators useful in the treatment of psychiatric and mood disorders such as, for example, schizophrenia, anxiety, depression, panic, bipolar disorder, and circadian rhythm and sleep disorders—such as shift-work induced sleep disorder or jet-lag, as well as in the treatment of pain, Parkinson's disease, cognitive dysfunction, epilepsy, drug addiction, drug abuse, drug withdrawal and other diseases. This invention also provides a pharmaceutical composition which includes an effective amount of the novel pyrazole compounds substituted with a heteroaryl moiety, and a pharmaceutically acceptable carrier.

This invention further provides a method of treatment of psychiatric and mood disorders such as, for example, schizophrenia, anxiety, depression, panic, bipolar disorder, and circadian rhythm and sleep disorders—such as shift-work induced sleep disorder or jet-lag, as well as a method of treatment of pain, Parkinson's disease, cognitive dysfunction, epilepsy, drug addiction, drug abuse and drug withdrawal by the administration of an effective amount of the novel pyrazole compounds substituted with a heteroaryl moiety.

DETAILED DESCRIPTION OF THE INVENTION

A compound of this invention is represented by Formula (I):

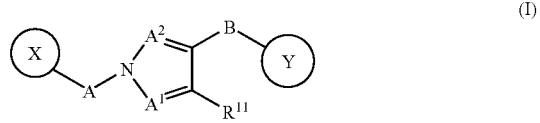

or a pharmaceutically acceptable salt thereof, wherein

X and Y each independently is aryl or heteroaryl wherein at least one of X and Y is a heteroaryl with N adjacent to the position of attachment to A or B respectively;

X is optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$-CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In one aspect, the compound of this invention is represented by Formula (I) or a pharmaceutically acceptable salt thereof, wherein X is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl) —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

one of A$^1$ and A$^2$ is N, the other is CR$^{12}$;

R$^{11}$ and R$^{12}$ is each independently halogen, —C$_{0-6}$alkyl, —C$_{0-6}$alkoxyl, or —N(C$_{0-4}$alkyl)(C$_{0-4}$alkyl), wherein optionally R$^{11}$ and R$^{12}$ are combined to form a cycloalkyl, heterocycloalkyl, aryl or heteroaryl ring fused to the pyrazole moiety; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups; and wherein optionally R$^{11}$ and R$^{12}$ each independently forms =O, =N(C$_{0-4}$alkyl) using a bond from the adjoining double bond;

any N may be an N-oxide;

wherein any of the alkyl optionally is substituted with 1-9 independent halogens;

and provided that when X=2-pyridyl, A$^1$=N, A$^2$=CH, R$^{11}$=R$^{12}$=H and A=B=C$_0$alkyl, then Y is not 4-methoxyphenyl or 2,5-dimethoxyphenyl.

In an embodiment of this one aspect, the compound of this invention is represented by Formula (I) or a pharmaceutically acceptable salt thereof, wherein X is 2-pyridyl optionally substituted with 1-4 independent halogen, —CN, NO$_2$, —C$_{1-6}$alkyl, —C$_{1-6}$alkenyl, —C$_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl) —N(C$_{0-6}$alkyl)(C$_{3-7}$cycloalkyl), or —N(C$_{0-6}$alkyl)(aryl) groups;

R$^1$, R$^2$, and R$^3$ each independently is —C$_{0-6}$alkyl, —C$_{3-7}$cycloalkyl, heteroaryl or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^4$ is —C$_{1-6}$alkyl, —C$_{3-7}$cycloalkyl, heteroaryl or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

A is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^9$CO—C$_{0-2}$alkyl-, —C$_{0-2}$alkyl-NR$^9$SO$_2$—C$_{0-2}$alkyl- or heteroC$_{0-4}$alkyl;

Y is phenyl optionally substituted with 1-5 independent halogen, —CN, NO$_2$, —C$_{1-6}$alkyl, —C$_{1-6}$alkenyl, —C$_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) groups;

R$^5$, R$^6$, and R$^7$ each independently is —C$_{0-6}$alkyl, —C$_{3-7}$cycloalkyl, heteroaryl or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

R$^8$ is —C$_{1-6}$alkyl, —C$_{3-7}$cycloalkyl, heteroaryl or aryl; optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

B is —C$_{0-4}$alkyl, —C$_{0-2}$alkyl-SO—C$_{0-2}$alkyl-, —C$_{0-2}$alkyl-SO$_2$—C$_{0-2}$alkyl-, —C$_{0-2}$alkyl-CO—C$_{0-2}$alkyl-, —C$_{0-2}$alkyl-NR$^{10}$CO—C$_{0-2}$alkyl-, —C$_{0-2}$alkyl-NR$^{10}$SO$_2$—C$_{0-2}$alkyl- or -heteroC$_{0-4}$alkyl;

R$^9$ and R$^{10}$ each independently is —C$_{0-6}$alkyl, —C$_{3-7}$cycloalkyl, heteroaryl or aryl; any of which is optionally substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N(C$_{0-6}$alkyl)(C$_{0-6}$alkyl), —N(C$_{0-6}$alkyl)(C$_{3-7}$cycloalkyl), —N(C$_{0-6}$alkyl)(aryl) substituents;

one of A$^1$ and A$^2$ is N, the other is CR$^{12}$;

R$^{11}$ and R$^{12}$ is each independently halogen, —C$_{0-6}$alkyl, —C$_{0-6}$alkoxyl, or —N(C$_{0-4}$alkyl)(C$_{0-4}$alkyl), wherein optionally R$^{11}$ and R$^{12}$ are combined to form a cycloalkyl, heterocycloalkyl, aryl or heteroaryl ring fused to the pyrazole moiety; wherein the —C$_{1-6}$alkyl substituent, cycloalkyl ring, or heterocycloalkyl ring each optionally is further substituted with 1-5 independent halogen, —CN, —C$_{1-6}$alkyl, —O(C$_{0-6}$alkyl), —O(C$_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond; any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In a second aspect, the compound of this invention is represented by Formula (I) or a pharmaceutically acceptable salt thereof, wherein X is pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In a third aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9CO$—$C_{0-2}$alkyl-, —$C_{0-2}$alkyl-$NR^9SO_2$—$C_{0-2}$alkyl- or -hetero$C_{0-4}$alkyl;

Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}CO$—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —$N(C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups; and wherein optionally $R^{11}$ and $R^{12}$ each independently forms =O, =$N(C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In an embodiment of the third aspect, the compound of this invention is represented by Formula (I) or a pharmaceutically acceptable salt thereof, wherein X is pyridyl optionally substituted with 1-4 independent halogen, —CN, $NO_2$, —$C_{1-6}$alkyl, —$C_{1-6}$alkenyl, —$C_{1-6}$alkynyl, —$OR^1$, —$NR^1R^2$, —$C(=NR^1)NR^2R^3$, —$N(=NR^1)NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —$C(=NR^1)R^2$, or —$C(=NOR^1)R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9CO$—$C_{0-2}$alkyl-, —$C_{0-2}$alkyl-$NR^9SO_2$—$C_{0-2}$alkyl- or -hetero$C_{0-4}$alkyl;

Y is 2-pyridyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —$C(=NR^5)NR^6R^7$, —$N(=NR^5)NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —$C(=NR^5)R^6$, or —$C(=NOR^5)R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), or —$N(C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}CO$-$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —$O(C_{0-6}$alkyl), —$O(C_{3-7}$cycloalkyl), —O(aryl), —O(heteroaryl), —$N(C_{0-6}$alkyl)($C_{0-6}$alkyl), —$N(C_{0-6}$alkyl)($C_{3-7}$cycloalkyl), —$N(C_{0-6}$alkyl)(aryl) substituents;

one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —$N(C_{0-4}$alkyl$)(C_{0-4}$alkyl$)$, wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In a fourth aspect, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In an embodiment of this fourth aspect, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

13

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -heteroC$_{0-4}$alkyl;

Y is 2-pyridyl optionally substituted with 1-4 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the $C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -heteroC$_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of A$^1$ and A$^2$ is N, the other is CR$^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, A$^1$=N, A$^2$=CH, $R^{11}$=$R^{12}$=H and A=B=C$_0$alkyl, then Y is not 4-methoxyphenyl or 2,5-dimethoxyphenyl.

14

In a fifth aspect, the compound of this invention is represented by Formula (I) or a pharmaceutically acceptable salt thereof, wherein X is aryl or heteroaryl optionally substituted with 1-7 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, NR$^1$CO$_2$R$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, $C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -heteroC$_{0-4}$alkyl;

Y is pyrazinyl optionally substituted with 1-3 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$ —C(=NR$^5$)R$^6$, or —C(=NOR$^5$)R$^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -heteroC$_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In an embodiment of this fifth aspect, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is pyrazinyl optionally substituted with 1-3 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In a sixth aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)$C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is benzoxazolyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In an embodiment of the sixth aspect of the invention, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent-halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is benzoxazolyl optionally substituted with 1-4 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, $C_{3-7}$cycloalkyl, heteroaryl or aryl; any of which is optionally substituted with 1-5 independent halogen, —CN, —$C_{1-6}$alkyl, —($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is CR$^{12}$;

$R^{13}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In a seventh aspect, the compound of this invention is represented by Formula (I) or a pharmaceutically acceptable salt thereof, wherein X is aryl or heteroaryl optionally substituted with 1-7 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -hetero$C_{0-4}$alkyl;

Y is 1,3-thiazolyl optionally substituted with 1-2 independent halogen, —CN, NO$_2$, —$C_{1-6}$alkyl, —$C_{1-6}$alkenyl, —$C_{1-6}$alkynyl, —OR$^5$, —NR$^5$R$^6$, —C(=NR$^5$)NR$^6$R$^7$, —N(=NR$^5$)NR$^6$R$^7$, —NR$^5$COR$^6$, —NR$^5$CO$_2$R$^6$, —NR$^5$SO$_2$R$^8$, —NR$^5$CONR$^6$R$^7$, —SR$^8$, —SOR$^8$, —SO$_2$R$^8$, —SO$_2$NR$^5$R$^6$, —COR$^5$, —CO$_2$R$^5$, —CONR$^5$R$^6$, —C(=NR$^5$)R$^6$, or —C(=NOR$^5$)R$^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)(($C_{0-6}$alkyl), —N($C_{0-6}$alkyl)(($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is CR$^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring; or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an embodiment of the seventh aspect of the invention, the compound of this invention is represented by Formula (I) or a pharmaceutically acceptable salt thereof, wherein X is phenyl optionally substituted with 1-5 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is 1,3-thiazolyl optionally substituted with 1-2 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O ($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an eighth aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is quinolinyl optionally substituted with 1-6 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In a ninth aspect, the compound of this invention is represented by Formula (I) or a pharmaceutically acceptable salt thereof, wherein X is naphthyl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9SO_2$—$C_{0-2}$alkyl- or -hetero$C_{0-4}$alkyl;

Y is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups;

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide;

wherein any of the alkyl optionally is substituted with 1-9 independent halogens;

and provided that when X=2-pyridyl, $A^1$=N, $A^2$=CH, $R^{11}$=$R^{12}$=H and A=B=$C_0$alkyl, then Y is not 4-methoxyphenyl or 2,5-dimethoxyphenyl.

In a tenth aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is pyrazolyl optionally substituted with 1-3 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO-$C_{0-2}$alkyl-, —$C_{0-2}$alkyl—$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an embodiment of the tenth aspect of the invention, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is pyrazolyl optionally substituted with 1-3 independent halogen, —CN, $NO_2$, —$C_{1-6}$alkyl, —$C_{1-6}$alkenyl, —$C_{1-6}$alkynyl, —$OR^5$, —$NR^5R^6$, —C(=$NR^5$)$NR^6R^7$, —N(=$NR^5$)$NR^6R^7$, —$NR^5COR^6$, —$NR^5CO_2R^6$, —$NR^5SO_2R^8$, —$NR^5CONR^6R^7$, —$SR^8$, —$SOR^8$, —$SO_2R^8$, —$SO_2NR^5R^6$, —$COR^5$, —$CO_2R^5$, —$CONR^5R^6$, —C(=$NR^5$)$R^6$, or —C(=$NOR^5$)$R^6$ substituents, wherein optionally two substituents are combined to form a cycloalkyl or heterocycloalkyl ring fused to Y; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an eleventh aspect, the compound of this invention is represented by Formula (I) or a pharmaceutically acceptable salt thereof, wherein X is aryl or heteroaryl optionally substituted with 1-7 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is quinoxalinyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{11}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an embodiment of the eleventh aspect of the invention, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -heteroC$_{0-4}$alkyl;

Y is quinoxalinyl optionally substituted with 1-5 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^{10}$CO—$C_{0-2}$alkyl-, —$C_{0-2}$alkyl-NR$^{10}$SO$_2$—$C_{0-2}$alkyl- or -heteroC$_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is CR$^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an twelfth aspect, the compound of this invention is represented by Formula (I) or a pharmaceutically acceptable salt thereof, wherein X is aryl or heteroaryl optionally substituted with 1-7 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$, —SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$, and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)$C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-SO$_2$—$C_{0-2}$alkyl-, —$C_{0-2}$alkyl-CO—$C_{0-2}$alkyl-, —$C_{0-2}$alkyl-NR$^9$CO—$C_{0-2}$alkyl-, —$C_{0-2}$alkyl-NR$^9$SO$_2$—$C_{0-2}$alkyl- or -heteroC$_{0-4}$alkyl;

Y is pyrimidinyl optionally substituted with 1-3 independent halogen, —CN, NO$_2$, —$C_{1-6}$alkyl, —$C_{1-6}$alkenyl, —$C_{1-6}$alkynyl, —OR$^1$, —NR$^1$R$^2$, —C(=NR$^1$)NR$^2$R$^3$, —N(=NR$^1$)NR$^2$R$^3$, —NR$^1$COR$^2$, —NR$^1$CO$_2$R$^2$, —NR$^1$SO$_2$R$^4$, —NR$^1$CONR$^2$R$^3$—SR$^4$, —SOR$^4$, —SO$_2$R$^4$, —SO$_2$NR$^1$R$^2$, —COR$^1$, —CO$_2$R$^1$, —CONR$^1$R$^2$, —C(=NR$^1$)R$^2$, or —C(=NOR$^1$)R$^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;.

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-, —$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

In an embodiment of the twelfth aspect of the invention, the compound of this invention is represented by Formula (I) or a pharmaceutically acceptable salt thereof, wherein X is phenyl optionally substituted with 1-5 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups $R^1$, $R^2$ and $R^3$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^4$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

A is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^9$CO—$C_{0-2}$alkyl-, —$C_{0-2}$alkyl-$NR^9SO_2$—$C_{0-2}$alkyl- or -hetero$C_{0-4}$alkyl;

Y is pyrimidinyl optionally substituted with 1-3 independent halogen, —CN, $NO_2$, —$C_{1-6}$alkyl, —$C_{1-6}$alkenyl, —$C_{1-6}$alkynyl, —$OR^1$, —$NR^1R^2$, —C(=$NR^1$)$NR^2R^3$, —N(=$NR^1$)$NR^2R^3$, —$NR^1COR^2$, —$NR^1CO_2R^2$, —$NR^1SO_2R^4$, —$NR^1CONR^2R^3$, —$SR^4$, —$SOR^4$, —$SO_2R^4$, —$SO_2NR^1R^2$, —$COR^1$, —$CO_2R^1$, —$CONR^1R^2$, —C(=$NR^1$)$R^2$, or —C(=$NOR^1$)$R^2$ substituents, wherein optionally two substituents are combined to form a cycloalkyl or heterocycloalkyl ring fused to X; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups.

$R^5$, $R^6$, and $R^7$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents;

$R^8$ is —$C_{1-6}$alkyl, —$C_{3-7}$cycloalkyl, heteroaryl or aryl; optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)$C_{3-7}$cycloalkyl), —N($C_{0-6}$alkyl)(aryl) substituents;

B is —$C_{0-4}$alkyl, —$C_{0-2}$alkyl-SO—$C_{0-2}$alkyl-, —$C_{0-2}$alkyl-$SO_2$—$C_{0-2}$alkyl-, —$C_{0-2}$alkyl-CO—$C_{0-2}$alkyl-, —$C_{0-2}$alkyl-$NR^{10}$CO—$C_{0-2}$alkyl-, —$C_{0-2}$alkyl-$NR^{10}SO_2$—$C_{0-2}$alkyl- or -hetero$C_{0-4}$alkyl;

$R^9$ and $R^{10}$ each independently is —$C_{0-6}$alkyl, —$C_{3-7}$cycloalkyl, heteroaryl or aryl; any of which is optionally substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), —N($C_{0-6}$alkyl)(aryl) substituents; one of $A^1$ and $A^2$ is N, the other is $CR^{12}$;

$R^{11}$ and $R^{12}$ is each independently halogen, —$C_{0-6}$alkyl, —$C_{0-6}$alkoxyl, or —N($C_{0-4}$alkyl)($C_{0-4}$alkyl), wherein optionally $R^{11}$ and $R^{12}$ are combined to form a cycloalkyl, heterocycloalkyl, aryl or heteroaryl ring fused to the pyrazole moiety; wherein the —$C_{1-6}$alkyl substituent, cycloalkyl ring, or heterocycloalkyl ring each optionally is further substituted with 1-5 independent halogen, —CN, —$C_{1-6}$alkyl, —O($C_{0-6}$alkyl), —O($C_{3-7}$cycloalkyl), —O(aryl), —O(heteroaryl), —N($C_{0-6}$alkyl)($C_{0-6}$alkyl), —N($C_{0-6}$alkyl)($C_{3-7}$cycloalkyl), or —N($C_{0-6}$alkyl)(aryl) groups; and wherein optionally $R^{11}$ and $R^{12}$ each independently forms =O, =N($C_{0-4}$alkyl) using a bond from the adjoining double bond;

any N may be an N-oxide; and wherein any of the alkyl optionally is substituted with 1-9 independent halogens.

As used herein, "alkyl" as well as other groups having the prefix "alkyl" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiv) norepinephrine modulators, xv) L-DOPA, xvi) buspirone, xvii) lithium, xviii) valproate, ixx) neurontin (gabapentin), xx) olanzapine, xxi) nicotinic agonists or antagonists including nicotine, xxii) muscarinic agonists or antagonists, xxiii) heroin substituting drugs such as methadone, levo-alpha-acetylmethadol, buprenorphine and naltrexone, and xxiv) disulfiram and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, panic, bipolar disorder, and circadian rhythm and sleep disorders—such as shift-work induced sleep disorder or jet-lag, as well as being useful in the treatment of pain which are responsive to mGluR5 inhibition, or alternatively about 0.5 mg to about 7 g per patient per day. For example, schizophrenia, anxiety, depression, panic, bipolar disorder, and circadian rhythm and sleep disorders—such as shift-work induced sleep disorder or jet-lag, may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the mGluR5 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g.; oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as mGluR5 inhibitors. Accordingly, another aspect of the invention is the treatment in mammals of, for example, schizophrenia, anxiety, depression, panic, bipolar disorder, and circadian rhythm and sleep disorders—such as shift-work induced sleep disorder or jet-lag, pain, Parkinson's disease, cognitive dysfunction, epilepsy, drug addiction, drug abuse and drug withdrawal—maladies that are amenable to amelioration through inhibition of mGluR5—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the mGluR5 inhibiting compound of this invention can be advantageously used in combination with i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| dppf | 1,1'-bis(diphenylphosphino)-ferrocene |
| EDCI | 1-(3-dimethylaminopropyl)-3-ethylcarbodiimide hydrochloride |
| $Et_3N$ | triethylamine |
| GST | glutathione transferase |
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| Ms0 | methanesulfonate = mesylate |
| NBS | N-bromo succinimide |
| NSAID | non-steroidal anti-inflammatory drug |
| o-Tol | ortho-tolyl |
| OXONE ® | $2KHSO_5 \cdot KHSO_4 \cdot K_2SO_4$ |
| PCC | pyridinium chlorochromate |
| $Pd_2(dba)_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or $SO_2NH_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| $C_3H_5$ | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

The compounds of this invention were tested against the hmGluR5a receptor stably expressed in mouse fibroblast Ltk⁻ cells (the hmGluR5a/L38-20 cell line) and activity was detected by changes in $[Ca^{++}]_i$, measured using the fluorescent $Ca^{++}$-sensitive dye, fura-2. InsP assays were performed in mouse fibroblast Ltk⁻ cells (LM5a cell line) stably expressing hmGluR5a. The assays described in International Patent Publication WO 0116121 can be used.

Calcium Flux Assay

The activity of compounds was examined against the hmGluR5a receptor stably expressed in mouse fibroblast Ltk⁻ cells (the hmGluR5a/L38 cell line). See generally Daggett et al., *Neuropharmacology* 34:871-886 (1995). Receptor activity was detected by changes in intracellular calcium ($[Ca^{2+}]_i$) measured using the fluorescent calcium-sensitive dye, fura-2. The hmGluR5a/L38-20 cells were plated onto 96-well plates, and loaded with 3 μM fura-2 for 1 h. Unincorporated dye was washed from the cells, and the cell plate was transferred to a 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510 nm interference filter and directed into a cooled CCD camera (Princeton Instruments). Image pairs were captured approximately every 1 s, and ratio images were generated after background subtraction. After a basal reading of 20 s, an $EC_{80}$ concentration of glutamate (10 μM) was added to the well, and the response evaluated for another 60 s. The glutamate-evoked increase in $[Ca']_i$ in the presence of the screening compound was compared to the response of glutamate alone (the positive control).

Phosphatidylinositol Hydrolysis (PI) Assays

Inositolphosphate assays were performed as described by Berridge et al. [Berridge et al, *Biochem. J.* 206: 587-5950 (1982); and Nakajima et al., *J. Biol. Chem.* 267:2437-2442 (1992)] with slight modifications. Mouse fibroblast Ltk cells expressing hmGluR5 (hmGluR5/L38-20 cells) were seeded in 24-well plates at a density of 8×10⁵ cells/well. One μCi of [³H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 mL of standard Hepes buffered saline buffer (HBS; 125 mM NaCl, 5 mM KCl, 0.62 mM MgSO₄, 1.8 mM CaCl₂, 20 mM HEPES, 6 mM glucose, pH to 7.4). The cells were washed with HBS containing 10 mM LiCl, and 400 μL buffer added to each well. Cells were incubated at 37° C. for 20 min. For testing, 50 μL of 10× compounds used in the practice of the invention (made in HBS/LiCl (100 mM)) was added and incubated for 10 minutes. Cells were activated by the addition of 10 μM glutamate, and the plates left for 1 hour at 37° C. The incubations were terminated by the addition of 1 mL ice-cold methanol to each well. In order to isolate inositol phosphates (IPs), the cells were scraped from wells, and placed in numbered glass test tubes. One mL of chloroform was added to each tube, the tubes were mixed, and the phases separated by centrifugation. IPs were separated on Dowex anion exchange columns (AG 1-X8 100-200 mesh formate form). The upper aqueous layer (750 μL) was added to the Dowex columns, and the columns eluted with 3 mL of distilled water. The eluents were discarded, and the columns were washed with 10 mLs of 60 mM ammonium formate/5 mM Borax, which was also discarded as waste. Finally, the columns were eluted with 4 mL of 800 mM ammonium formate/0.1M formic acid, and the samples collected in scintillation vials. Scintillant was added to each vial, and the vials shaken, and counted in a scintillation counter after 2 hours. Phosphatidylinositol hydrolysis in cells treated with certain exemplary compounds was compared to phosphatidylinositol hydrolysis in cells treated with the agonist alone in the absence of compound.

The compounds of this application have mGluR5 inhibitory activity as shown by an $IC_{50}$ value of less than 10 μM and/or an inhibition of >30% at a concentration of 3 μM in the calcium flux assay and/or inhibition of >50% at a concentration of 100 μM in the PI assay. Preferably, the compounds should have $IC_{50}$ values of less than 1 μM in the calcium flux assay and $IC_{50}$ values of less than 10 μM in the PI assay. Even more preferably, the compounds should have $IC_{50}$ values of less than 100 nM in the calcium flux assay and $IC_{50}$ values of less than 1 μM in the PI assay.

Examples 1-92 have mGluR5 inhibitory activity as shown by an $IC_{50}$ value of less than 10 μM and/or an inhibition of >30% at 3 μM concentration in the calcium flux assay and/or inhibition of >50% at 100 μM concentration in the PI assay.

Examples 93-281 have mGluR5 inhibitory activity <30% at 3 μM concentration in the calcium flux assay and/or inhibition <50% at 100 μM concentration in the PI assay.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

In accordance with another embodiment of the present invention, there are provided methods for the preparation of heteroaryl-substituted pyrazole compounds as described above. For example, many of the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a heteoaryl-substituted pyrazole of Formula (I).

In Schemes 1 to 9 below, X and Y are as defined above; Other variables are understood by one in the art by the context in which they are used.

Scheme 1

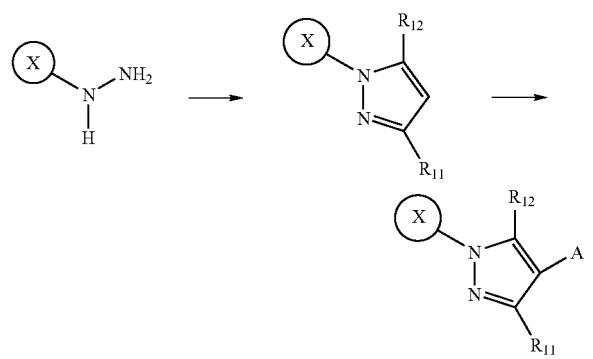

Thus in Scheme 1, ring system X containing a hydrazine moiety (prepared using synthetic chemistry techniques well known in the art) is reacted with a 1,3-dicarbonyl or its equivalent in a suitable solvent (e.g. EtOH, THF, DME, DMF etc.) at a temperature between about 30° C. to 150° C. for about 1 to 18 h to form a substituted pyrazole (see for example Sugiyarto, K. H.; Goodwin, H. A. *Aust.J.Chem*. 1988, 41, 1645-1664). In turn, the 4-position of the pyrazole is derivatized with a functional group A which is capable of undergoing a metal-catalyzed cross-coupling reaction such as a halogen or trifluoromethanesulfonate and the like. For example, the group A may be a bromide radical which maybe installed using molecular bromine under acidic conditions (see for example Khan, M. A.; Pinto, A. A. A. *J.Heterocycl.Chem*. 1981, 18, 9-14). In turn, the derivatized pyrazole is reacted with a moiety Y under metal-catalyzed cross-coupling conditions (Scheme 2)

Scheme 2

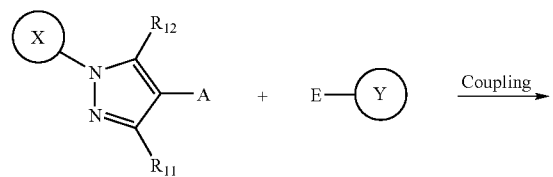

-continued

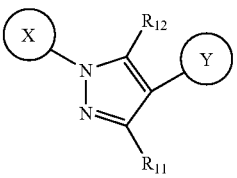

E is a metallic or metalloid species such as B(OR)$_2$, Li, MgHal, SnR$_3$, ZnHal, SiR$_3$ and the like which is capable of undergoing a metal-catalyzed cross-coupling reaction. The coupling may be promoted by a homogeneous catalyst such as Pd(PPh$_3$)$_4$, or by a heterogeneous catalyst such as Pd on carbon in a suitable solvent (e.g. THF, DME, toluene, MeCN, DMF, H$_2$O etc.). Typically a base, such as K$_2$CO$_3$, NEt$_3$, and the like, will also be present in the reaction mixture. Other promoters may also be used such as CsF. The coupling reaction is typically allowed to proceed by allowing the reaction temperature to warm slowly from about 0° C. up to ambient temperature over a period of several hours. The resulting reaction mixture is then maintained at ambient temperature, or heated to a temperature between about 30° C. to 150° C. The reaction mixture is then maintained at a suitable temperature for a time in the range of about 4 up to 48 hours, with about 18 hours typically being sufficient (see for example Miyaura, N.; Suzuki, A. *Chem. Rev*. 1995, 95, 2457-2483). The product from the reaction can be isolated and purified employing standard techniques, such as solvent extraction, chromatography, crystallization, distillation and the like. Another embodiment of the present invention is illustrated in Scheme 3 below.

Scheme 3

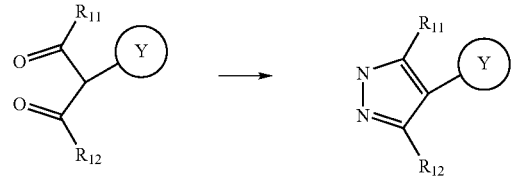

Thus a 1,3-dicarbonyl compound substituted at the 2 position with a moiety Y (prepared using synthetic chemistry techniques well known in the art), is condensed with hydrazine in a suitable solvent (e.g. EtOH, THF, DME, DMF etc.), at a temperature between about 30° C. to 150° C. for about 1 to 18 h to form a substituted pyrazole (see for example Brown, D. J.; Cowden, W. B.; Grigg, G. W.; Kavulak, D. *Aust.J.Chem.*, 1980, 33, 2291-2298).

Scheme 4

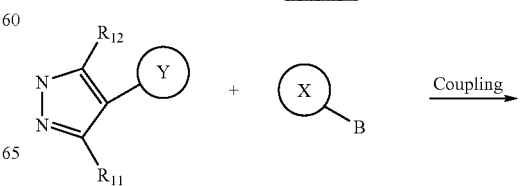

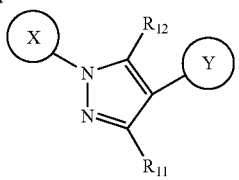

As shown in Scheme 4, the pyrazole may then be coupled with a species X substituted with a group B. B maybe a metalloid species such as $B(OR)_2$, BiLn and the like and the reaction maybe promoted with stoichiometric or catalytic amounts of metal salts such as $Cu(OAc)_2$, CuI or CuOTf and the like. Typically, a base (e.g. pyridine, $NEt_3$, $Cs_2CO_3$, $K_2CO_3$ etc.) will also be present and the reaction carried out in a suitable solvent (e.g. DCM, THF, DME toluene, MeCN, DMF, $H_2O$ etc.). Additionally, molecular sieves maybe used as a cocatalyst.

Alternatively, B may be a halogen or other functional group capable of undergoing a metal catalyzed N-arylation cross-coupling reaction. In that case, additional promoters such as 1,10-phenanthaline and dibenzylideneacetone may also be added to the reaction mixture. The cross-coupling reaction maybe carried out at ambient temperature or heated to a temperature anywhere between about 30° C. to 150° C. The resulting reaction mixture is then maintained at a suitable temperature for a time in the range of about 4 up to 72 hours, with 18 hours typically being sufficient (see for example Lam, P. Y. S.; Clark, C. G.; Saubern, S.; Adams, J.; Winters, M. P.; Cham, D. M. T.; Combs, A. *Tetrahedron Lett*. 1998, 39, 2941-2944 and Kiyomori, A.; Marcoux, J. F.; Buchwald, S. L. *Tetrahedron Lett*. 1999, 40, 2657-2660). The product from the reaction can be isolated and purified employing standard techniques, such as solvent extraction, chromatography, crystallization, distillation and the like.

In another embodiment of the present invention when B is a good aryl leaving group such as F, and X is electron deficient or has one or more electron withdrawing substituents (e.g. $NO_2$, CN), the coupling reaction may be effected thermally in a temperature range of about 60° C. up to about 250° C. Typically this reaction is carried out in the presence of base (e.g. pyridine, $NEt_3$, $Cs_2CO_3$, $K_2CO_3$ etc.) in a suitable solvent, such as DMSO, DMF, DMA $H_2O$ and the like, and takes from about 1 h up to about 72 h with 18 hours typically being sufficient (see for example Russell, S. S.; Jahangir; *Synth. Commun*. 1994, 24, 123-130). Another embodiment of the present invention is illustrated in Scheme 5.

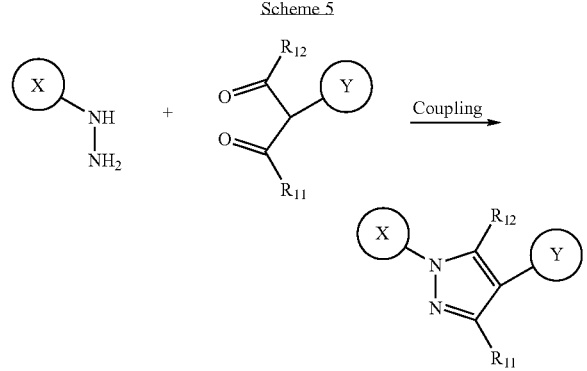

Scheme 5

Thus a 1,3-dicarbonyl compound substituted at the 2 position with a moiety Y (prepared using synthetic chemistry techniques well known in the art (see for example Fox, J. F.; Huang, X.; Chieffi, A.; Buchwald, S. L. *J. Am. Chem. Soc*. 2000, 122, 1360-1370) is condensed with a species X substituted with a hydrazine functional group in a suitable solvent (e.g. EtOH, THF, DME, DMF, $H_2O$ etc.) at a temperature between about 30° C. to 150° C. for about 1 to about 24 h to form a substituted pyrazole (see for example Pawar, R. A.; *Heterocycles*, 1984, 21, 568). Another embodiment of the present invention is illustrated in Scheme 6.

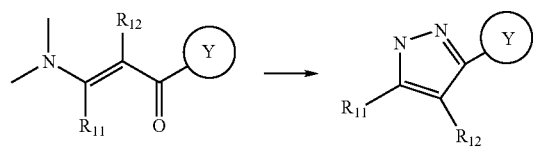

Scheme 6

Thus, a species Y substituted with a 3-dimethylamino-2,3-unsaturated ketone is prepared using synthetic chemistry techniques well known to those skilled in the art (see for example Kepe, V.; Kocevar, M.; Polanc, S. *J. Heterocyclic Chem*. 1996, 33, 1707-1710). The homologated amide species is heated with hydrazine in a suitable solvent (e.g. EtOH, THF, DME, DME, $H_2O$ etc.) at a temperature between about 30° C. to 150° C. for about 1 h up to about 24 h to form a pyrazole substituted with Y (see for example Wang, F.; Schwabacher, A. W. *Tetrahedron. Lett*. 1999, 40, 4779-4782).

As shown in Scheme 7, the pyrazole may then be coupled with a ring system X substituted with a functional group B.

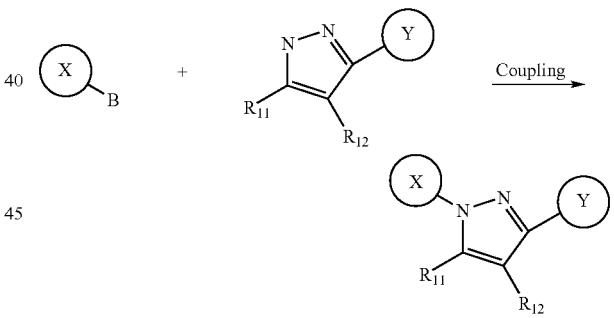

Scheme 7

B may be a metalloid species such as $B(OR)_2$, BiLn and the like and the reaction maybe promoted with stoichiometric or catalytic metal salts such as $Cu(OAc)_2$, CuI, or CuOTf and the like. Typically, a base (e.g. pyridine, $NEt_3$, $Cs_2CO_3$, $K_2CO_3$ etc.) will also be present and the reaction carried out in a suitable solvent (e.g. DCM, THF, DME, MeCN, DMF, $H_2O$ etc.). Additionally, molecular sieves maybe used as a cocatalyst. Alternatively B may be a halogen or other functional group capable of undergoing a metal catalyzed N-arylation cross-coupling reaction. In which case, additional promoters such as 1,10-phenanthrolene and dibenzylideneacetone may also be added to the reaction mixture. The cross-coupling reaction maybe carried out at ambient temperature or heated to a temperature between about 30° C. to 150° C. The reaction mixture is then maintained at a suitable temperature for a time in the range of about 4 up to 72 hours, with 18 hours typically being sufficient (see for example Lam, P. Y. S.; Clark, C. G.;

Saubern, S.; Adams, J.; Winters, M. P.; Cham, D. M. T.; Combs, A. *Tetrahedron Lett*. 1998, 39, 2941-2944 and Kiyomori, A.; Marcoux, J. F.; Buchwald, S. L. *Tetrahedron Lett*. 1999, 40, 2657-2660). The product from the reaction can be isolated and purified employing standard techniques, such as solvent extraction, chromatography, crystallization, distillation and the like.

In another embodiment of the present invention, when B is a good aryl leaving group such as F, and X is electron deficient or has one or more electron withdrawing substituents (e.g. $NO_2$, CN etc.), the coupling reaction may be effected thermally in a temperature range of about 60° C. up to about 250° C. Typically, this reaction is carried out in the presence of base (e.g. pyridine, $NEt_3$, $Cs_2CO_3$, $K_2CO_3$ etc.) in a suitable solvent, such as DMSO, DMF, DMA $H_2O$ and the like, and takes from about 1 h up to about 72 h with 18 hours typically being sufficient (see for example (see for example Russell, S. S.; Jahangir; *Synth.Commun*. 1994, 24, 123-130).

Another embodiment of the present invention is illustrated in Scheme 8.

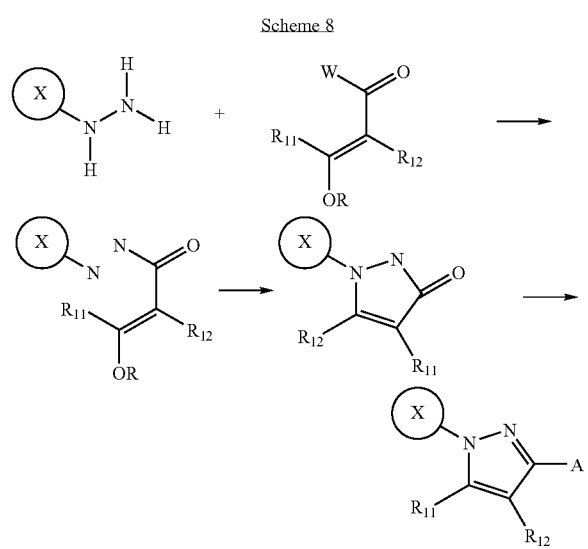

Thus, moiety X substituted with a hydrazine functional group (prepared using synthetic chemistry techniques well known in the art) is reacted with an activated acyl enol ether moiety in a suitable solvent (e.g. THF, DME, DMF, $Et_2O$ etc.) to form a pendant enol hydrazide. In Scheme 8, the leaving group W can be halogen, OR, SR etc. or if W=OH, the reaction is effected using typical peptide-coupling conditions (e.g using EDC etc.) that are well known to those skilled in the art at a temperature between about 0° C. to 100° C. for about 1 h to 18 h. Under acidic conditions, the pendant enol hydrazide cyclizes to form the corresponding pyrazolidone (see for example Shi, G.; Wang, Q.; Schlosser, M. *Tetrahedron* 1996, 52, 4403-4410). This is then converted to a pendant pyrazole substituted at the 3 position with a group A where A is a functional group capable of undergoing a metal-catalyzed cross-coupling reaction. For example, A may be trifluoromethanesulfonate, halogen, acyloxy, alkyl- or arylsulfonate, alkyl- or arylsulfinate, alkyl- or arylsulfide, phosphate, phosphinate and the like.

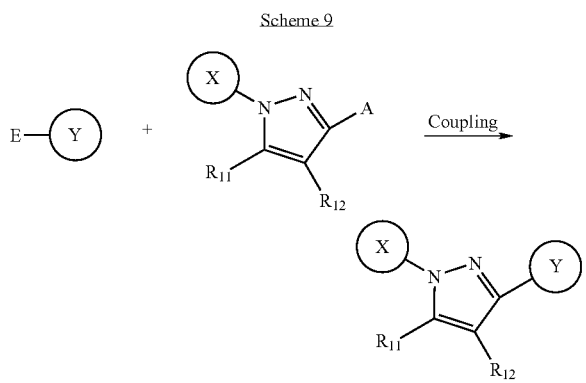

As shown in Scheme 9, the pyrazole from Scheme 8 can be coupled with a ring system Y substituted with a group E where E is a metallic or metalloid species such as $B(OR)_2$, Li, MgHal, $SnR_3$, $ZnHal_2$, $SiR_3$ and the like which is capable of undergoing a metal-catalyzed cross-coupling reaction. The coupling may be promoted by a homogeneous catalyst such as $Pd(PPh_3)_4$, or by a heterogeneous catalyst such as Pd on carbon in a suitable solvent, such as THF, DME, MeCN, DMF, $H_2O$ and the like. Typically, a base (e.g. $K_2CO_3$ $NEt_3$, etc.) will also be present in the reaction mixture. Other promoters may also be used such as CsF. The coupling reaction is typically allowed to proceed by allowing the reaction temperature to warm slowly from about 0° C. up to ambient temperature over a period of several hours. The reaction mixture is then maintained at ambient temperature, or heated to a temperature between about 30° C. to 150° C. The reaction mixture is then maintained at a suitable temperature for a time in the range of about 4 up to 48 hours, with about 18 hours typically being sufficient. The product from the reaction can be isolated and purified employing standard techniques, such as solvent extraction, chromatography, crystallization, distillation and the like (see for example Miyaura, N.; Suzuki, A. *Chem. Rev*. 1995, 95, 2457-2483).

In addition, many of the heterocyclic compounds described above can be prepared using other synthetic chemistry techniques well known in the art (see *Comprehensive Heterocyclic Chemistry*, Katritzky, A. R. and Rees, C. W. eds., Pergamon Press, Oxford, 1984) and references cited there within.

COMPOUND 1

Synthesis of 2-(1H-pyrazol-4-yl)pyridine 2-(2-Pyridyl)-malondialdehyde (7.8 g, 52 mmol) and hydrazine hydrate (3.7 mL) were heated at 75° C. in ethanol (75 mL) for 18 h. After cooling to ambient temperature and concentration in vacuo, recrystallization from EtOAc/Hexane gave 2-(1H-pyrazol-4-yl)pyridine as gold crystals. MP=136° C. $^1$H NMR ($CD_3Cl$, 300 MHz) δ 6.48-8.51 (1H, m), 8.30 (1H, br. s), 8.07 (1H, br. s), 7.74 (1H, ddd), 7.68 (1H, d), 7.15 (1H, ddd). MS (ESI) 146 (M+H)$^+$

EXAMPLE 1

Synthesis of 3-(4-pyridin-2-yl-1H-pyrazol-1-yl)benzonitrile

To 2-(1H-pyrazol-4-yl)pyridine (292 mg, 2 mmol), 3-cyanoboronic acid (590 mg, 4 mmol), $Cu(OAc)_2$ (547 mg, 3 mmol) and pyridine (0.32 mL, 4 mmol) in dichloromethane (4 mL) was added 0.5 g of 4 Å molecular sieves. The resulting reaction mixture was stirred at ambient temperature under atmospheric conditions for 48 h, whereupon it was filtered through Celite, washing with dichloromethane. The reaction mixture was concentrated onto silica gel in vacuo and purified by liquid chromatography on silica gel eluting with EtOAc:hexane (1:1 to 1:0) to afford a solid that was recrystallized from EtOH-H$_2$O to afford 3-(4-pyridin-2-yl-1H-pyrazol-1-yl)benzonitrile as a white solid. $^1$H NMR (CD$_3$Cl, 300 MHz) δ 8.63-8.64 (1H, m), 8.56 (1H, s), 8.23 (1H, s), 8.14 (1H, m), 8.00-8.05 (1H, m), 7.75 (1H, ddd), 7.57-7.66 (3H, m), 7.21 (1H, ddd). MS (ESI) 247 (M+H)$^+$

EXAMPLE 2

Synthesis of 2-[1-(3-fluorophenyl)-1H-pyrazol-4-yl]pyridine

To 2-(1H-pyrazol-4-yl)pyridine (292 mg, 2 mmol), 3-fluoroboronic acid (570 mg, 4 mmol), Cu(OAc)$_2$ (547 mg, 3 mmol) and pyridine (0.32 mL, 4 mmol) in dichloromethane (4 mL) was added 0.5 g of 4 Å molecular sieves. The resulting reaction mixture was stirred at ambient temperature under atmospheric conditions for 48 h, whereupon it was filtered through Celite, washing with dichloromethane. The reaction mixture was concentrated onto silica gel in vacuo and purified by liquid chromatography on silica gel eluting with EtOAc:hexane (1:9 to 1:1) to afford 2-[1-(3-fluorophenyl)-1H-pyrazol-4-yl]pyridine as a white solid. $^1$H NMR (CD$_3$Cl, 300 MHz) δ 8.62-8.63 (1H, m), 8.52 (1H, s), 8.20 (1H, s), 7.40 (1H, ddd), 7.55-7.59 (3H, m), 7.42-7.46 (1H, m), 7.19 (1H, ddd), 7.01-7.05 (1H, m). MS (ESI) 240 (M+H)$^+$

EXAMPLE 3

Synthesis of 2-[1-(1-naphthyl)-1H-pyrazol-4-yl]pyridine

To 2-(1H-pyrazol-4-yl)pyridine (292 mg, 2 mmol), 1-napthaleneboronic acid (690 mg, 4 mmol), Cu(OAc)$_2$ (547 mg, 3 mmol) and pyridine (0.32 mL, 4 mmol) in dichloromethane (4 mL) was added 0.5 g of 4 Å molecular sieves. The resulting reaction mixture was stirred at ambient temperature under atmospheric conditions for 48 h, whereupon it was filtered through Celite, washing with dichloromethane. The reaction mixture was concentrated on to silica gel in vacuo and purified by liquid chromatography onto silica gel eluting with EtOAc:hex (2:8 to 3:7) to afford 2-[1-(1-naphthyl)-1H-pyrazol-4-yl]pyridine as a white solid. $^1$H NMR (CD$_3$Cl, 300 MHz) δ 8.63-8.65 (1H, m), 8.39 (1H, s), 8.34 (1H, s), 7.94-7.99 (3H, m), 7.73 (1H, ddd), 7.53-7.64 (5H, m), 7.18 (1H, m). MS (ESI) 272 (M+H)$^+$

EXAMPLE 4

Synthesis of 2-(1-pyridin-3-yl-1H-pyrazol-4-yl)pyridine 2-(1H-Pyrazol-4-yl)pyridine (292 mg, 2 mmol), 3-bromopyridine (0.23 mL, 2.4 mmol), Cu(OTf)$_2$ (50 mg, 0.1 mmol), dibenzylideneacetone (24 mg, 0.1 mmol), Cs$_2$CO$_3$ (780 mg, 2.4 mmol) and 1,10-phenanthracene (360 mg, 2.4 mmol) in dry o-xylene (1.5 mL) under Ar (g) were heated at 115° C. for 18 h. After cooling to ambient temperature, NH$_4$Cl (20 mL) and dichloromethane (20 mL) were added and the reaction mixture shaken, the dichloromethane layer was separated and the aqueous layer shaken with dichloromethane (2×20 mL). The combined organic layers were dried over Na$_2$SO$_4$ and concentrated in vacuo to a brown oil. This was purified by liquid chromatography on silica gel eluting with EtOAc to give a solid that was further purified by HPLC to afford 2-(1-pyridin-3-yl-1H-pyrazol-4-yl)pyridine. $^1$H NMR (CD$_3$Cl, 300 MHz) δ 9.08 (1H, d), 8.58-8.64 (2H, m), 8.56 (1H, s), 8.24 (1H, s), 8.12 (1H, ddd), 7.73 (1H, ddd), 7.56-7.59 (1H, m), 7.45 (1H, dd), 7.19 (1H, ddd). MS (ESI) 223 (M+H)$^+$

COMPOUND 2

Synthesis of 2-(1H-pyrazol-1-yl)pyridine

2-Hydrazinopyridine (7.6 g, 70 mmol), malondialdehyde-bis-(dimethylacetal) (11.5 mL, 70 mmol) and HCl (10 M, 7 mL) in EtOH (100 mL) were heated at 75° C. After 2 h, the resulting reaction mixture was cooled to ambient temperature and concentrated in vacuo to a give a brown solid. This was suspended in H$_2$O (100 mL) and EtOAc (100 mL), and NaHCO$_3$ added until there was no further effervescence. The EtOAc layer was then separated and the aqueous layer shaken with EtOAc (3×100 mL). The combined organic layers were dried over Na$_2$SO$_4$ and concentrated to afford 2-(1H-pyrazol-1-yl)pyridine as a brown oil which was used without further purification. MS (ESI) 147 (M+H)$^+$

COMPOUND 3

Synthesis of 2-(4-bromo-1H-pyrazol-1-yl)pyridine

Bromine (10.8 mL, 210 mmol) in AcOH (50 mL) was added carefully to a solution of 2-(1H-pyrazol-1-yl)pyridine (11 g, 70 mmol) in AcOH (100 mL) to give a brown precipitate. After stirring at ambient temperature for 3 h, the resulting reaction mixture was poured into ice and saturated aqueous Na$_2$S$_2$O$_5$ was added until the liquid phase became clear. The precipitate was removed by filtration and recrystallized from EtOH:H$_2$O to give 2-(4-bromo-1H-pyrazol-1-yl)pyridine as beige crystals. $^1$H NMR (CD$_3$Cl, 300 MHz) δ 8.61 (1H, s), 8.42 (1H, br. s), 7.94-7.96 (1H, m), 7.84 (1H, ddd), 7.69 (1H, s), 7.21-7.28 (1H, m). MS (ESI) 225 (M+H)$^+$

EXAMPLE 5

Synthesis of 3-(1-pyridin-2-yl-1H-pyrazol-4-yl)benzonitrile

A solution of 2-(4bromo-1H-pyrazol-1-yl)pyridine (0.446 g, 2.0 mmol), 3-cyanophenylboronic acid (0.302 g, 2.0 mmol), potassium carbonate (0.552 g, 4.0 mmol) in a mixture of ethylene glycol dimethyl ether (20 mL) and water (4 mL) was degassed by argon bubbling for 15 min., then tetrakis (triphenylphosphine)palladium(0) (20 mg, 0.017 mmol) was added and degassing continued a further 15 min. The resulting solution was stirred at 70° C. for 14 h, whereupon H$_2$O (30 mL) was added, then extracted with EtOAc (3×30 mL) and the combined extracts washed with brine. The organic phase was dried over Na$_2$SO$_4$ and concentrated in vacuo. The crude residue was chromatographed on silica gel eluting with EtOAc:hexane (2:3) to afford a white solid which was recrystallized from EtOAc/Hexane give 3-(1-pyridin-2-yl-1H-pyrazol-4-yl)benzonitrile as a white solid. MP=160-161° C. $^1$H NMR (CD$_3$Cl, 300 MHz) δ 8.88 (s, 1H), 8.45 (d, 1H), 8.03 (s, 1H), 8.01 (d, 1H), 7.87 (d, 1H), 7.86 (s, 1H), 7.81 (d, 1H), 7.57~7.48 (m, 2H), 7.25 (dd, 1H). MS (ESI) 247.1 (M$^+$+H).

EXAMPLE 6

Synthesis of 2-[4-(3-chlorophenyl)-1H-pyrazol-1-yl]pyridine

A solution of 2-(4-bromo-1H-pyrazol-1-yl)pyridine (0.669 g, 3 mmol), 3-chlorophenylboronic acid (0.468 g, 3 mmol) and potassium carbonate (0.828 g, 6 mmol) in a mixture of ethyleneglycol dimethyl ether (20 mL) and $H_2O$ (4 mL) were degassed by argon bubbling for 15 min., then tetrakis(triphenylphosphine)palladium(0) (20 mg, 0.017 mmol) was added and degasing continued a further 15 min. The solution was stirred at 70° C. for 14 h, whereupon $H_2O$ (30 mL) was added, then extracted with EtOAc (3×30 mL) and the combined extracts washed with brine. The organic phase was dried over $Na_2SO_4$, concentrated in vacuo and the crude residue was chromatographed on silica gel eluting with EtOAc:hexane (1:4) to afford a white solid which was recrystallized from EtOAc/Hexane to give 2-[4(3-chlorophenyl)-1H-pyrazol-1-yl]pyridine. MP=110-111° C. $^1$H NMR ($CD_3Cl$, 300 MHz) δ 8.83 (d, 1H), 8.42 (dd, 1H), 7.99 (s, 1H), 7.99 (d, 1H), 7.82 (ddd, 1H), 7.57 (t, 1H), 7.45 (dt, 1H), 7.32 (t, 1H), 7.25~7.18 (m, 2H). MS (ESI) 255.9 ($M^+$+H).

EXAMPLE 7

Synthesis of 2-[4-(3-methoxyphenyl)-1H-pyrazol-1-yl]pyridine

A solution of 2-(4bromo-1H-pyrazol-1-yl)pyridine (0.669 g, 3.0 mmol), 3-methoxyphenylboronic acid (0.453 g, 3.0 mmol) and potassium carbonate (0.828 g, 6.0 mmol) in a mixture of ethyleneglycol dimethyl ether (20 mL) and $H_2O$ (4 mL) were degassed by argon bubbling for 15 min., then tetrakis(triphenylphosphine)palladium(0) (20 mg, 0.017 mmol) was added and degassing continued a further 15 min. The resulting solution was stirred at 70° C. for 14 h, whereupon $H_2O$ (30 mL) was added, then extracted with EtOAc (3×30 mL) and the combined extracts washed with brine. The organic phase was dried over $Na_2SO_4$, concentrated in vacuo, and the crude residue was chromatographed on silica gel eluting with EtOAc:hexane (1:4) afford a white solid which was recrystallized from EtOAc/Hexane to give 2-[4(3-methoxyphenyl)-1H-pyrazol-1-yl]pyridine. MP=89-90° C. $^1$H NMR ($CD_3Cl$, 300 MHz) δ 8.84 (s, 1H), 8.45 (dd, 1H), 8.03 (s, 1H), 8.02 (d, 1H), 7.84 (dd, 1H), 7.34 (t, 1H), 7.23~7.15 (m, 3H), 6.84 (dd, 1H) 3.87 (s, 3H). MS (ESI) 252.1 ($M^+$+H).

COMPOUND 4

Synthesis of 2-(1H-pyrazol-3-yl)pyridine 2-(1H-Pyrazol-3-yl)pyridine (7.8 g) was prepared according to the method of: Wang, F.; Schwabacher, A. W. *Tetrahedron. Lett.* 1999. 40, 4779-4782.

EXAMPLE 8

Synthesis of 3-(3-pyridin-2-yl-1H-pyrazol-1-yl)benzonitrile 2-(1H-Pyrazol-3-yl)pyridine (435 mg, 3 mmol), 3-fluorobenzonitrile (0.32 mL, 3 mmol) and $K_2CO_3$ (830 mg, 6 mmol) were dissolved in DMF (10 mL) under Ar (g) and heated at 145° C. for 18 h. After cooling to ambient temperature, $H_2O$ (40 mL) and EtOAc (40 mL) were added and the reaction mixture shaken, the EtOAc layer was separated and the aqueous layer shaken with EtOAc (2×30 mL). The combined organic layers were washed with brine (3×40 mL), dried over $Na_2SO_4$ and concentrated onto silica gel. The crude material was purified by liquid chromatography on silica gel eluting with EtOAc:hexane (1:1) to afford a solid that was recrystallized from EtOAc-hexane to give 3-(3-pyridin-2-yl-1H-pyrazol-1-yl)benzonitrile as a solid. $^1$H NMR ($CD_3Cl$, 300 MHz) δ 8.68-8.71 (1H, m), 8.18 (1H, m), 8.12-8.15 (1H, m), 8.02-8.06 (2H, m), 7.81 (1H, ddd), 7.60-7.62 (2H, m), 7.30 (1H, ddd), 7.20 (1H, d). MS (ESI) 247 $(M+H)^+$

EXAMPLE 9

Synthesis of 2-[1-(3-chlorophenyl)-1H-pyrazol-3-yl]pyridine 2-(1H-Pyrazol-3-yl)pyridine (435 mg, 3 mmol), 3-fluoro-1-chlorobenzene (0.32 mL, 3 mmol) and $K_2CO_3$ (830 mg, 6 mmol) were dissolved in DMF (10 mL) under Ar (g) and heated at 145° C. for 18 h. After cooling to ambient temperature, $H_2O$ (40 mL) and EtOAc (40 mL) were added and the reaction mixture shaken, the EtOAc layer was separated and the aqueous layer shaken with EtOAc (2×30 mL). The combined organic layers were washed with brine (3×40 mL), dried over $Na_2SO_4$ and concentrated onto silica gel. The crude material was purified by liquid chromatography on silica gel, eluting with EtOAc:hexane (1:1) to afford 2-[1-(3-chlorophenyl)-1H-pyrazol-3-yl]pyridine as as solid. $^1$H NMR ($CD_3Cl$, 300 MHz) δ 8.68-8.69 (1H, m), 8.13-8.16 (1H, m), 8.01 (1H, m), 7.88 (11H, m), 7.79 (1H, ddd), 7.66-7.68 (1H, m), 7.42 (1H, dd), 7.26-7.31 (2H, m), 7.16 (1H, d). MS (ESI) 256 $(M+H)^+$

COMPOUND 5

Synthesis of (2E)-3-ethoxy-N'-pyridin-2-ylprop-2-enohydrazide

Ethyl vinyl ether (4.73 g, 65.6 mmol) was added dropwise to oxalyl chloride (12.5 g, 98.4 mmol) at 0° C., the resulting reaction mixture was first stirred at 0° C. for 2 h, and then allowed to warm to ambient temperature. After 12 h GC/MS analysis indicated formation of product and the reaction mixture was concentrated in vacuo and the crude (2E)-3-ethoxyprop-2-enoyl chloride used in the next step without further purification.

To a cold (0° C.) solution of 2-hydrazinopyridine (10.74 g, 98.4 mmol) and triethylamine (9.94 g, 98.4 mmol) in THF (100 mL) was added crude (2E)-3-ethoxyprop-2-enoyl chloride (based on 100% yield of previous step) dropwise. The resulting reaction mixture was allowed to warm to ambient temperature over 2 h and then heated at reflux for a further 5 h. The reaction mixture was quenched with water (50 mL), extracted with EtOAc (3×50 mL) and washed with brine. The organic phase was dried over $Na_2SO_4$, concentrated in vacuo, purified using liquid chromatography on silica gel eluting with EtOAc to afford (2E)-3-ethoxy-N'-pyridin-2-ylprop-2-enohydrazide as a brown oil. $^1$H NMR ($CD_3Cl$, 300 MHz) δ 9.19 (br, 1H), 8.08 (d, 1H), 7.59~7.44 (m, 3H), 6.75~6.69 (m, 2H), 5.34 (d, 1H), 3.81 (q, 2H), 1.27 (t, 3H). MS (ESI) 208 ($M^+$+H).

COMPOUND 6

Synthesis of 1-pyridin-2-yl-1,2-dihydro-3H-pyrazol-3-one (2E)-3-Ethoxy-N'-pyridin-2-ylprop-2-enohydrazide (8.5 g, 41 mmol) was stirred with concentrated 37% HCl (20 mL) for 3 h. The resulting reaction mixture was adjusted to pH 7 using 1N NaOH (aq) and a precipitate formed. The reaction mixture then extracted with EtOAc (3×50 mL)and washed with brine. The combined organic phase was dried over Na₂SO₄, concentrated in vacuo purified using liquid chromatography on silica gel eluting with EtOAc (100%) to afford 1-pyridin-2-yl-1,2-dihydro-3H-pyrazol-3-one as a yellow solid. ¹H NMR (CD₃Cl, 300 MHz) δ 12.00 (br, 1H), 8.43~8.39 (m, 2H), 7.85 (ddd, 1H), 7.64 (d, 1H), 7.16 (ddd, 1H), 5.99 (d, 1H). MS (ESI) 162 (M⁺+H).

COMPOUND 7

Synthesis of 1-pyridin-2-yl-1H-pyrazol-3-yl trifluoromethanesulfonate

To a solution of 1-pyridin-2-yl-1,2dihydro-3H-pyrazol-3-one (0.161 g, 1.0 mmol) and triethylamine (0.112 g, 1.1 mmol) in THF (10 mL) at −78° C. was added trifluoromethanesulfonic anhydride (0.253 g, 1 mmol) dropwise. The resulting reaction mixture was stirred and allowed to warm to ambient temperature over 4 h. The reaction was quenched by the addition of H₂O (15 mL), then extracted with EtOAc (3×20 mL) and washed with brine. The combined organic extracts were dried over Na₂SO₄ and concentrated in vacuo. The crude residue was chromatographed on silica gel eluting with EtOAc:hexane (1:9) to afford 1-pyridin-2-yl-1H-pyrazol-3-yl trifluoromethanesulfonate as white crystals. ¹H NMR (CD₃Cl, 300 MHz) δ 8.57 (d, 1H), 8.43 (d, 1H), 7.91~7.83 (m, 2H), 7.29~7.25 (m, 1H) 6.38 (d, 1H). MS (ESI) 294 (M⁺+H).

EXAMPLE 10

Synthesis of 3-(1-pyridin-2-yl-1H-pyrazol-3-yl)benzonitrile

1-Pyridin-2-yl-1H-pyrazol-3-yl trifluoromethanesulfonate (0.211 g, 0.72 mmol), 3-fluorobenzonitrile (0.111 g, 0.76 mmol) and potassium carbonate (0.209 g, 1.51 mmol) in a mixture of ethyleneglycol dimethyl ether (20 mL) and water (4 mL) was degassed by argon bubbling for 15 min., then tetrakis(triphenylphosphine)palladium(0) (20 mg, 0.017 mmol) was added the resulting solution degassed for a further 15 min. The solution was stirred at 65° C. for 12 h. The reaction mixture was quenched with water (30 mL), then extracted with EtOAc (3×30 mL) and washed with brine. The combined organic phase was dried over Na₂SO₄ and concentrated in vacuo. The crude residue was chromagraphed on silica gel eluting with EtOAc:hexane (2:3) to afford a white solid which was recrystallized from EtOAc-hexane to give 3-(1-pyridin-2-yl-1H-pyrazol-3-yl)benzonitrile as a white solid. ¹H NMR (CD₃Cl, 300 MHz) δ 8.64 (d, 1H), 8.44 (d, 1H), 8.25 (s, 1H), 8.14 (d, 1H), 8.10 (d, 1H), 7.87 (t, 1H), 7.64 (d, 1H), 7.55 (t, 1H), 7.24 (dd, 1H), 6.80 (d, 1H). MS (ESI) 247 (M⁺+H).

COMPOUND 8

Synthesis of 2-bromo-6-hydrazinopyridine 2,5-Dibromopyridine (2.0 g, 8.4 mmol) was dissolved in 1,4-dioxane (2 mL) and a solution of hydrazine hydrate (500 mg, 8.4 mmol) in 1,4-dioxane (15 mL) was added dropwise by syringe pump. The reaction was heated to 80° C. for 16 h. The solvents were removed in vaccuo and the residue was chromatographed on silica gel eluting with hexanes:EtOAc (1:1) to afford 2-bromo-6-hydrazinopyridine as a brown solid. MS (ESI) 187.0 (M⁺+H), 189.0 (M+H+2).

EXAMPLE 11

Synthesis of 2-bromo-6-(4-pyridin-2-yl-1H-pyrazol-1-yl)pyridine

2-Bromo-6-hydrazinopyridine (500 mg, 2.7 mmol) was dissolved in ethanol (10 mL) and 2-(2-pyridyl)malondialdehyde(403 mg, 2.7 mmol) was added. The reaction was heated at 70° C. for 16 h. The solvents were removed the ethanol in vacuo and the residue was chromatographed on silica gel eluting with hexanes:EtOAc (1:4) to afford 2-bromo-6-(4-pyridin-2-yl-1H-pyrazol-1-yl)pyridine as a light yellow solid. ¹H-NMR (CDCl₃, 300 MHz) δ 9.0 (s, 1H), 8.62-8.61 (d, J=3 Hz 1H), 8.27 (s, 1H), 7.97-7.94 (d, J=9 Hz, 1H), 7.74-7.57 (m, 3H), 7.39-7.37 (d, J=3 Hz, 1H) 7.19-7.15 (t, 1H). MS (ESI) 301.0 (M⁺+H), 303.0 (M+H+2).

COMPOUND 9

Synthesis of 6-fluoropyridine-2-carbonitrile 2,6 Difluoropyridine (12 g, 100 mmol) was dissolved in DMSO (3 mL) and sodium cyanide (1.3 g, 26 mmol) in DMSO (100 mL) was added dropwise via syringe pump over 16 h. The reaction was then heated at 100° C. for 16 h. The crude mixture was then diluted with EtOAc (500 mL) and washed with a mixture of brine (200 mL) and H₂O (500 mL). The organic phase was dried (MgSO₄), filtered, and concentrated in vacito. The residue was chromatographed on silica gel eluting with hexanes:EtOAc (4:1) to afford 6-fluoropyridine-2-carbonitrile. MS (ESI) 122.0 (M⁺+H).

EXAMPLE 12

Synthesis of 6-(4-pyridin-2-yl-1H-pyrazol-1-yl)pyridine-2-carbonitrile 2-(1H-Pyrazol-4-yl)pyridine (300 mg, 2.0 mmol) was dissolved in DMF (10 mL), potassium carbonate (566 mg, 4 mmol) and 6-fluoropyridine-2-carbonitrile (250 mg, 2 mmol) was added. The reaction was heated at 140° C. for 16 h. The crude mixture was cooled to rt and diluted with EtOAc (300 mL) and washed with H₂O (200 mL) and brine (200 mL). The organic phase was dried (MgSO₄), filtered, and concentrated in vacuo. The residue was chromatographed on silica gel eluting with hexanes:EtOAc (7:3) to afford 6-(4-pyridin-2-yl-1H-pyrazol-1-yl)pyridine-2-carbonitrile. This material was dissolved in methylene chloride (5 mL) and, upon treatment with 1M HCl in diethyl ether (0.6 mL), precipitated as the hydrochloride salt. M.P. 260-261° C. ¹H-NMR (CDCl₃, 300 MHz) δ 9.67 (s, 1H), 8.83 (s, 1H), 8.79-8.77 (d, J=6 Hz, 1H), 8.47-8.29 (m, 4H), 8.13-8.10 (m, 1H) 7.77-7.73 (t, 1H). MS ESI) 249 (M⁺+H).

EXAMPLE 13

Synthesis of 2-[1-(3-bromophenyl)-1H-pyrazol-4-yl]pyridine 2-(2-Pyridyl)malondialdehyde (100 mg, 0.67 mmol) and 3-bromophenylhydrazine hydrochloride (150 mg, 0.67 mmol) were suspended in ethanol (2 mL), and heated to 75° C. for 8 h. The reaction mixture was concentrated in vacuo and the residue was purified by silica gel preparative TLC eluting with hexanes:EtOAc (3:1) to afford 2-[1-(3-bromophenyl)-1H-pyrazol-4-yl]pyridine as a pale yellow solid. $^1$H-NMR (CDCl$_3$, 300 MHz) δ 8.61 (d, J=4.8 Hz, 1H), 8.51 (s, 1H), 8.18 (s, 1H), 7.99 (s, 1H), 7.73-7.68 (m, 2H), 7.55 (d, J=7.9 Hz, 1H), 7.43 (d, J=8.8 Hz, 1H), 7.35 (t, J=8.1 Hz, 1H), 7.17 (dd, J=4.9, 7.4 Hz, 1H). MS (ESI) 300.0, 302.0 (M$^+$+H).

COMPOUND 10

Synthesis of 3-(4-bromo-1H-pyrazol-1-yl)benzonitrile

3-Fluorobenzonitrile (4.4 mL, 40 mmol), 4-bromopyrazole (6 g, 40 mmol) and potassium carbonate (11 g, 80 mmol) were weighed into a flask and flushed with Ar(g). Dry DMF (80 mL) was added and the reaction mixture was stirred at 140° C. for 18 h. The reaction mixture was then cooled to rt and partitioned between EtOAc (200 mL) and brine (100 mL). The organic layer was separated and the aqueous layer was washed with EtOAc (3×150 mL), the combined organic layers were washed with brine (3×50 mL), dried over Na$_2$SO$_4$, filtered and concentrated to afford a solid. This was recrystallized from EtOAc/hexane to give 3-(4-bromo-1H-pyrazol-1-yl)benzonitrile as a beige solid.

COMPOUND 11

Synthesis of 3-[4-(4,4,5,5-tetramethyl-1,3,2-dioxaborolan-2-yl)-1H-pyrazol-1-yl]benzonitrile 3-(4-Bromo-1H-pyrazol-1-yl)benzonitrile (4.4 g, 18 mmol), bis(pinacolato)diborane (5 g, 20 mmol), potassium acetate (5.3 g, 54 mmol) and Pd(dppf)$_2$Cl$_2$.CHCl$_3$ (1.47 g, 1.8 mmol) were weighed into a flask and flushed with Ar(g). Dry 1,4-dioxane (100 mL) was added, the reaction mixture degassed for 10 min with Ar(g) and then heated to 80° C. After 18 h, the reaction mixture was cooled to rt and partitioned between EtOAc (100 mL) and brine (100 mL) and filtered through Celite. The organic layer was separated and the aqueous layer was washed with EtOAc (3×70 mL), dried over Na$_2$SO$_4$, filtered and concentrated to an oil. This was purified by chromatography on silica gel eluting with EtOAc:hexane (2:8) to afford 3-[4-(4,4,5,5-tetramethyl-1,3,2-dioxaborolan-2-yl)-1H-pyrazol-1-yl]benzonitrile as an orange solid.

EXAMPLE 14

Synthesis of 3-(4-pyrazin-2-yl-1H-pyrazol-1-yl)benzonitrile

3-[4-(4,4,5,5-Tetramethyl-1,3,2-dioxaborolan-2-yl)-1H-pyrazol-1-yl]benzonitrile (446 mg, 1.5 mmol), cesium fluoride (912 mg, 6 mmol) and tetrakis(triphenylphosphino)palladium(0) (173 mg, 0.15 mmol) were weighed into a flask and flushed with Ar(g). Dry DME (20 mL) was added, the reaction mixture degassed for 10 min. with Ar(g) and then heated to 95° C. After 18 h, the reaction mixture was cooled to rt and partitioned between EtOAc (50 mL) and brine (50 mL). The organic layer was separated and the aqueous layer was washed with EtOAc (3×50 mL), dried over Na$_2$SO$_4$, filtered and concentrated onto silica gel. This was purified by chromatography on silica gel eluting with EtOAc:hexane (7:3) to give 3-(4-pyrazin-2-yl-1H-pyrazol-1-yl)benzonitrile as a white solid. This was dissolved in dichloromethane and HCl (1M in Et$_2$O) was added to give a fine precipitate. The solvent was removed in vacuo and the residue reconstituted in Et$_2$O. The precipitate was removed by filtration washing with Et$_2$O to give the hydrochloride salt of 3-(4-pyrazin-2-yl-1H-pyrazol-1-yl)benzonitrile.

$^1$H-NMR (CDCl$_3$, 300 MHz) δ9.42 (s, 1H), 9.13 (s, 1H), 8.66 (m, 1H), 8.51-8.53 (m, 2H), 8.45 (m, 1H), 8.30-8.32 (m, 1H), 7.84-7.87 (m, 1H), 7.77 (dd, 1H).

MS 248.0 (M+H)$^+$.

COMPOUND 12

Synthesis of 3-fluoro-5-(4-iodo-1H-pyrazol-1-yl)benzonitrile

To a solution of 4-iodopyrazole (1.67 g, 8.63 mmol) in DMF (40 mL) is added NaH (9.35 mmol, 374 mg of 60% dispersion in oil). Reaction was stirred for 15 min at 60° C., then 3,5-difluorobenzonitrile (1.0 g, 7.19 mmol) was added and the mixture was warmed to 125° C. After 1 hr, TLC analysis showed disappearance of starting 3,5-difluorobenzonitrile. Reaction was cooled to room temperature and poured in to a separatory funnel containing 1:1 hexanes:EtOAc (200 mL) and 10% brine (100 mL).

The organic layer was washed with additional 10% brine (2×50 mL), then dried over MgSO$_4$, filtered, and concentrated in vacuo. Residue was then dissolved in hot EtOAc (ca. 300 mL) and allowed to cool overnight. The product-containing mother liquor was decanted away from the resulting solid material and concentrated in vacuo to afford 3-fluoro-5-(4-iodo-1H-pyrazol-1-yl)benzonitrile as a white solid. $^1$H NMR (CDCl$_3$, 500 MHz) δ 7.99 (s, 1H), 7.78 (s, 1H), 7.76 (s, 1H), 7.68-7.72 (m, 1H), 7.29-7.31 (m, 1H).

EXAMPLE 15

Synthesis of 3-(1'H-1,4'-bipyrazol-1'-yl)-5-fluorobenzonitrile

To a sealed tube containing dry, deoxygenated dioxane (1 mL) was added 3-fluoro-5-(4-iodo-1H-pyrazol-1-yl)benzonitrile (313 mg, 1.0 mmol), pyrazole (88 mg, 1.3 mmol), trans-diaminocyclohexane (24 μL, 0.2 mmol), potassium carbonate (304 mg, 2.2 mmol), and CuI (4 mg, 0.02 mmol). The reaction was capped and heated with stirring for 48 hr at 100° C. The resulting mixture was partitioned with EtOAc (10 mL) and H$_2$O (10 mL). The organic layer was dried over MgSO$_4$, filtered, and concentrated in vacuo on to a plug of silica gel, which was loaded on to a prepacked column and purified via automated flash chromatography utilizing a 5-35% EtOAc/Hexanes gradient to afford 3-(1'H-1,4'-bipyrazol-1'-yl)-5-fluorobenzonitrile as a white solid. $^1$H NMR (CDCl$_3$, 500 MHz) δ 8.48 (s, 1H), 8.04 (s, 1H), 7.96 (m, 1H), 7.85-7.88 (m, 2H), 7.71 (d, 1H), 7.36 (m, 1H), 6.50 (m, 1H). MS (ESI) 254.15 (M$^+$+H).

EXAMPLE 16 to EXAMPLE 277 shown below were prepared similarly to the schemes and procedures described above (ND=not determined).

| EXAMPLE | Structure | ¹H NMR (δ) | MS (ESI) |
|---|---|---|---|
| 16 | 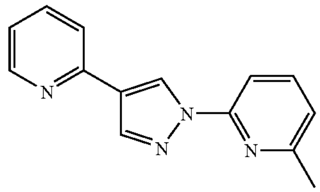 | 9.57 (s, 1H), 8.73-8.71 (d, 1H), 8.61-8.56 (t, 1H), 8.52 (s, 1H), 8.46-8.43 (d, 1H), 7.92-7.84 (m, 3H), 7.31-7.28 (d, 1H), 2.60 (s, 3H). | MS 237 (M$^+$ + H). |
| 17 | 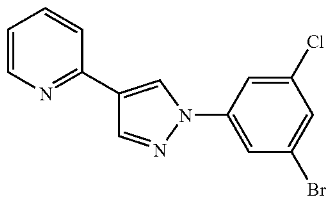 | 8.63-8.61 (m, 1H), 8.49, (s, 1H), 8.20 (s, 1H), 7.89-7.87 (t, 1H), 7.78-7.77 (t, 1H), 7.74-7.71 (dd, 1H), 7.59-7.55 (d, 1H), 7.46-7.45 (t, 1H), 7.22-7.18 (m, 1H). | MS 304.0 (M$^+$ + H), 306.0 (M + H + 2), 308.0(M + 4). |
| 18 | 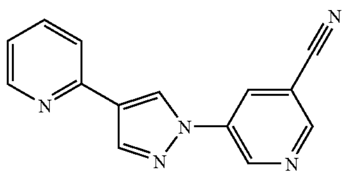 | 9.63 (s, 1H), 9.45-9.44 (d, 1H), 9.04-9.03 (d, 1H), 8.85-8.84 (t, 1H), 8.74 (s, 1H), 8.71-8.70 (d, 1H), 8.29-8.24 (t, 1H), 8.12-8.10 (d, 1H), 7.63-7.59 (t, 1H) | MS 248.0 (M$^+$ + H) |
| 19 | 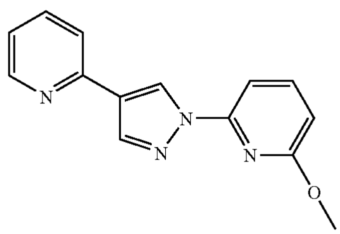 | 9.5 (s, 1H), 8.72-8.71 (d, 1H), 8.58-8.47 (m, 4H), 7.88-7.81 (m, 2H), 7.55-7.52 (d, 1H), 6.80-6.77 (d, 1H), 4.02 (s, 3H). | MS 253.0 (M$^+$ + H). |
| 20 | 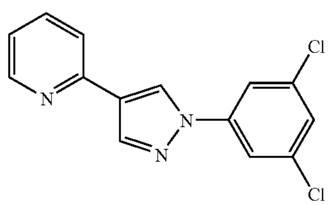 | 8.61-8.60 (d, 1H), 8.48 (s, 1H), 8.22 (s, 1H), 7.72-7.70 (m, 3H), 7.56-7.54 (d, 1H), 7.30-7.29 (m, 1H), 7.19-7.17 (dd, 1H). | MS 290.0, 292.0 (M$^+$ + H). |
| 21 | 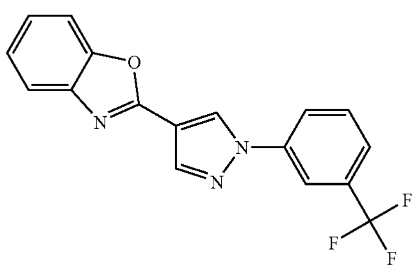 | 8.73 (s, 1H), 8.43 (s, 1H), 8.11 (s, 1H), 8.00-7.99 (d, 1H), 7.80-7.76 (m, 1H), 7.71-7.63 (m, 2H), 7.61-7.58 (m, 1H), 7.41-7.40 (t, 1H), 7.39-7.37 (t, 1H). | MS 330.07 (M$^+$ + H). |
| 22 | 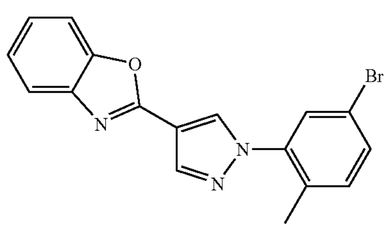 | 8.36-8.30 (m, 2H), 7.71-7.19 (m, 7H), 2.67 (s, 3H). | MS 354.0, 355.88 (M$^+$ + H). |

| EXAMPLE | Structure | ¹H NMR (δ) | MS (ESI) |
| --- | --- | --- | --- |
| 23 | 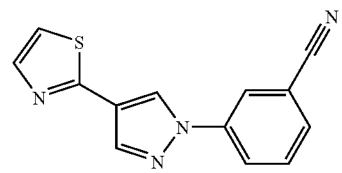 | 9.31 (s, 1H), 8.46 (m, 1H), 8.29-8.33 (m, 2H), 7.83-7.87 (m, 2H), 7.72-7.75 (m, 2H). | MS 253.0 (M + H)⁺. |
| 24 | 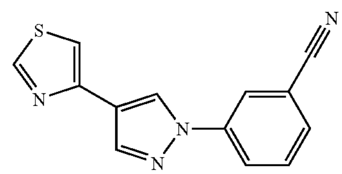 | 9.20 (d, 1H), 9.12 (s, 1H), 8.41 (m, 1H), 8.27-8.29 (m, 2H), 7.91 (d, 1H), 7.79-7.81 (m, 1H), 7.73 (dd, 1H). | MS 253.0 (M + H)⁺. |
| 25 | 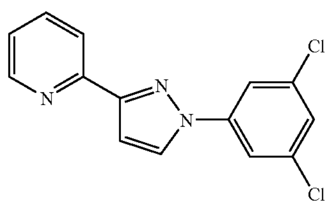 | 8.61 (d, 1H), 8.10 (t, 1H), 7.92 (s, 1H), 7.72 (d, 1H), 7.64 (m, 1H), 7.58 (m, 1H), 7.41 (s, 2H), 7.08 (s, 1H) | MS 290.2 (M⁺ + H). |
| 26 | 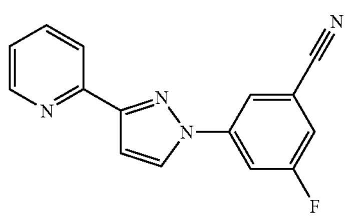 | 8.75 (s, 1H), 8.64 (s, 1H), 8.50 (s, 1H), 8.23 (d, 1H), 8.15 (d, 1H), 7.95 (t, 1H), 7.90 (d, 1H), 7.40 (d, 1H), 7.17 (s, 1H) | MS 265.09 (M⁺ + H). |
| 27 | 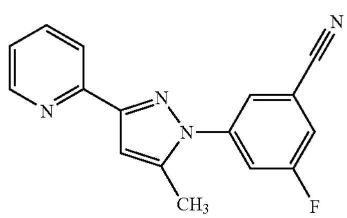 | 8.62 (s, 1H), 8.09 (s, 1H), 8.01 (m, 3H), 7.86 (m, 1H), 7.37 (m, 1H), 6.92 (s, 1H), 2.50 (s, 3H) | MS 279.15 (M⁺ + H). |
| 28 | 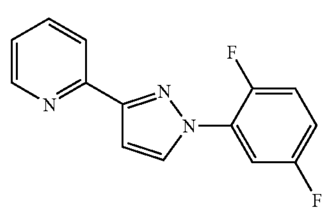 | 8.51 (d, 1H), 8.03 (t, 1H), 7.94 (d, 1H), 7.74 (d, 1H), 7.59 (m, 1H), 7.45 (m, 1H), 7.38 (m, 2H), 7.15 (d, 1H) | MS 258.06 (M⁺ + H). |
| 29 | 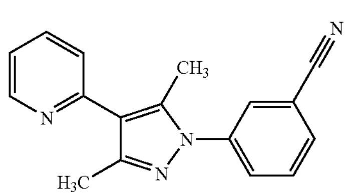 | 8.73 (m, 1H), 7.84 (m, 1H), 7.76-7.81 (m, 2H), 7.60-7.70 (m, 2H), 7.39 (d, 1H), 7.21-7.25 (m, 1H), 2.50 (s, 3H), 2.46 (s, 3H). | MS 275 (M⁺ + H). |

| EXAMPLE | Structure | ¹H NMR (δ) | MS (ESI) |
|---|---|---|---|
| 30 | 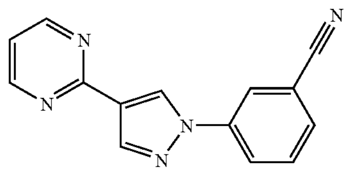 | 9.34 (s, 1H), 8.84 (d, 1H), 8.50 (m, 1H), 8.41 (s, 1H), 8.33-8.35 (m, 1H), 7.83 (m, 1H), 7.42 (m, 1H), 7.38 (t, 1H) | MS 248 (M⁺ + H). |
| 31 | 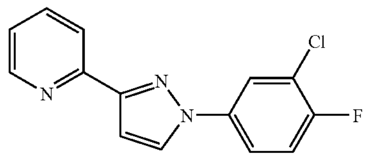 | 8.57 (d, 1H), 8.02 (m, 1H), 7.88 (d, 1H), 7.63 (d, 2H), 7.50 (m, 1H), 7.45 (d, 1H), 7.32 (m, 1H), 7.03 (d, 1H). | MS 274.0 (M⁺ + H). |
| 32 | 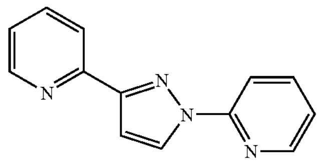 | 8.75 (d, 1H), 8.35 (t, 1H), 8.12 (d, 1H), 8.05 (m, 1H), 7.98 (d, 1H), 7.88 (d, 2H), 7.82 (t, 1H), 7.35 (m, 1H), 7.10 (d, 1H). | MS 223.0 (M⁺ + H). |
| 33 | 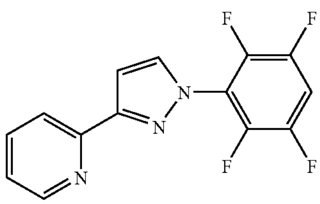 | 8.34 (d, 1H), 8.20 (m, 1H), 8.05 (m, 1H), 7.95 (m, 2H), 7.34 (m, 1H), 7.26 (d, 1H). | MS 294.0 (M⁺ + H). |
| 34 | 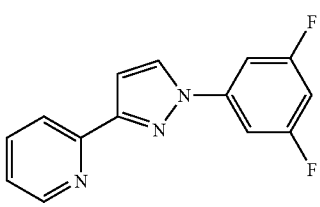 | 8.65 (d, 1H), 8.10 (m, 1H), 7.92 (d, 1H), 7.69 (d, 1H), 7.60 (m, 1H), 7.38 (m, 1H), 7.13 (m, 2H), 7.10 (d, 1H). | MS 258.1 (M⁺ + H). |
| 35 | 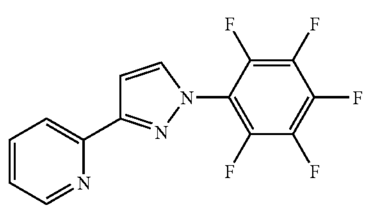 | 8.36 (d, 1H), 8.03 (d, 1H), 7.95 (m, 1H), 7.35 (m, 2H), 7.30 (d, 1H). | MS 312.0 (M⁺ + H). |
| 36 | 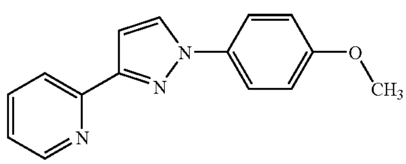 | 8.67 (d, 1H), 8.02 (m, 1H), 7.85 (d, 1H), 7.57 (m, 1H), 7.40 (d, 1H), 7.27 (d, 2H), 7.00 (d, 1H), 6.98 (d, 2H), 3.80 (s, 3H). | MS 252.2 (M⁺ + H). |
| 37 | 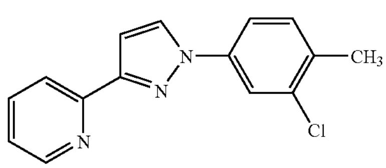 | 8.55 (d, 1H), 7.95 (m, 1H), 7.85 (d, 1H), 7.55 (m, 1H), 7.45 (m, 1H), 7.38 (d, 1H), 7.35 (d, 1H), 7.10 (dd, 1H), 6.92 (d, 1H), 2.35 (s, 3H). | MS 270.1 (M⁺ + H). |

-continued

| EXAMPLE | Structure | ¹H NMR (δ) | MS (ESI) |
| --- | --- | --- | --- |
| 38 | 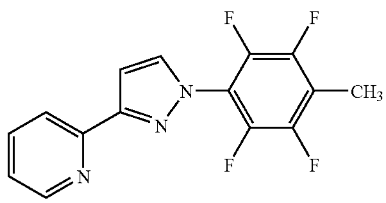 | 8.32 (m, 1H), 7.98 (d, 1H), 7.90 (m, 2H), 7.33 (m, 1H), 7.23 (d, 1H), 2.35 (s, 3H). | MS 308.1 (M⁺ + H). |
| 39 | 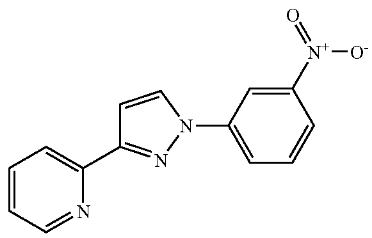 | 8.55 (d, 1H), 8.35 (m, 1H), 8.17 (m, 1H), 8.08 (m, 1H), 7.98 (d, 1H), 7.75 (m, 2H), 7.72 (t, 1H), 7.55 (m, 1H), 7.20 (d, 1H). | MS 267.1 (M⁺ + H). |
| 40 | 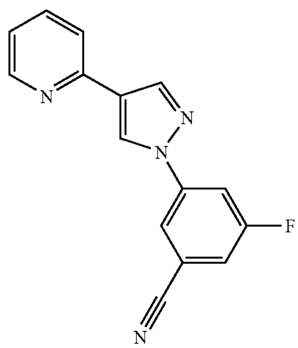 | 8.61-8.62 (s, 1H), 8.51 (s, 1H), 8.21 (s, 1H), 7.90 (s, 1H), 7.79-7.80 (d, 1H), 7.72-7.75 (m, 1H), 7.55-7.56 (d, 1H), 7.29-7.30 (d, 1H), 7.20-7.23 (m, 1H). | MS 265.1 (M⁺ + H). |
| 41 | 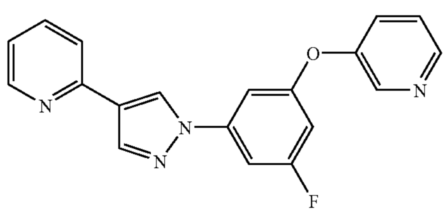 | 9.36 (s, 1H), 8.85 (s, 1H), 8.73-8.74 (d, 1H), 8.68-8.69 (d, 1H), 8.56-8.60 (m, 1H), 8.49 (s, 1H), 8.33-8.39 (m, 2H), 8.07-8.08 (m, 1H), 7.88-7.91 (m, 1H), 7.73 (s, 1H), 7.71 (s, 1H), 7.09-7.14 (d, 1H). | MS 333.1 (M⁺ + H). |
| 42 | 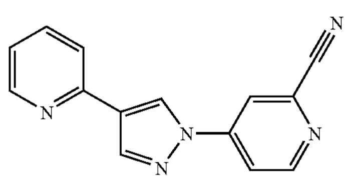 | 9.95 (s, 1H), 8.92 (s, 1H), 8.88-8.90 (d, 1H), 8.74-8.76 (d, 1H), 8.56 (s, 1H), 8.42-8.47 (m, 1H), 8.29 (s, 1H), 8.21-8.26 (m, 1H), 7.74-7.78 (m, 1H). | MS 248.1 (M⁺ + H). |
| 43 | 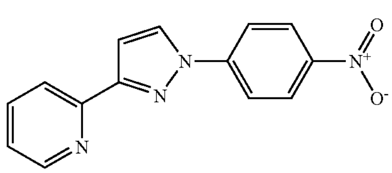 | 8.50 (d, 1H), 8.26 (d, 2H), 7.95 (m, 1H), 7.90 (d, 1H), 7.72 (d, 1H), 7.50 (d, 2H), 7.45 (m, 1H), 7.03 (d, 1H). | MS 267.1 (M⁺ + H). |
| 44 | 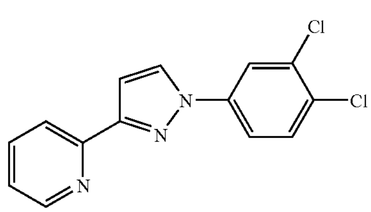 | 8.52 (d, 1H), 7.92 (m, 1H), 7.88 (d, 1H), 7.63 (m, 2H), 7.60 (d, 1H), 7.40 (m, 1H), 7.22 (dd, 1H), 6.95 (d, 1H). | MS 290.1 (M⁺ + H). |

-continued

| EXAMPLE | Structure | ¹H NMR (δ) | MS (ESI) |
|---|---|---|---|
| 45 | 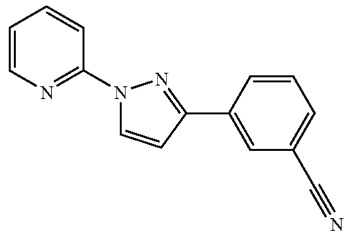 | 8.64-8.63 (d, 1H), 8.45-8.44 (d, 1H), 8.25 (s, 1H), 8.15-8.08 (m, 2H), 7.89-7.84 (m, 1H), 7.65-7.52 (m, 2H), 7.28-7.21 (m, 1H), 6.81-6.80 (d, 1H). | MS 247.1 (M⁺ + H). |
| 46 | 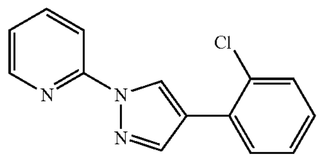 | 8.9474-8.945 (d, 1H), 8.45-8.44 (dd, 1H), 8.08-8.01 (m, 2H), 7.87-7.84 (m, 1H), 7.56-7.47 (m, 2H), 7.36-7.19 (m, 3H). | MS 256.0 (M⁺ + H). |
| 47 | 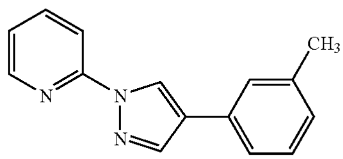 | 8.83 (s, 1H), 8.45-8.43 (m, 1H), 8.02-7.99 (m, 2H), 7.86-7.80 (m, 1H), 7.48-7.02 (m, 5H), 2.40 (s, 3H). | ND |
| 48 | 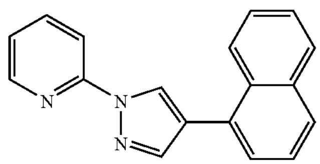 | 8.83 (s, 1H), 8.47-8.44 (m, 1H), 8.24-8.19 (m, 1H), 8.09-8.06 (d, 1H), 8.00 (s, 1H), 7.93-7.83 (m, 3H), 7.57-7.49 (m, 4H), 7.26-7.20 (m, 1H). | ND |
| 49 | 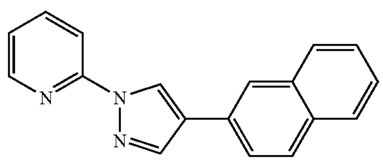 | 8.96 (s, 1H), 8.48-8.45 (m, 1H), 8.16-8.03 (m, 2H), 7.91-7.83 (m, 4H), 7.78-7.09 (m, 5H). | ND |
| 50 | 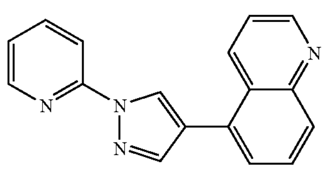 | 8.98-8.95 (m, 1H), 8.20 (d, 1H), 8.56-8.52 (d, 1H), 8.47-8.44 (m, 1H), 8.14-8.06 (m, 2H), 7.97 (s, 1H), 7.92-7.89 (m, 1H), 7.80-7.74 (m, 1H), 7.64-7.62 (m, 1H), 7.47-7.41 (m, 1H), 7.26-7.22 (m, 1H). | ND |
| 51 | 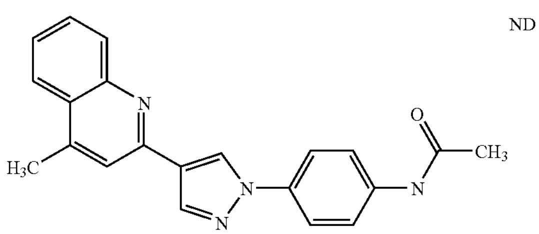 | ND | MS 243 (M⁺ + H). |
| 52 | 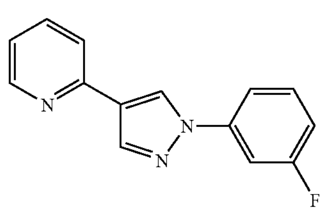 | ND | MS 240 (M⁺ + H). |

-continued

| EXAMPLE | Structure | ¹H NMR (δ) | MS (ESI) |
|---|---|---|---|
| 53 | 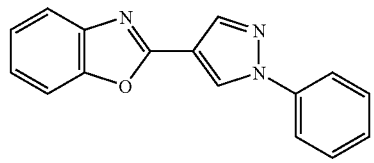 | ND | MS 262 (M⁺ + H). |
| 54 | 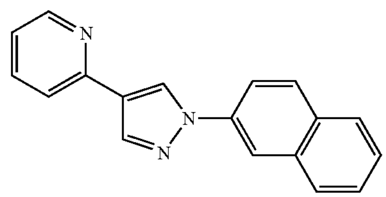 | ND | MS 272 (M⁺ + H). |
| 55 | 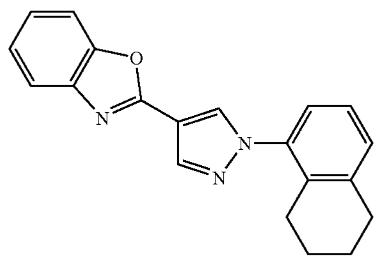 | ND | MS 316 (M⁺ + H). |
| 56 | 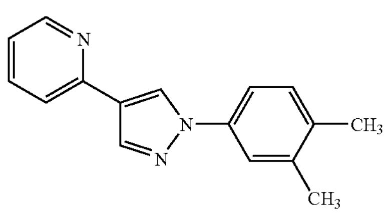 | ND | MS 250 (M⁺ + H). |
| 57 | 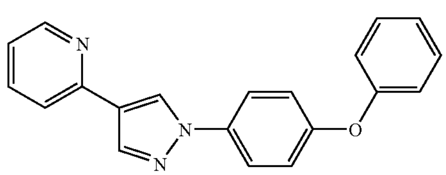 | ND | MS 314 (M⁺ + H). |
| 58 | 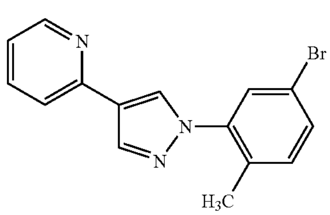 | ND | MS 314, 315 (M⁺ + H). |
| 59 | 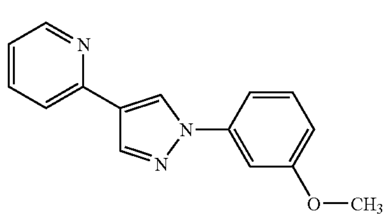 | ND | MS 252 (M⁺ + H). |

-continued

| EXAMPLE | Structure | ¹H NMR (δ) | MS (ESI) |
|---|---|---|---|
| 60 | 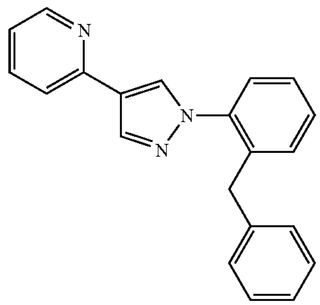 | ND | MS 312 (M⁺ + H). |
| 61 | 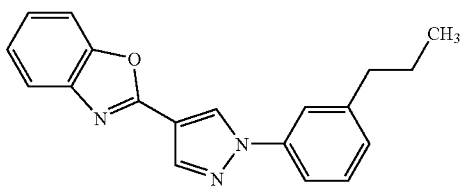 | ND | MS 304 (M⁺ + H). |
| 62 | 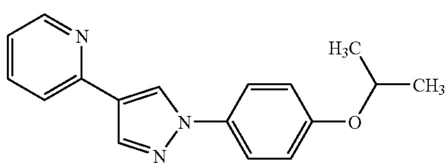 | ND | MS 280 (M⁺ + H). |
| 63 | 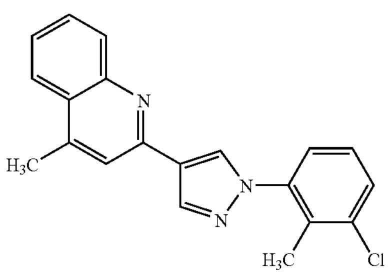 | ND | MS 334 (M⁺ + H). |
| 64 | 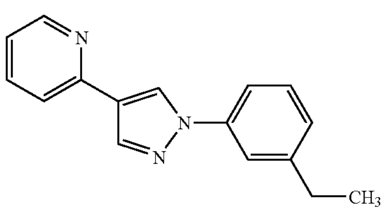 | ND | MS 250 (M⁺ + H). |
| 65 | 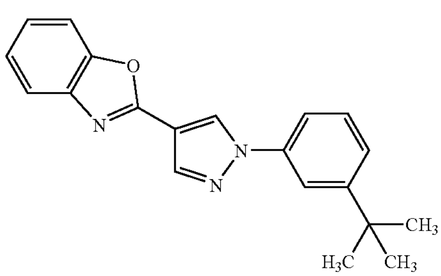 | ND | MS 318 (M⁺ + H). |

-continued

| EXAMPLE | Structure | ¹H NMR (δ) | MS (ESI) |
|---|---|---|---|
| 66 | 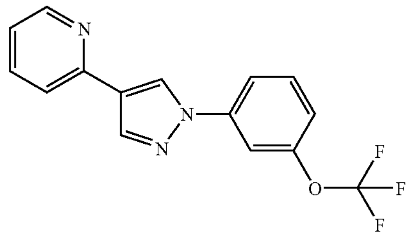 | ND | MS 306 (M⁺ + H). |
| 67 | 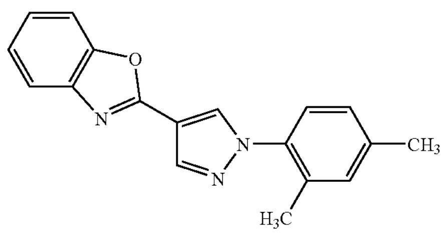 | ND | MS 290 (M⁺ + H). |
| 68 | 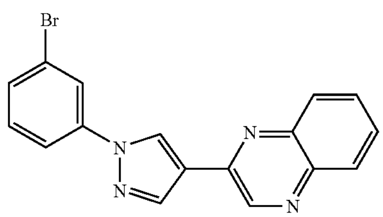 | ND | MS 353 (M⁺ + H). |
| 69 | 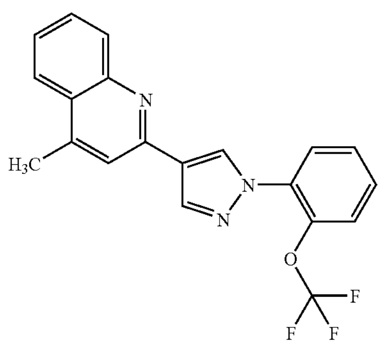 | ND | MS 370 (M⁺ + H). |
| 70 | 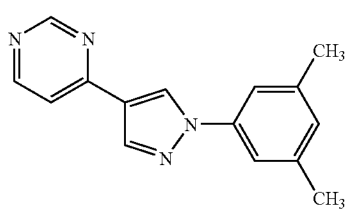 | ND | MS 251 (M⁺ + H). |
| 71 | 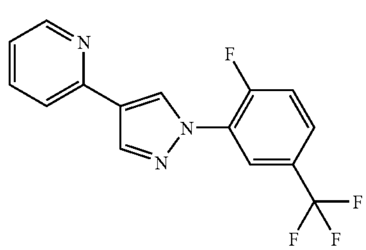 | ND | MS 308 (M⁺ + H). |

-continued

| EXAMPLE | Structure | ¹H NMR (δ) | MS (ESI) |
|---|---|---|---|
| 72 | 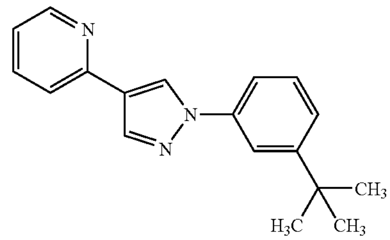 | ND | MS 278 (M⁺ + H). |
| 73 | 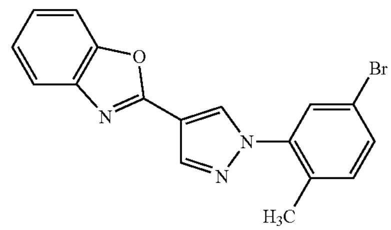 | ND | MS 354, 356 (M⁺ + H). |
| 74 | 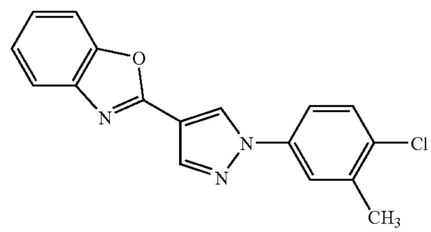 | ND | MS 310 (M⁺ + H). |
| 75 | 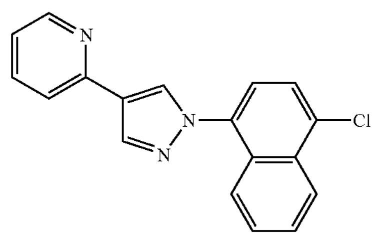 | ND | MS 306 (M⁺ + H). |
| 76 | 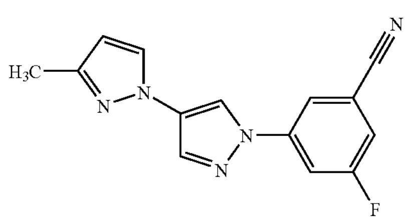 | 8.32 (s, 1H), 7.95 (s, 1H), 7.79 (s, 1H), 7.71-7.75 (m, 1H), 7.64 (d, 1H), 7.27-7.30 (m, 1H), 6.23 (d, 1H), 2.37 (s, 3H). | MS 268.19 (M⁺ + H). |
| 77 | 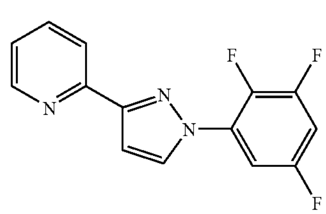 | 8.40 (d, 1H), 7.95 (m, 2H), 7.80 (m, 1H), 7.70 (m, 1H), 7.45 (m, 1H), 7.40 (m, 1H), 6.90 (d, 1H). | MS 276.5 (M⁺ + H). |

-continued

| EXAMPLE | Structure | ¹H NMR (δ) | MS (ESI) |
|---|---|---|---|
| 78 | 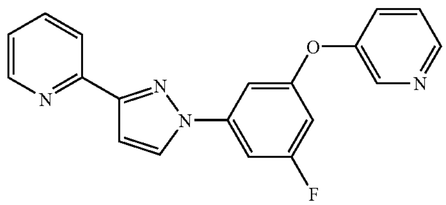 | 8.76 (s, 1H), 8.66 (dd, 2H), 8.06 (m, 2H), 7.93 (m, 1H), 7.88 (s, 1H), 7.64 (d, 1H), 7.51 (m, 1H), 7.26 (d, 1H), 7.20 (d, 1H), 7.00 (s, 1H), 6.87 (s, 1H). | MS 333.2 (M⁺ + H). |
| 79 | 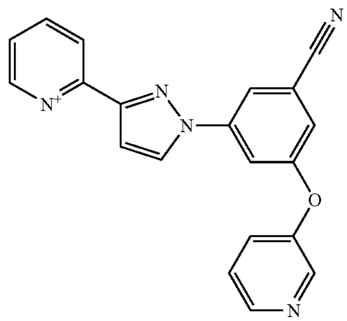 | 8.91 (d, 1H), 8.84 (d, 1H), 8.79 (d, 1H), 8.67 (d, 1H), 8.44 (m, 2H), 8.37 (t, 1H), 8.27 (s, 1H), 8.12 (d, 1H), 7.88 (m, 1H), 7.79 (t, 1H), 7.74 (s, 1H), 7.56 (s, 1H). | MS 340.0 (M⁺ + H). |
| 80 | 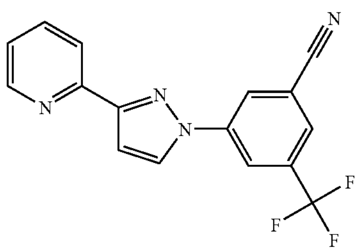 | 9.01 (s, 1H), 8.88 (s, 1H), 8.81 (d, 1H), 8.72 (d, 1H), 8.50 (d, 1H), 8.40 (t, 1H), 8.36 (s, 1H), 7.82 (t, 1H), 7.61 (s, 1H). | MS 315.3 (M⁺ + H). |
| 81 | 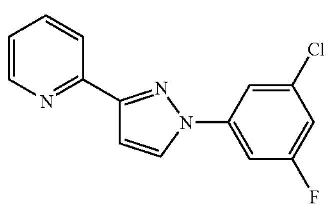 | 8.91 (s, 1H), 8.8s (s, 1H), 8.48 (m, 2H), 8.06 (s, 1H), 8.00 (d, 1H), 7.87 (s, 1H), 7.64 (s, 1H), 7.47 (d, 1H). | MS 273.9 (M⁺ + H). |
| 82 | 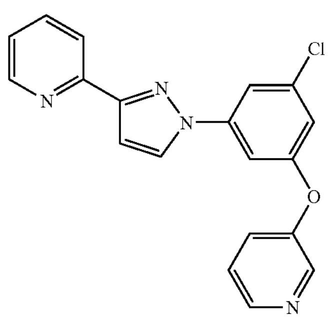 | 8.73 (d, 1H), 8.63 (d, 1H), 8.52 (d, 1H), 8.47 (d, 1H), 8.07 (d, 1H), 7.91 (m, 1H), 7.88 (m, 1H), 7.70 (m, 1H), 7.62 (m, 1H), 7.50 (m, 1H), 7.38 (s, 1H), 7.12 (m, 1H), 7.09 (m, 1H). | MS 349.0 (M⁺ + H). |
| 83 | 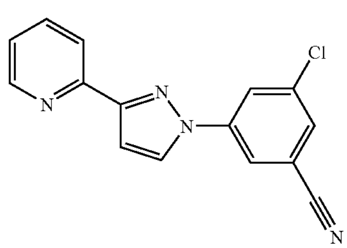 | 8.91 (s, 1H), 8.80 (d, 1H), 8.54 (s, 1H), 8.49 (m, 2H), 8.41 (t, 1H), 8.05 (s, 1H), 7.82 (t, 1H), 7.58 (t, 1H). | MS 280.9 (M⁺ + H). |

| EXAMPLE | Structure | ¹H NMR (δ) | MS (ESI) |
|---|---|---|---|
| 84 | 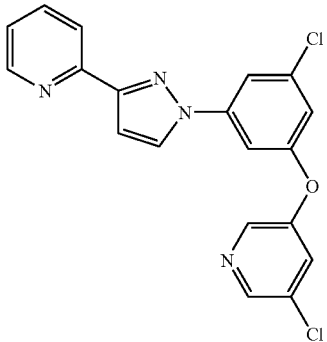 | 8.73 (d, 1H), 8.63 (d, 1H), 8.52 (s, 1H), 8.47 (d, 1H), 8.10 (m, 2H), 7.87 (m, 2H), 7.77 (s, 1H), 7.39 (t, 1H), 7.20 (s, 1H), 7.13 (d, 1H). | MS 383.0 (M⁺ + H). |
| 85 | 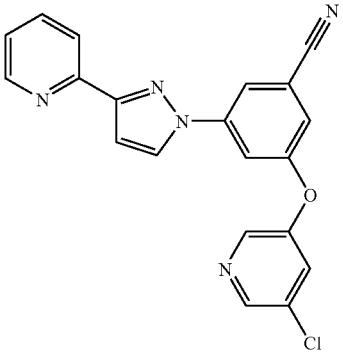 | 8.77 (br s, 1H), 8.64 (br s, 1H), 8.52 (br s, 2H), 8.32 (br s, 1H), 8.11 (br s, 2H), 7.90 (br s, 2H), 7.65 (br s, 1H), 7.40 (br s, 1H), 7.16 (br s, 1H). | MS 374.0 (M⁺ + H). |
| 86 | 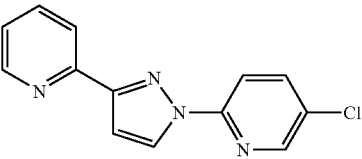 | 8.29 (d, 1H), 8.03 (d, 1H), 7.85 (dd, 1H), 7.72 (dt, 1H), 7.69 (d, 1H), 7.59 (d, 1H), 7.41 (d, 1H), 7.22 (dd, 1H), 6.67 (d, 1H) | MS 259.01 (M⁺ + H). |
| 87 | 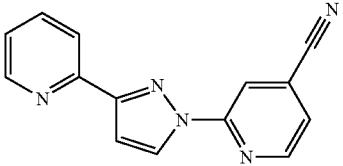 | 8.67 (m, 1H), 8.58 (d, 1H), 8.54 (d, 1H), 8.35 (s, 1H), 8.11 (d, 1H), 7.78 (m, 1H), 7.37 (m, 1H), 7.27 (m, 1H), 7.14 (d, 1H) | MS 249.12 (M⁺ + H). |
| 88 | 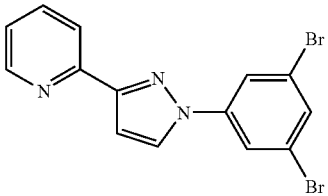 | 8.65 (d, 1H), 8.08 (d, 1H), 7.92 (d, 1H), 7.89 (s, 2H), 7.75 (m, 1H), 7.55 (s, 1H), 7.24 (m, 1H), 7.12 (d, 1H) | MS 377.93 (M⁺ + H). |
| 89 | 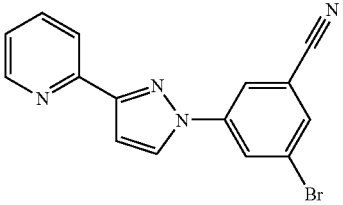 | 8.67 (m, 1H), 8.21 (m, 1H), 8.19 (d, 1H), 8.04 (s, 1H), 7.98 (d, 1H), 7.78 (m, 1H), 7.67 (s, 1H), 7.28 (m, 1H), 7.18 (d, 1H) | MS 324.88 (M⁺ + H). |

-continued

| EXAMPLE | Structure | $^1$H NMR (δ) | MS (ESI) |
|---|---|---|---|
| 90 | 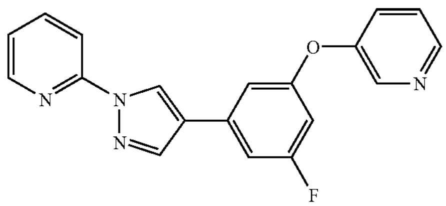 | 8.82 (s, 1H), 8.50-8.49 (d, 1H), 8.47-8.44 (m, 2H), 8.02-8.01 (d, 1H), 7.97 (s, 1H), 7.87-7.84 (m, 1H), 7.40-7.39 (m, 1H), 7.36-7.33 (m, 1H), 7.25-7.23 (m, 1H), 7.11-7.09 (m, 1H), 7.05 (s, 1H), 6.65-6.63 (m, 1H) | MS 333.1 (M$^+$ + H). |
| 91 | 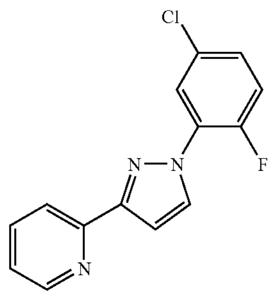 | 8.35 (d, 1H), 7.95 (m, 2H), 7.75 (d, 1H), 7.70 (dd, 1H), 7.55 (m, 1H), 7.35 (m, 2H), 7.10 (d, 1H). | MS 274.3 (M$^+$ + H). |
| 92 | 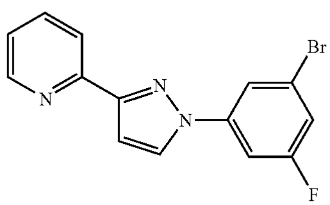 | 8.88 (d, 1H), 8.80 (d, 1H), 8.46 (d, 1H), 8.39 (m, 1H), 8.18 (s, 1H), 8.02 (d, 1H), 7.80 (t, 1H), 7.60 (d, 1H), 7.55 (s, 1H). | MS 317.9 (M$^+$ + H). |

Examples 93-281 have mGluR5 inhibitory activity <30% at 3 μM concentration in the calcium flux assay and/or inhibition <50% at 100 μM concentration in the PI assay.

| EXAMPLE | Structure | $^1$H NMR (δ) | MS (ESI) |
|---|---|---|---|
| 93. | 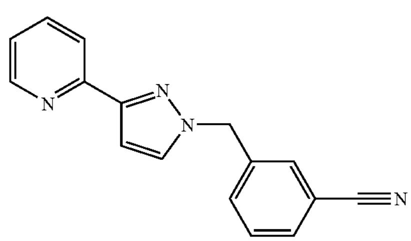 | 8.72 (d, 1H), 8.44 (m, 1H), 8.35 (d, 1H), 8.22 (s, 1H), 7.81 (m, 3H), 7.65 (m, 1H), 7.60 (m, 1H), 7.48 (s, 1H), 5.60 (s, 2H) | MS 260.7 (M$^+$ + H). |
| 94. | 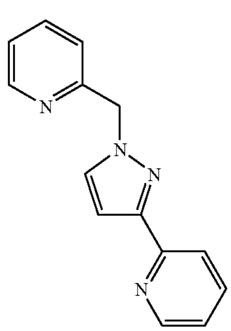 | 8.74 (m, 2H), 8.52 (m, 1H), 8.41 (m, 1H), 8.39 (s, 1H), 8.31 (m, 1H), 8.20 (m, 1H), 7.89 (m, 1H), 7.69 (m, 1H), 7.61 (s, 1H), 7.52 (d, 1H), 5.87 (s, 2H) | MS 237.1 (M$^+$ + H). |

-continued

| EXAMPLE | Structure | ¹H NMR (δ) | MS (ESI) |
|---|---|---|---|
| 95. | 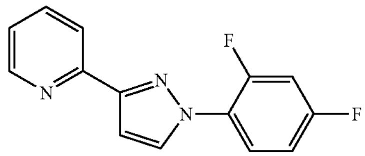 | 8.58 (d, 1H), 8.09 (t, 1H), 7.95 (d, 1H), 7.56 (m, 1H), 7.46 (m, 1H), 7.28 (m, 1H), 7.20 (d, 1H) | MS 257.2 (M⁺). |
| 96. | 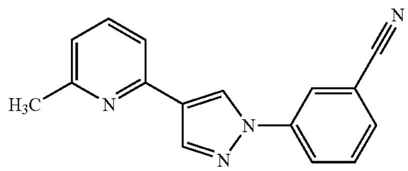 | 9.61 (m, 1H), 8.67 (s, 1H), 8.41 (s, 1H), 8.21-8.29 (m, 2H), 7.93 (m, 1H), 7.87 (m, 1H), 7.80 (m, 1H), 7.53 (m, 1H), 2.72 (s, 3H). | MS 261 (M⁺ + H). |
| 97. | 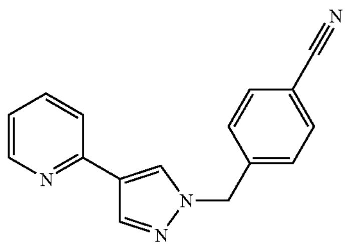 | 8.87 (s, 1H), 8.66 (m, 1H), 8.46 (s, 1H), 8.34 (m, 1H), 8.16 (m, 1H), 7.86 (m, 2H), 7.65 (m, 1H), 7.45 (m, 2H), 5.59 (s, 2H). | MS 261 (M⁺ + H). |
| 98. | 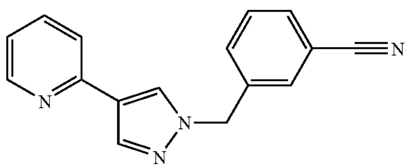 | 8.74 (m, 1H), 8.64 (m, 1H), 8.33 (s, 1H), 8.22 (m, 1H), 8.06 (m, 1H), 7.82 (m, 1H), 7.79 (s, 1H), 7.55-7.66 (m, 3H), 5.52 (s, 2H). | MS 261 (M⁺ + H). |
| 99. | 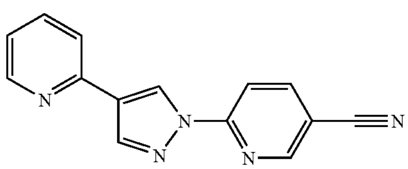 | 9.53 (s, 1H), 9.05 (s, 1H), 8.7 (s, 1H), 8.52-8.54 (d, 1H), 8.13-8.24 (m, 3H), 7.54-7.58 (m, 1H). | MS 248.1 (M⁺ + H). |
| 100. | 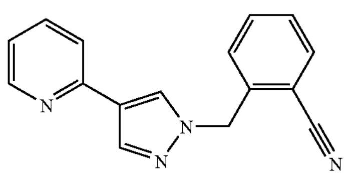 | 8.82 (m, 1H0, 8.68 (m, 1H), 8.42 (s, 1H), 8.31 (m, 1H), 8.14 (m, 1H), 7.92 (m, 1H), 7.71-7.75 (m, 1H), 7.54-7.65 (m, 2H), 7.41 (m, 1H) | MS 261 (M⁺ + H). |
| 101. | 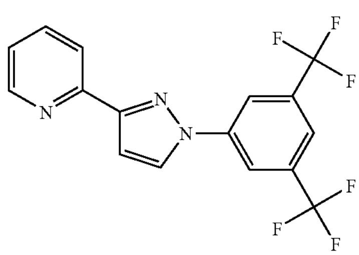 | 8.45 (d, 1H), 8.15 (s, 1H), 8.02 (m, 1H), 7.97 (s, 3H), 7.80 (d, 1H), 7.45 (m, 1H), 7.12 (s, 1H). | MS 358.3 (M⁺ + H). |
| 102. | 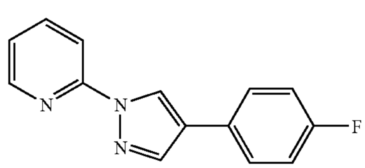 | 8.78 (s, 1H), 8.45-8.43 (m, 1H), 8.02-7.97 (m, 2H), 7.86-7.81 (m, 1H), 7.58-7.53 (m, 2H), 7.24-7.14 (M, 1H), 7.13-7.06 (m, 2H). | ND |

-continued

| EXAMPLE | Structure | ¹H NMR (δ) | MS (ESI) |
|---|---|---|---|
| 103. | 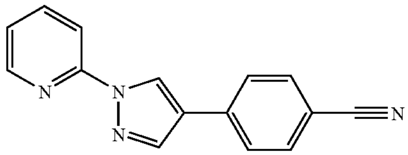 | 8.96 (s, 1H), 8.47-8.44 (m, 1H), 8.07-8.01 (m, 2H), 7.89-7.84 (m, 1H), 7.69 (s, 4H) 7.28-7.24 (m, 1H). | ND |
| 104. | 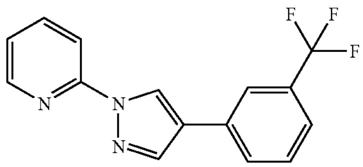 | 8.90 (d, 1H), 8.47-8.44 (m 1H), 8.05-8.01 (m, 2H), 7.89-7.83 (m, 2H), 7.79-7.75 (m, 1H), 7.54-7.52 (d, 2H), 7.26-7.21 (m, 1H). | ND |
| 105. | 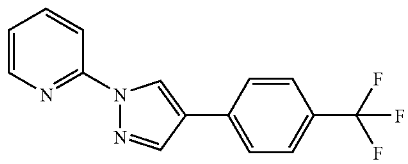 | 8.91 (d, 1H), 8.47-8.44 (m, 1H), 8.06-7.99 (m, 2H), 7.89-7.83 (m, 1H), 7.72-7.63 (m, 4H), 7.26-7.21 (m, 1H). | ND |
| 106. | 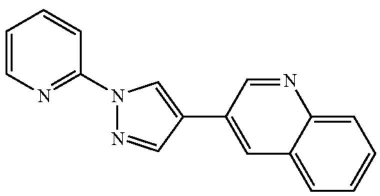 | 9.20-9.19 (m, 1H), 9.02 (s, 1H), 8.48-8.46 (m, 1H), 8.30-8.28 (m, 1H), 8.175 (s, 1H), 8.13-8.10 (d, 1H), 8.06-8.03 (d, 1H), 7.89-7.83 ND (m, 2H), 7.73-7.67 (m, 1H), 7.60-7.54 (m, 1H), 7.26-7.20 (m, 1H). | ND |
| 107. | 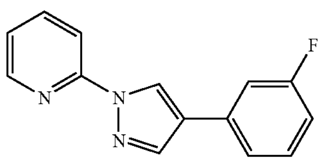 | 8.84 (d, 1H), 8.46-8.43 (m, 1H), 8.03-8.00 (m, 2H), 7.88-7.82 (m, 1H), 7.39-7.34 (m, 2H), 7.31-7.20 (m, 2H), 7.01-6.94 (m, 1H). | ND |
| 108. | 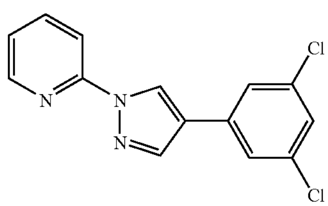 | 8.85 (d, 1H), 8.46-8.42 (m, 1H), 8.02-7.99 (m, 2H), 7.88-7.82 (m, 1H), 7.472-7.466 (d, 2H), 7.26-7.20 (m, 2H). | ND |
| 109. | 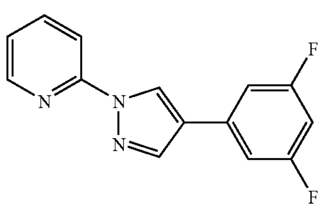 | 8.85 (d, 1H), 8.46-8.43 (m, 1H), 8.02-7.98 (m, 2H), 7.88-7.82 (m, 1H), 7.26-7.22 (m, 1H), 7.12-7.08 (m, 2H), 6.75-6.68 (m, 1H). | ND |
| 110. | 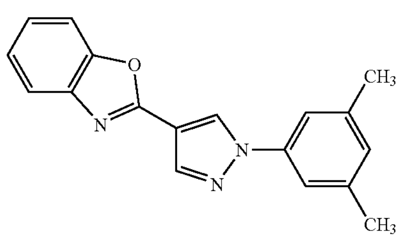 | ND | MS 290 (M⁺ + H). |

-continued

| EXAMPLE | Structure | ¹H NMR (δ) | MS (ESI) |
|---------|-----------|------------|----------|
| 111. | 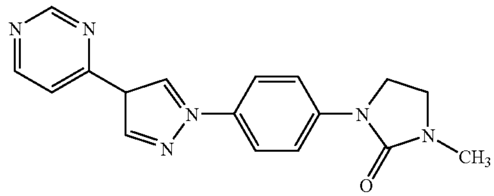 | ND | MS 321 (M⁺ + H). |
| 112. | 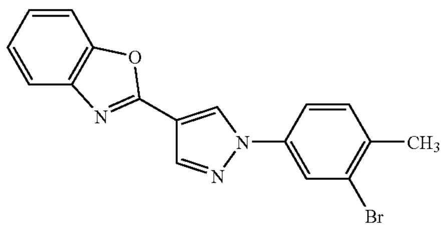 | ND | MS 354, 356 (M⁺ + H). |
| 113. | 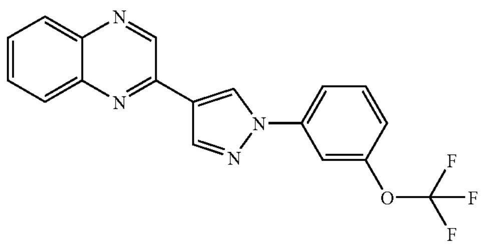 | ND | MS 357 (M⁺ + H). |
| 114. | 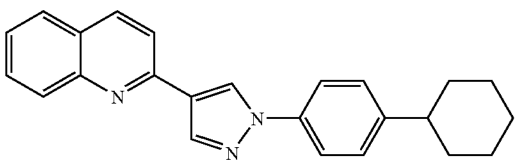 | ND | MS 354 (M⁺ + H). |
| 115. | 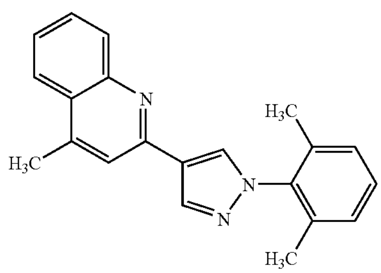 | ND | MS 314 (M⁺ + H). |
| 116. | 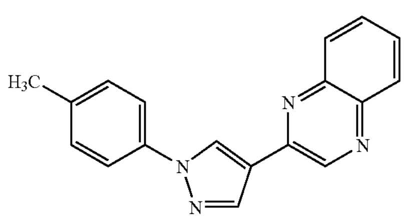 | ND | MS 287 (M⁺ + H). |
| 117. | 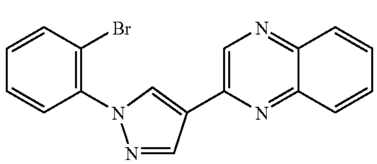 | ND | MS 352 (M⁺ + H). |

-continued

| EXAMPLE | Structure | ¹H NMR (δ) | MS (ESI) |
|---------|-----------|------------|----------|
| 118. | 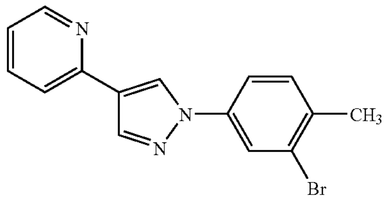 | ND | MS 314 316 (M⁺ + H). |
| 119. | 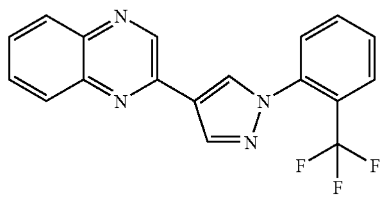 | ND | MS 341 (M⁺ + H). |
| 120. | 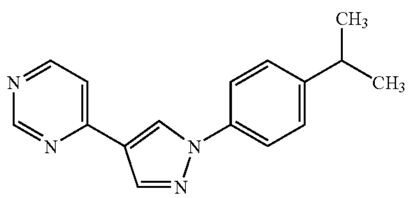 | ND | MS 265 (M⁺ + H). |
| 121. | 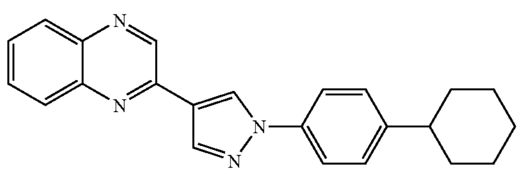 | ND | MS 355 (M⁺ + H). |
| 122. | 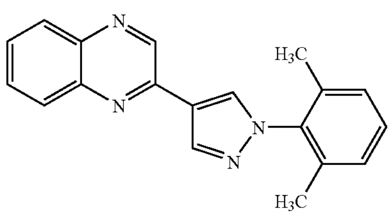 | ND | MS 301 (M⁺ + H). |
| 123. | 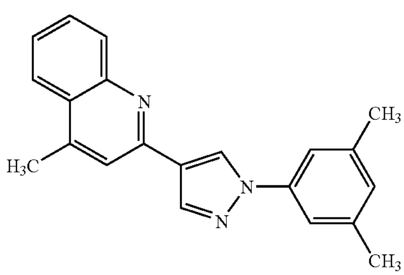 | ND | MS 314 (M⁺ + H). |
| 124. | 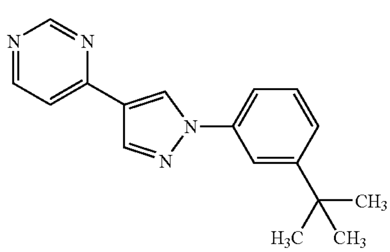 | ND | MS 279 (M⁺ + H). |

-continued
| EXAMPLE | Structure | ¹H NMR (δ) | MS (ESI) |
|---|---|---|---|
| 125. | 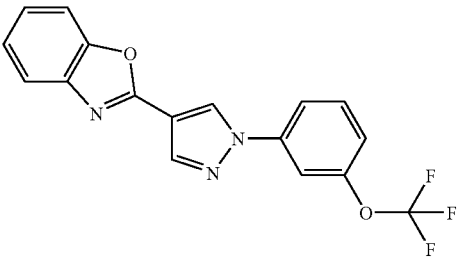 | ND | MS 346 (M⁺ + H). |
| 126. | 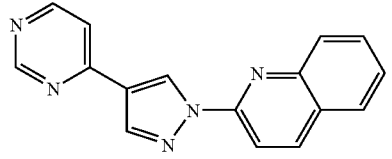 | ND | MS 274 (M⁺ + H). |
| 127. | 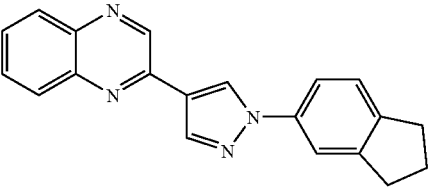 | ND | MS 313 (M⁺ + H). |
| 128. | 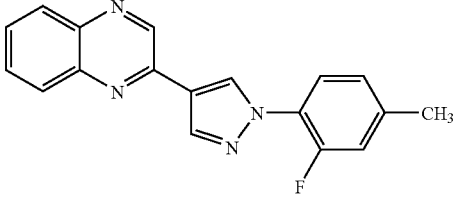 | ND | MS 305 (M⁺ + H). |
| 129. | 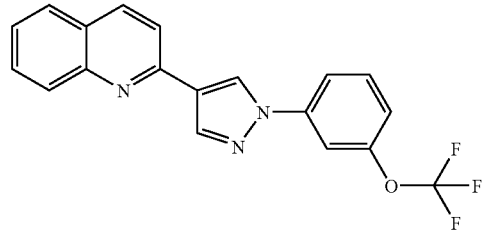 | ND | MS 356 (M⁺ + H). |
| 130. | 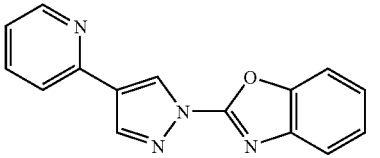 | ND | MS 263 (M⁺ + H). |
| 131. | 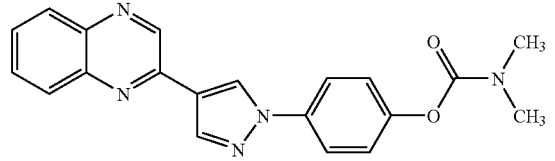 | ND | MS 360 (M⁺ + H). |

-continued

| EXAMPLE | Structure | ¹H NMR (δ) | MS (ESI) |
|---|---|---|---|
| 132. | 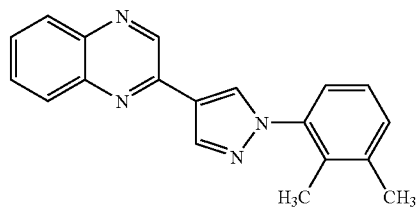 | ND | MS 301 (M⁺ + H). |
| 133. | 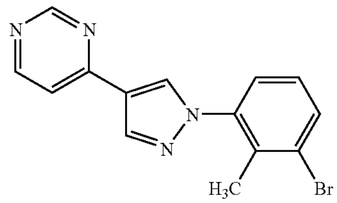 | ND | MS 315, 317 (M⁺ + H). |
| 134. | 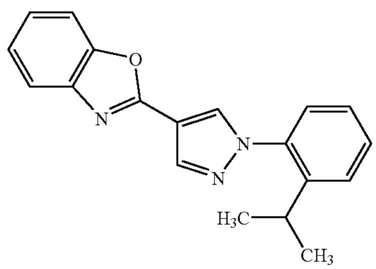 | ND | MS 304 (M⁺ + H). |
| 135. | 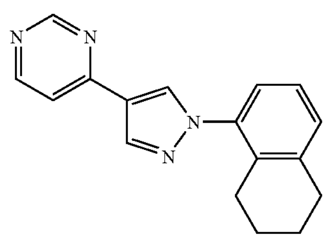 | ND | MS 277 (M⁺ + H). |
| 136. | 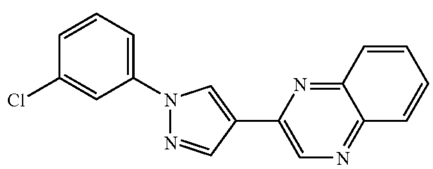 | ND | MS 307 (M⁺ + H). |
| 137. | 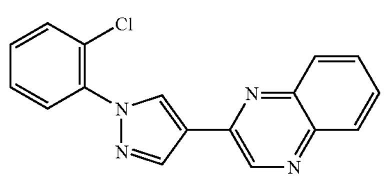 | ND | MS 307 (M⁺ + H). |
| 138. | 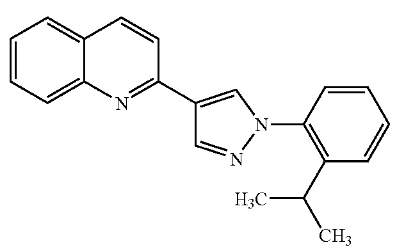 | ND | MS 314 (M⁺ + H). |

-continued

| EXAMPLE | Structure | ¹H NMR (δ) | MS (ESI) |
| --- | --- | --- | --- |
| 139. | 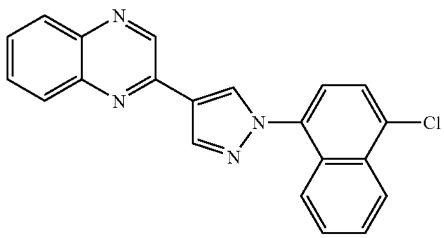 | ND | MS 357 (M⁺ + H). |
| 140. | 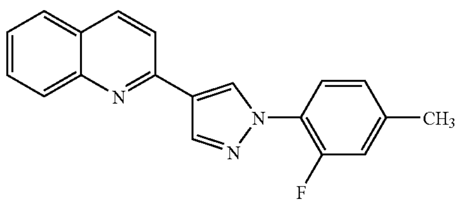 | ND | MS 304 (M⁺ + H). |
| 141. | 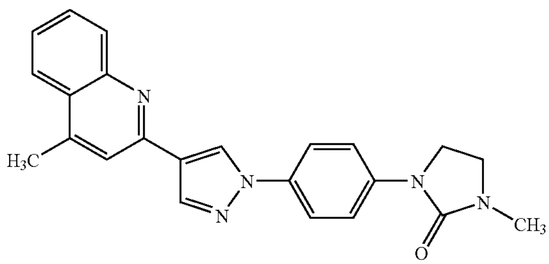 | ND | MS 384 (M⁺ + H). |
| 142. | 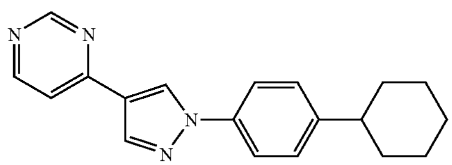 | ND | MS 305 (M⁺ + H). |
| 143. | 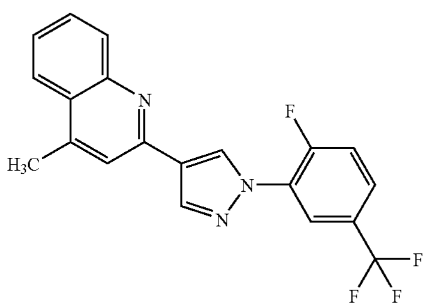 | ND | MS 372 (M⁺ + H). |
| 144. | 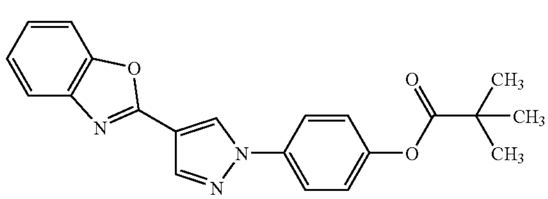 | ND | MS 362 (M⁺ + H). |
| 145. | 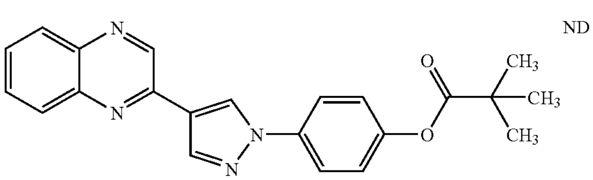 | ND | MS 373 (M⁺ + H). |

-continued
| EXAMPLE | Structure | ¹H NMR (δ) | MS (ESI) |
|---|---|---|---|
| 146. | 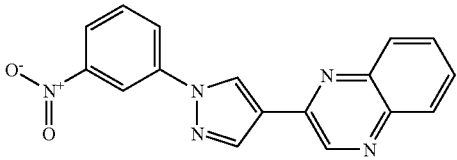 | ND | MS 318 (M⁺ + H). |
| 147. | 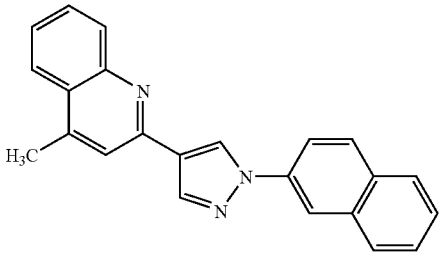 | ND | MS 336 (M⁺ + H). |
| 148. | 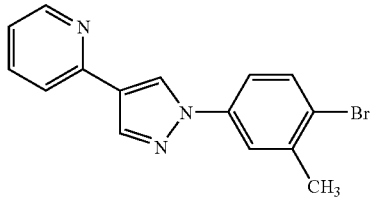 | ND | MS 314, 316 (M⁺ + H). |
| 149. | 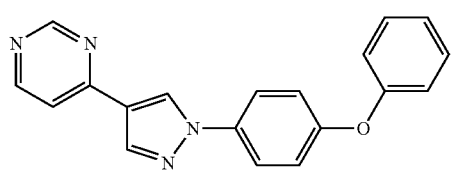 | ND | MS 315 (M⁺ + H). |
| 150. | 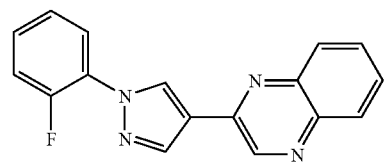 | ND | MS 291 (M⁺ + H). |
| 151. | 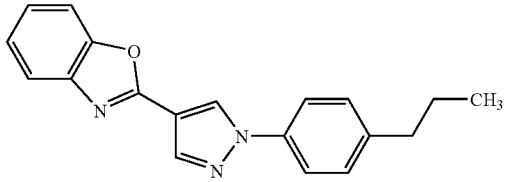 | ND | MS 304 (M⁺ + H). |
| 152. | 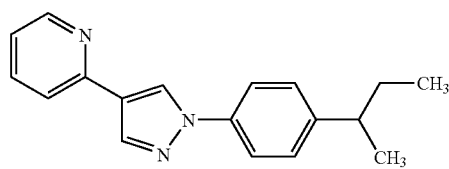 | ND | MS 278 (M⁺ + H). |

-continued

| EXAMPLE | Structure | ¹H NMR (δ) | MS (ESI) |
|---------|-----------|------------|----------|
| 153. | 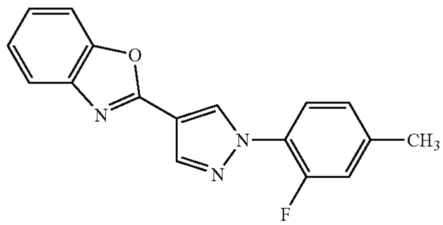 | ND | MS 294 (M⁺ + H). |
| 154. | 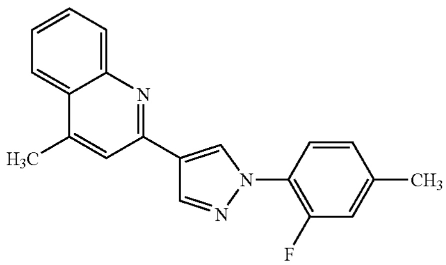 | ND | MS 318 (M⁺ + H). |
| 155. | 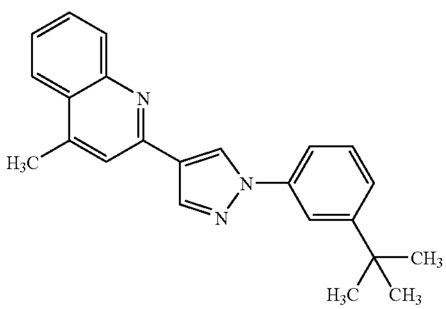 | ND | MS 342 (M⁺ + H). |
| 156. | 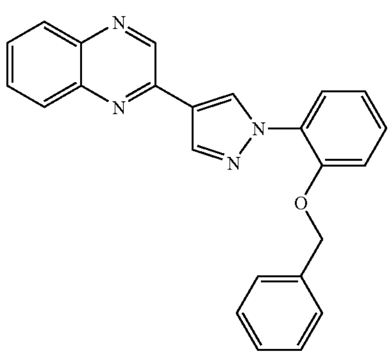 | ND | MS 379 (M⁺ + H). |
| 157. | 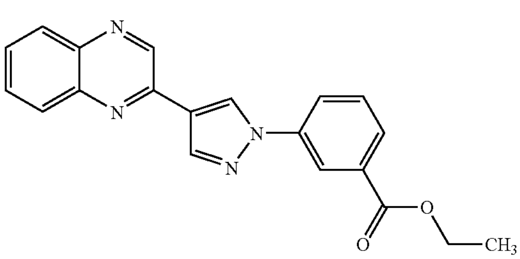 | ND | MS 345 (M⁺ + H). |

-continued
| EXAMPLE | Structure | ¹H NMR (δ) | MS (ESI) |
|---|---|---|---|
| 158. | 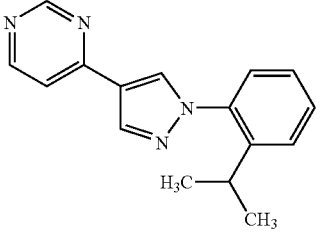 | ND | MS 265 (M⁺ + H). |
| 159. | 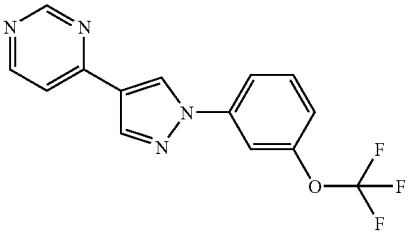 | ND | MS 307 (M⁺ + H). |
| 160. | 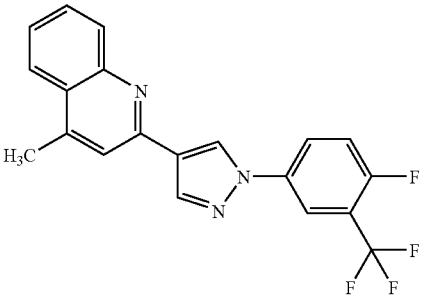 | ND | MS 372 (M⁺ + H). |
| 161. | 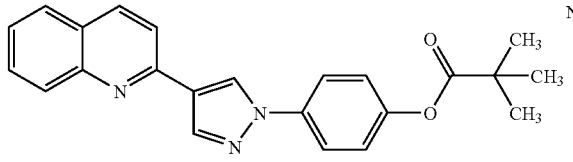 | ND | MS 372 (M⁺ + H). |
| 162. | 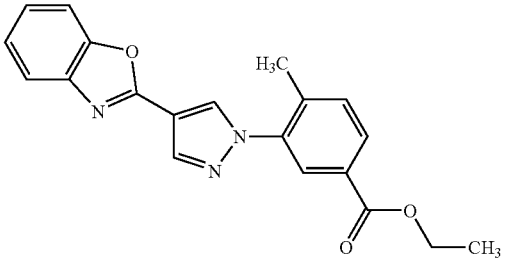 | ND | MS 348 (M⁺ + H). |
| 163. | 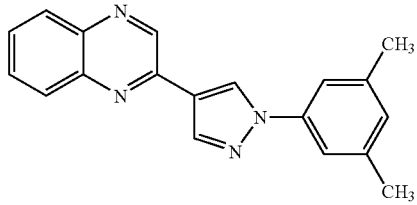 | ND | MS 301 (M⁺ + H). |

-continued
| EXAMPLE | Structure | ¹H NMR (δ) | MS (ESI) |
|---|---|---|---|
| 164. | 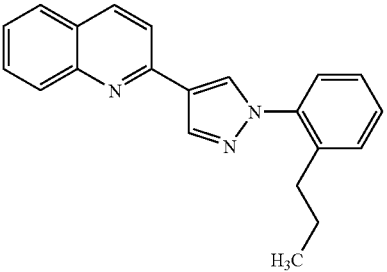 | ND | MS 314 (M⁺ + H). |
| 165. | 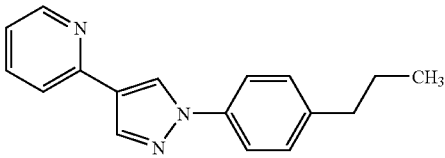 | ND | MS 264 (M⁺ + H). |
| 166. | 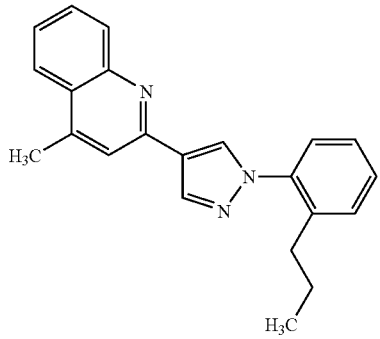 | ND | MS 328 (M⁺ + H). |
| 167. | 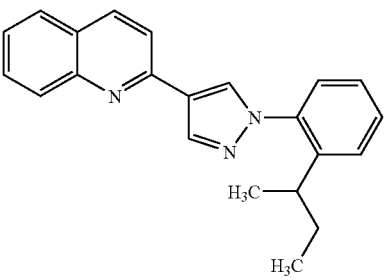 | ND | MS 328 (M⁺ + H). |
| 168. | 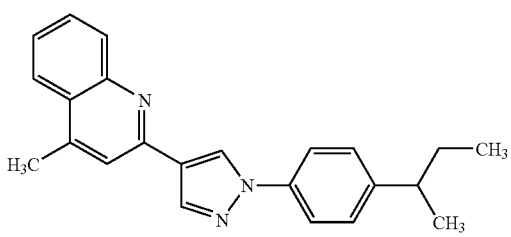 | ND | MS 342 (M⁺ + H). |
| 169. | 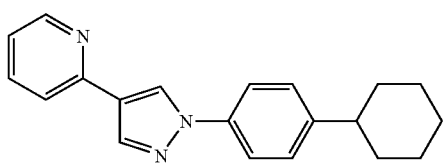 | ND | MS 304 (M⁺ + H). |

-continued

| EXAMPLE | Structure | ¹H NMR (δ) | MS (ESI) |
|---|---|---|---|
| 170. | 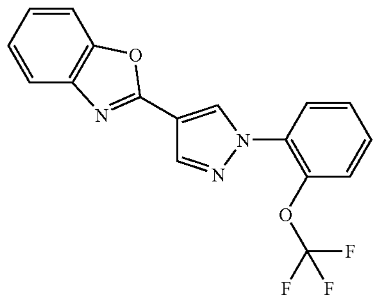 | ND | MS 346 (M⁺ + H). |
| 171. | 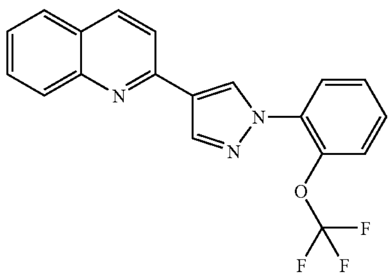 | ND | MS 356 (M⁺ + H). |
| 172. | 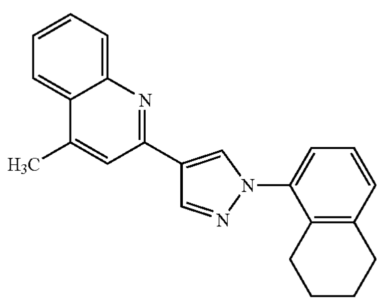 | ND | MS 340 (M⁺ + H). |
| 173. | 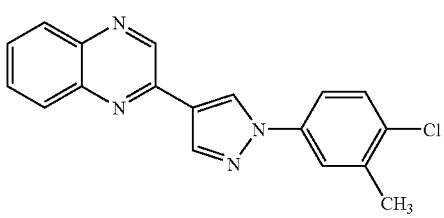 | ND | MS 321 (M⁺ + H). |
| 174. | 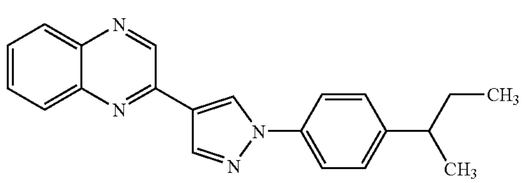 | ND | MS 329 (M⁺ + H). |
| 175. | 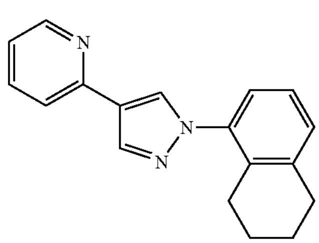 | ND | MS 276 (M⁺ + H). |

-continued

| EXAMPLE | Structure | ¹H NMR (δ) | MS (ESI) |
|---|---|---|---|
| 176. | 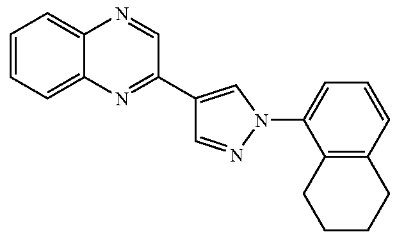 | ND | MS 327 (M⁺ + H). |
| 177. | 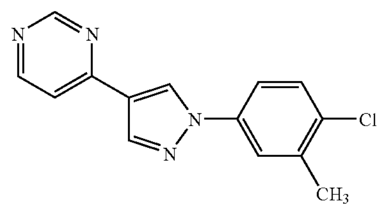 | ND | MS 271 (M⁺ + H). |
| 178. | 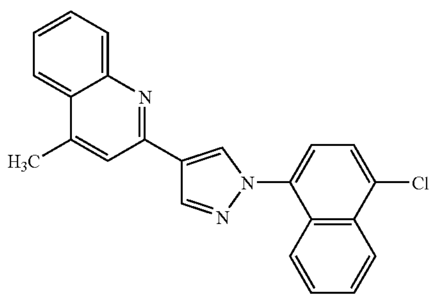 | ND | MS 370 (M⁺ + H). |
| 179. | 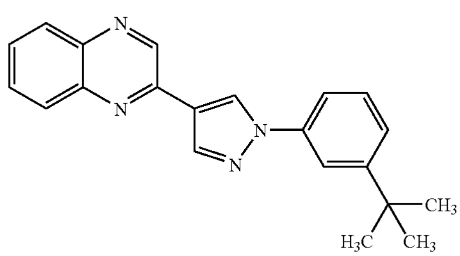 | ND | MS 329 (M⁺ + H). |
| 180. | 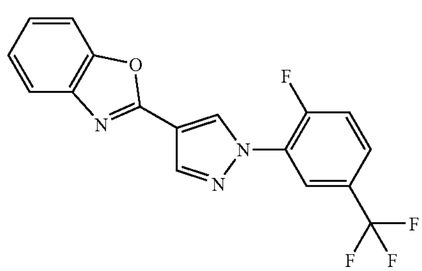 | ND | MS 348 (M⁺ + H). |
| 181. | 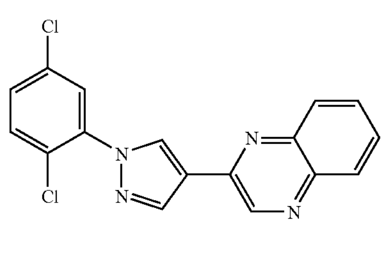 | ND | MS 341 (M⁺ + H). |

-continued

| EXAMPLE | Structure | ¹H NMR (δ) | MS (ESI) |
| --- | --- | --- | --- |
| 182. | 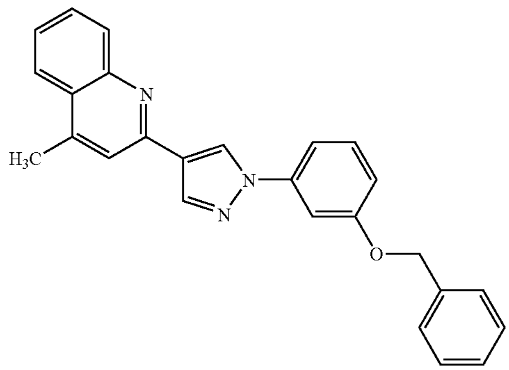 | ND | MS 392 (M⁺ + H). |
| 183. | 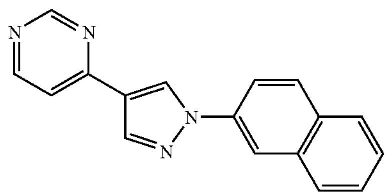 | ND | MS 273 (M⁺ + H). |
| 184. | 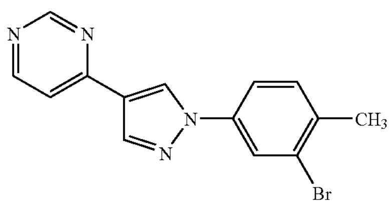 | ND | MS 315, 317 (M⁺ + H). |
| 185. | 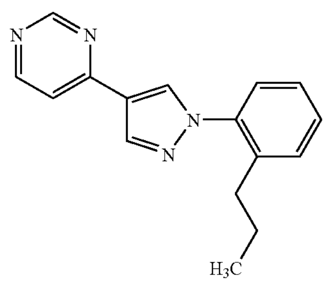 | ND | MS 265 (M⁺ + H). |
| 186. | 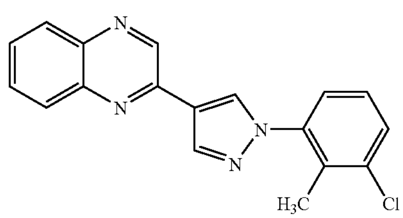 | ND | MS 321 (M⁺ + H). |
| 187. | 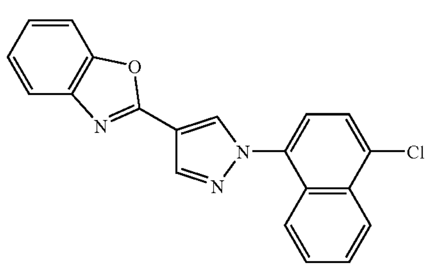 | ND | MS 346 (M⁺ + H). |

-continued

| EXAMPLE | Structure | ¹H NMR (δ) | MS (ESI) |
|---|---|---|---|
| 188. | 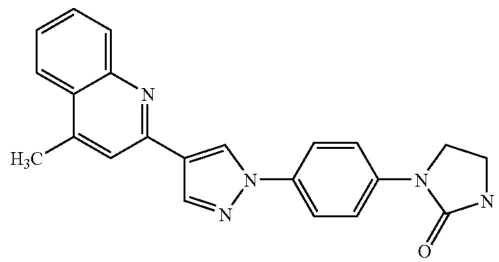 | ND | MS 370 (M⁺ + H). |
| 189. | 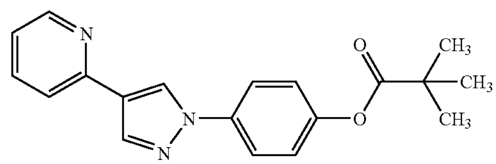 | ND | MS 322 (M⁺ + H). |
| 190. | 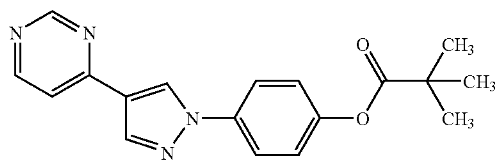 | ND | MS 323 (M⁺ + H). |
| 191. | 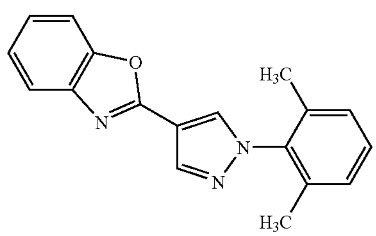 | ND | MS 290 (M⁺ + H). |
| 192. | 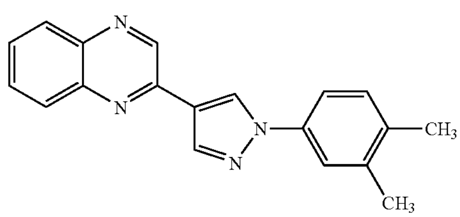 | ND | MS 301 (M⁺ + H). |
| 193. | 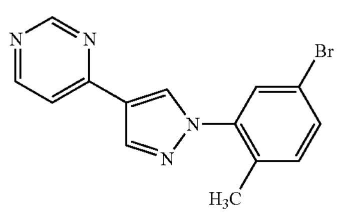 | ND | MS 315, 317 (M⁺ + H). |
| 194. | 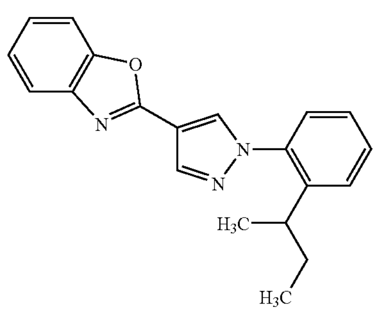 | ND | MS 318 (M⁺ + H). |

-continued

| EXAMPLE | Structure | ¹H NMR (δ) | MS (ESI) |
|---------|-----------|------------|----------|
| 195. | 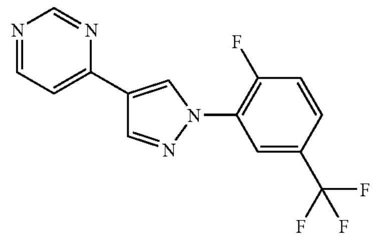 | ND | MS 309 (M⁺ + H). |
| 196. | 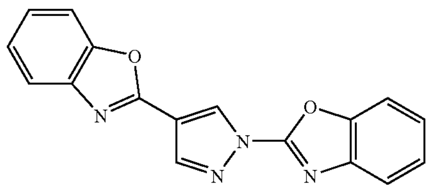 | ND | MS 303 (M⁺ + H). |
| 197. | 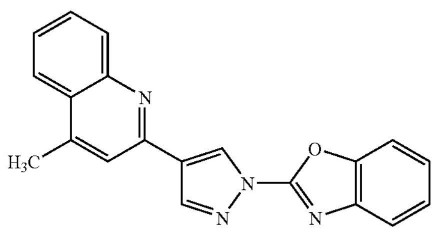 | ND | MS 327 (M⁺ + H). |
| 198. | 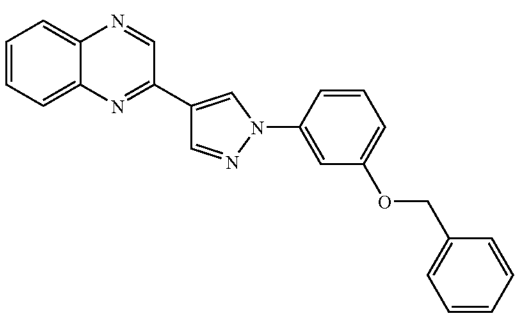 | ND | MS 379 (M⁺ + H). |
| 199. | 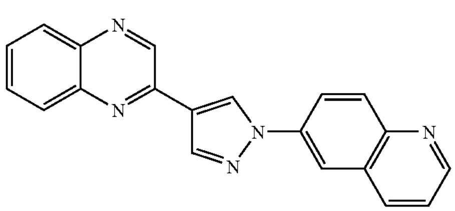 | ND | MS 324 (M⁺ + H). |
| 200. | 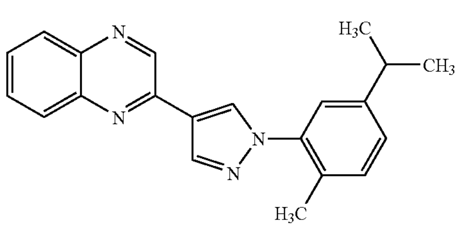 | ND | MS 329 (M⁺ + H). |

-continued

| EXAMPLE | Structure | ¹H NMR (δ) | MS (ESI) |
|---|---|---|---|
| 201. | 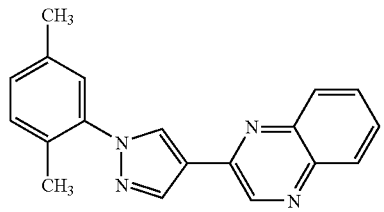 | ND | MS 301 (M⁺ + H). |
| 202. | 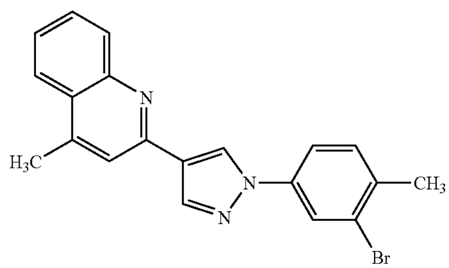 | ND | MS 378, 380 (M⁺ + H). |
| 203. | 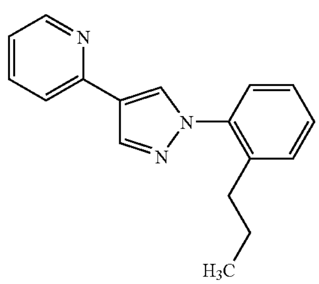 | ND | MS 264 (M⁺ + H). |
| 204. | 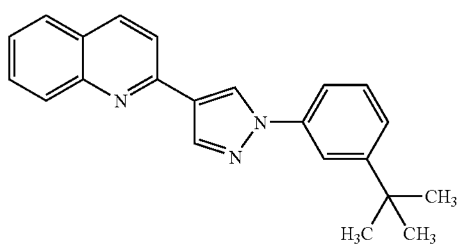 | ND | MS 328 (M⁺ + H). |
| 205. | 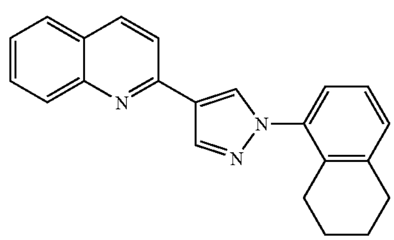 | ND | MS 326 (M⁺ + H). |
| 206. | 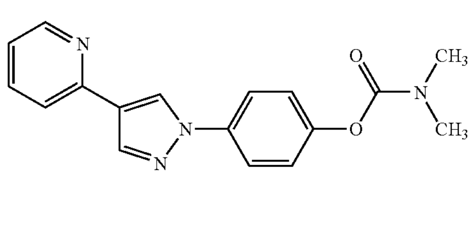 | ND | MS 309 (M⁺ + H). |

-continued

| EXAMPLE | Structure | ¹H NMR (δ) | MS (ESI) |
|---|---|---|---|
| 207. | 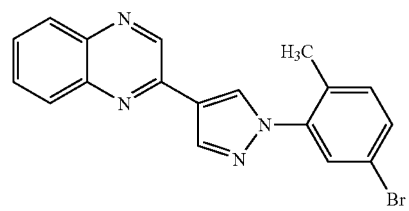 | ND | MS 366 (M⁺ + H). |
| 208. | 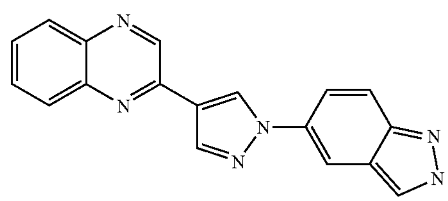 | ND | MS 313 (M⁺ + H). |
| 209. | 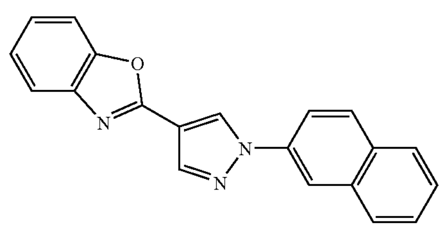 | ND | MS 312 (M⁺ + H). |
| 210. | 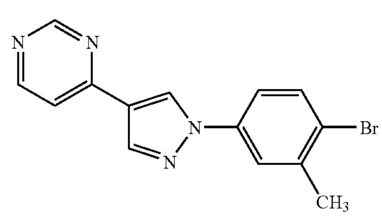 | ND | MS 3145 317 (M⁺ + H). |
| 211. | 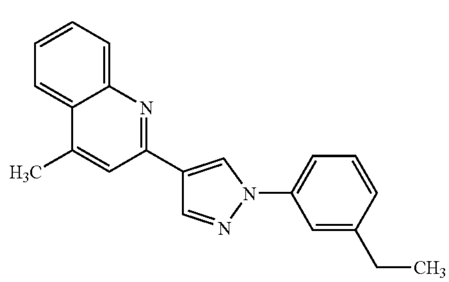 | ND | MS 314 (M⁺ + H). |
| 212. | 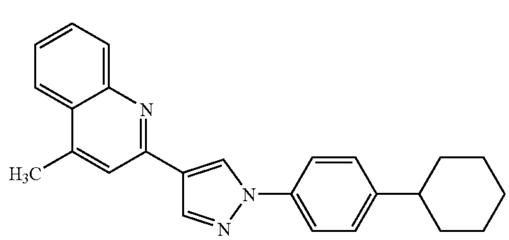 | ND | MS 368 (M⁺ + H). |

-continued

| EXAMPLE | Structure | ¹H NMR (δ) | MS (ESI) |
| --- | --- | --- | --- |
| 213. | 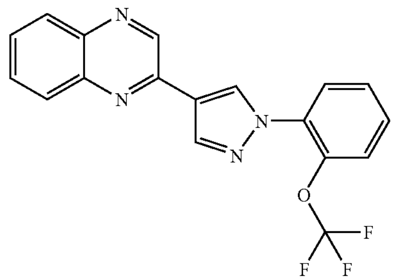 | ND | MS 357 (M⁺ + H). |
| 214. | 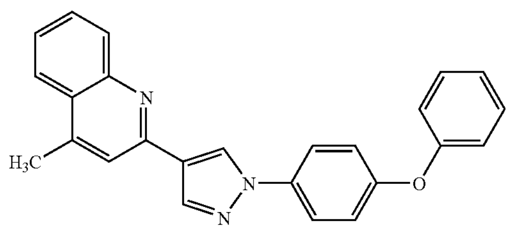 | ND | MS 378 (M⁺ + H). |
| 215. | 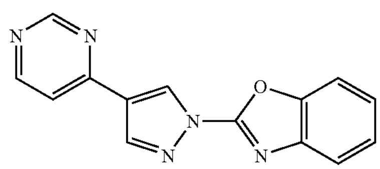 | ND | MS 264 (M⁺ + H). |
| 216. | 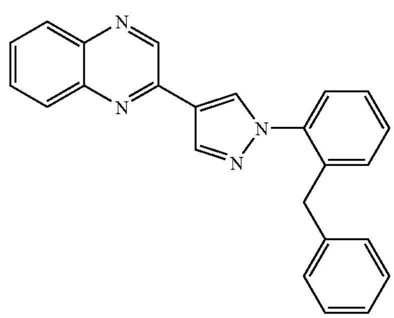 | ND | MS 363 (M⁺ + H). |
| 217. | 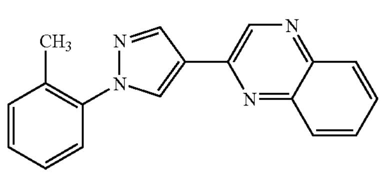 | ND | MS 287 (M⁺ + H). |
| 218. | 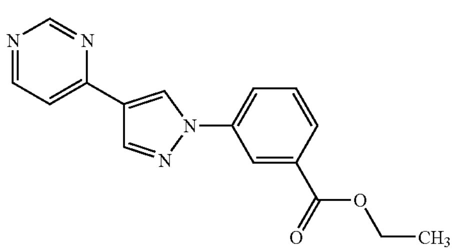 | ND | MS 295 (M⁺ + H). |

-continued

| EXAMPLE | Structure | ¹H NMR (δ) | MS (ESI) |
|---|---|---|---|
| 219. | 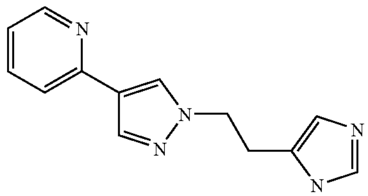 | ND | MS 240 (M⁺ + H). |
| 220. | 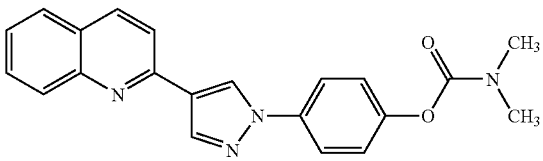 | ND | MS 359 (M⁺ + H). |
| 221. | 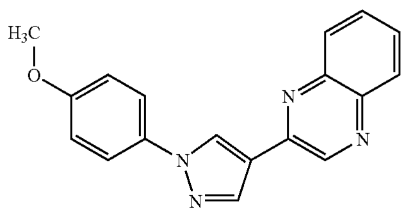 | ND | MS 303 (M⁺ + H). |
| 222. | 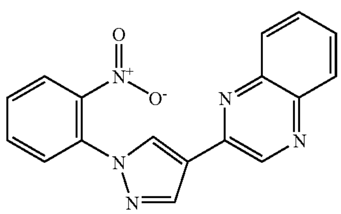 | ND | MS 318 (M⁺ + H). |
| 223. | 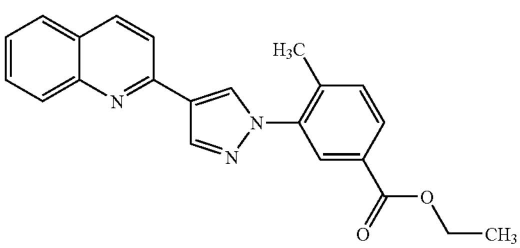 | ND | MS 358 (M⁺ + H). |
| 224. | 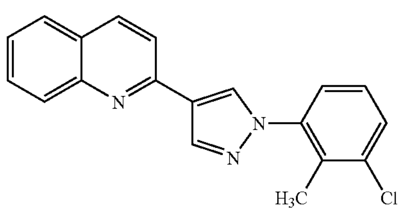 | ND | MS 320 (M⁺ + H). |
| 225. | 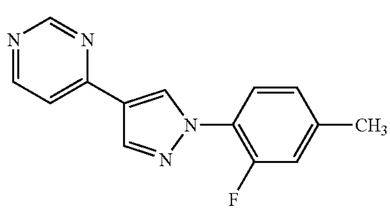 | ND | MS 255 (M⁺ + H). |

-continued

| EXAMPLE | Structure | ¹H NMR (δ) | MS (ESI) |
|---------|-----------|------------|----------|
| 226. | 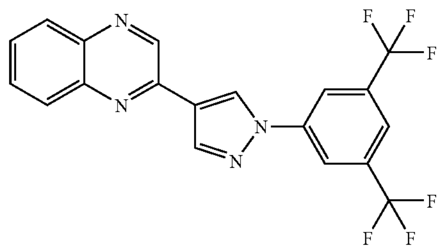 | ND | MS 409 (M⁺ + H). |
| 227. | 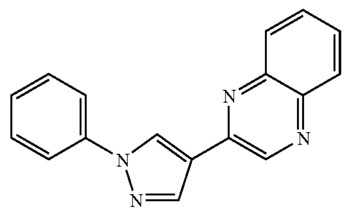 | ND | MS 273 (M⁺ + H). |
| 228. | 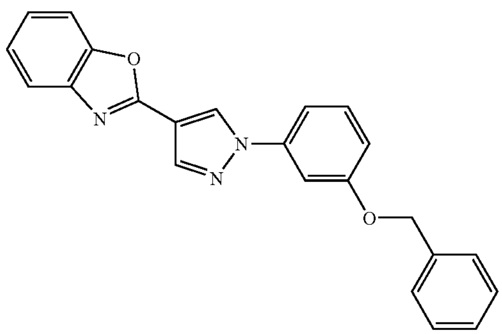 | ND | MS 368 (M⁺ + H). |
| 229. | 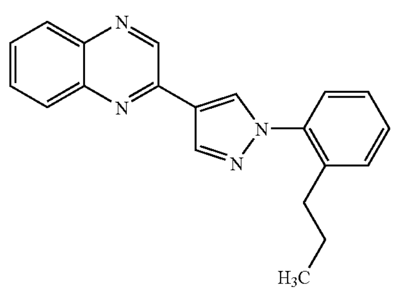 | ND | MS 315 (M⁺ + H). |
| 230. | 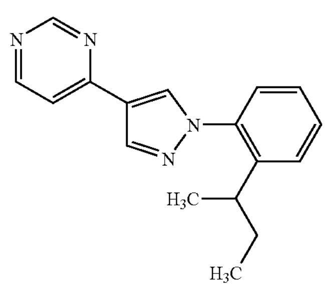 | ND | MS 279 (M⁺ + H). |
| 231. | 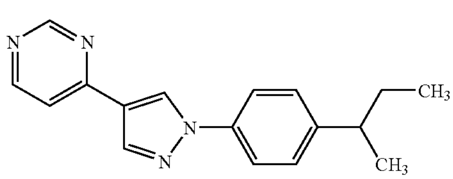 | ND | MS 279 (M⁺ + H). |

| EXAMPLE | Structure | ¹H NMR (δ) | MS (ESI) |
|---|---|---|---|
| 232. | 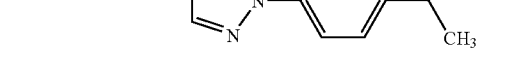 | ND | MS 328 (M⁺ + H). |
| 233. | 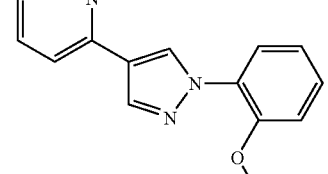 | ND | MS 306 (M⁺ + H). |
| 234. | 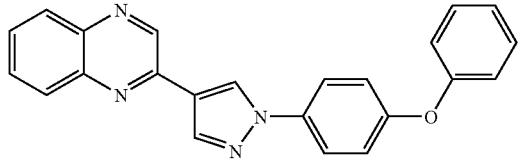 | ND | MS 365 (M⁺ + H). |
| 235. | 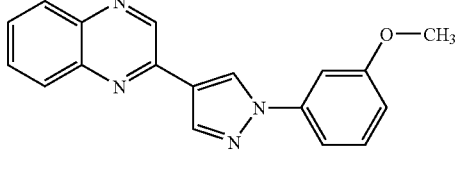 | ND | MS 303 (M⁺ + H). |
| 236. | 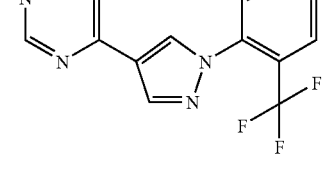 | ND | MS 291 (M⁺ + H). |
| 237. | 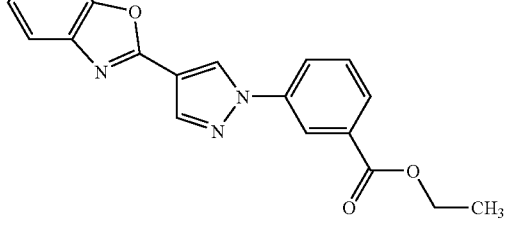 | ND | MS 334 (M⁺ + H). |
| 238. | 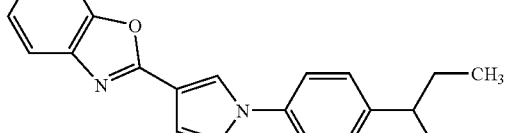 | ND | MS 318 (M⁺ + H). |

-continued

| EXAMPLE | Structure | ¹H NMR (δ) | MS (ESI) |
| --- | --- | --- | --- |
| 239. | 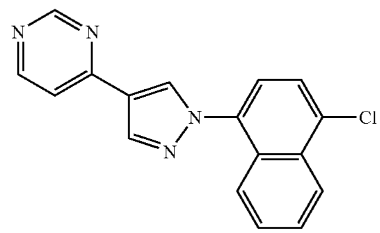 | ND | MS 307 (M⁺ + H). |
| 240. | 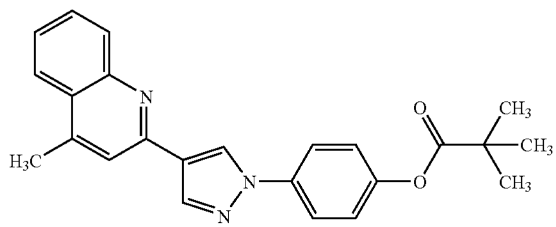 | ND | MS 386 (M⁺ + H). |
| 241. | 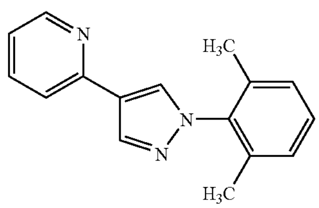 | ND | MS 250 (M⁺ + H). |
| 242. | 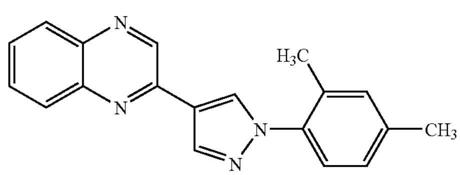 | ND | MS 301 (M⁺ + H). |
| 243. | 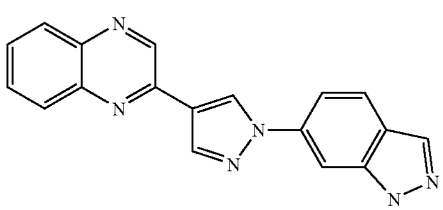 | ND | MS 313 (M⁺ + H). |
| 244. | 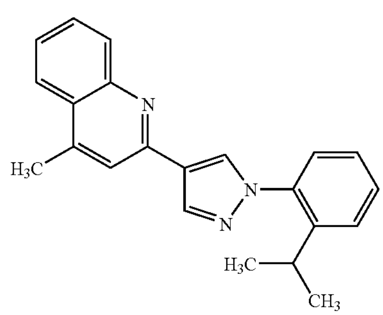 | ND | MS 328 (M⁺ + H). |

-continued
| EXAMPLE | Structure | ¹H NMR (δ) | MS (ESI) |
|---|---|---|---|
| 245. | 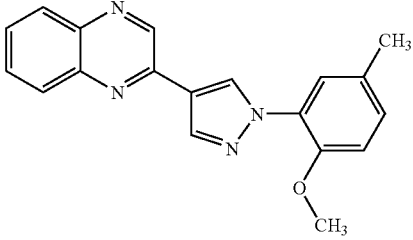 | ND | MS 317 (M⁺ + H). |
| 246. | 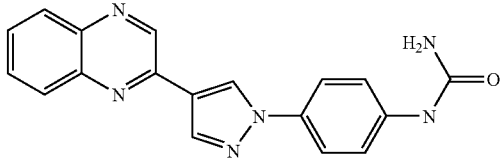 | ND | MS 330 (M⁺ + H). |
| 247. | 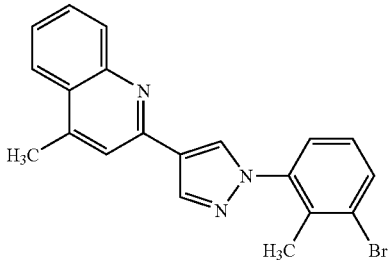 | ND | MS 379 (M⁺ + H). |
| 248. | 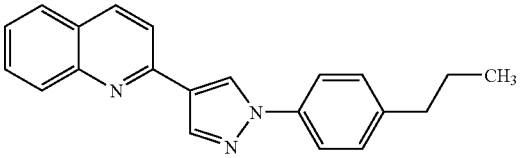 | ND | MS 314 (M⁺ + H). |
| 249. | 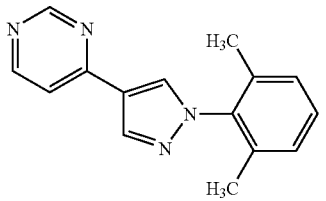 | ND | MS 251 (M⁺ + H). |
| 250. | 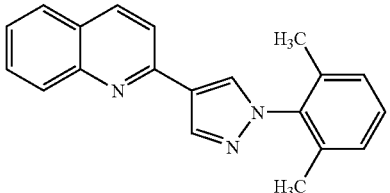 | ND | MS 300 (M⁺ + H). |
| 251. | 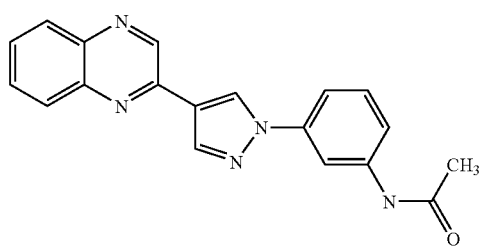 | ND | MS 330 (M⁺ + H). |

-continued

| EXAMPLE | Structure | ¹H NMR (δ) | MS (ESI) |
|---|---|---|---|
| 252. | 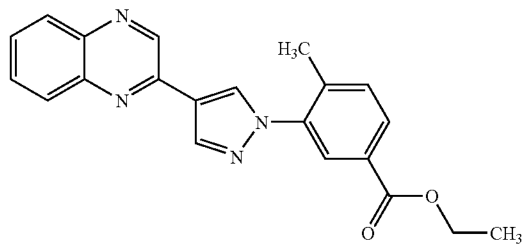 | ND | MS 359 (M⁺ + H). |
| 253. | 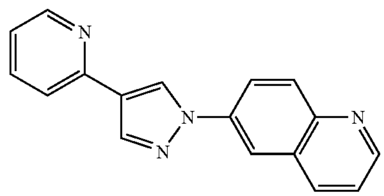 | ND | MS 273 (M⁺ + H). |
| 254. | 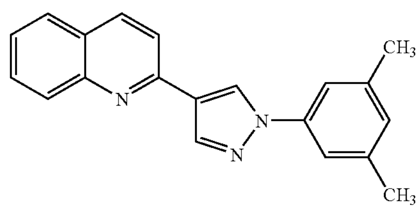 | ND | MS 300 (M⁺ + H). |
| 255. | 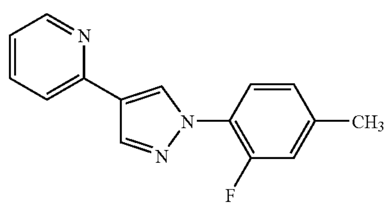 | ND | MS 254 (M⁺ + H). |
| 256. | 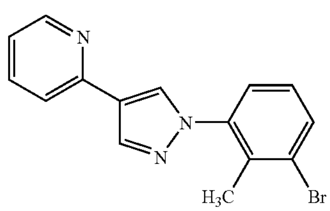 | ND | MS 314, 316 (M⁺ + H). |
| 257. | 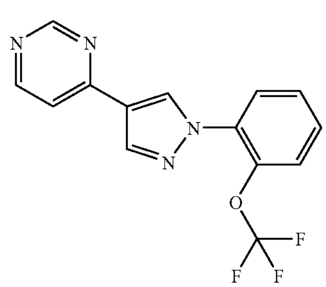 | ND | MS 307 (M⁺ + H). |
| 258. | 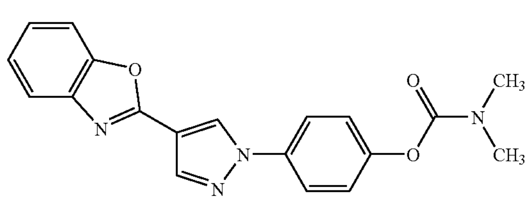 | ND | MS 349 (M⁺ + H). |

-continued

| EXAMPLE | Structure | ¹H NMR (δ) | MS (ESI) |
|---|---|---|---|
| 259. | 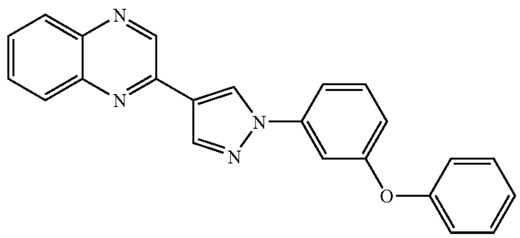 | ND | MS 365 (M⁺ + H). |
| 260. | 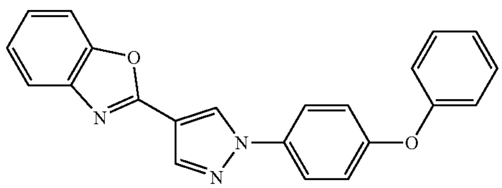 | ND | MS 354 (M⁺ + H). |
| 261. | 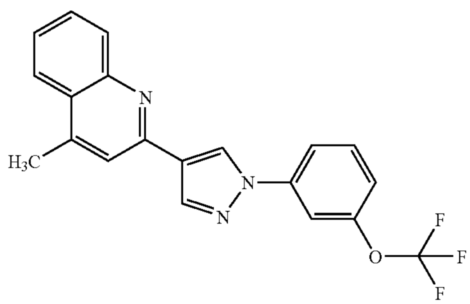 | ND | MS 370 (M⁺ + H). |
| 262. | 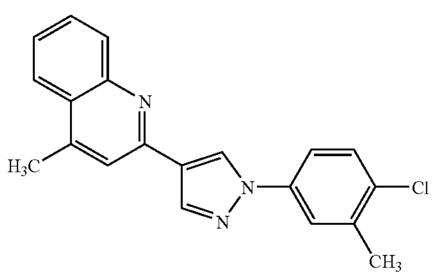 | ND | MS 334 (M⁺ + H). |
| 263. | 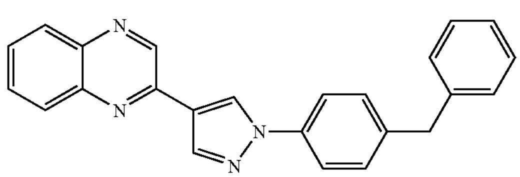 | ND | MS 363 (M⁺ + H). |
| 264. | 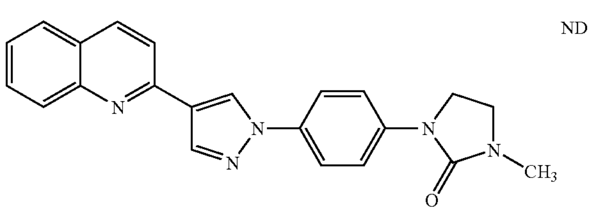 | ND | MS 370 (M⁺ + H). |

| EXAMPLE | Structure | ¹H NMR (δ) | MS (ESI) |
|---|---|---|---|
| 265. | 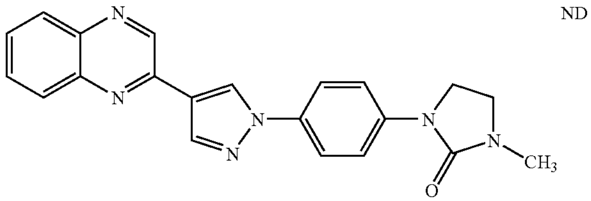 | ND | MS 371 (M⁺ + H). |
| 266. | 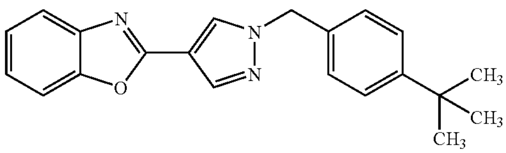 | ND | MS 332 (M⁺ + H). |
| 267. | 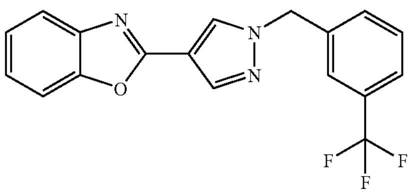 | ND | MS 344 (M⁺ + H). |
| 268. | 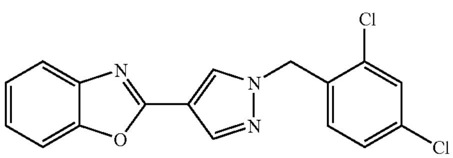 | ND | MS 344 (M⁺ + H). |
| 269. | 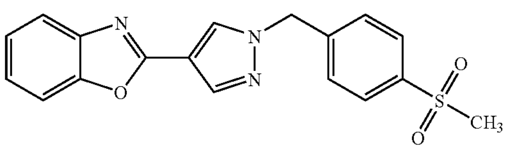 | ND | MS 354 (M⁺ + H). |
| 270. | 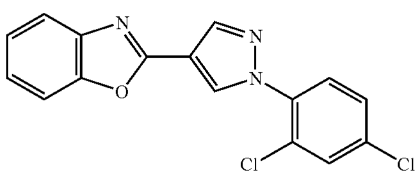 | ND | MS 330 (M⁺ + H). |
| 271. | 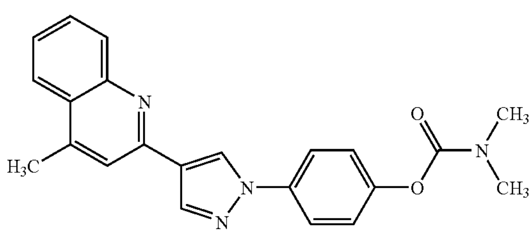 | ND | MS 373 (M⁺ + H). |
| 272. | 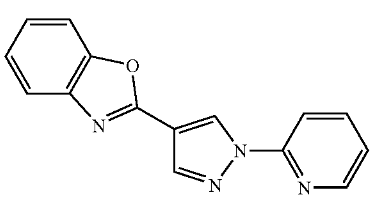 | ND | MS 263 (M⁺ + H). |

| EXAMPLE | Structure | ¹H NMR (δ) | MS (ESI) |
|---|---|---|---|
| 273. | 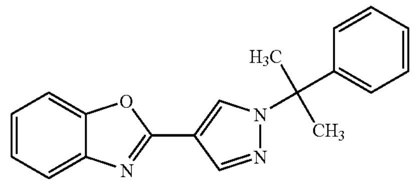 | ND | MS 304 (M⁺ + H). |
| 274. | 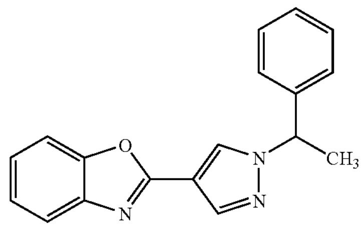 | ND | MS 290 (M⁺ + H). |
| 275. | 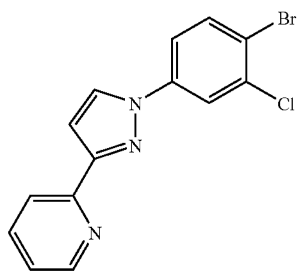 | 8.55 (d, 1H), 7.95 (m, 1H), 7.85 (d, 1H), 7.80 (d, 1H), 7.65 (d, 1H), 7.60 (s, 1H), 7.45 (m, 1H), 7.20 (dd, 1H), 7.00 (d, 1H). | MS 336.0 (M⁺ + H). |
| 276. | 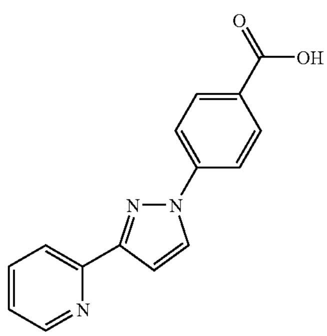 | 8.55 (d, 1H), 8.00 (d, 2H), 7.95 (m, 2H), 7.60 (d, 1H), 7.40 (m, 3H), 7.10 (d, 1H). | MS 266.1 (M⁺ + H). |
| 277. | 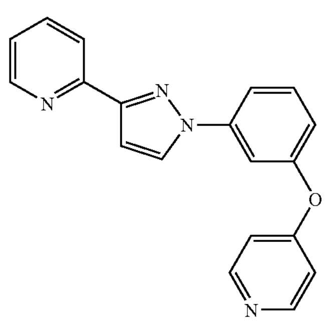 | 8.85 (d, 2H), 8.60 (d, 1H), 7.95 (t, 1H), 7.85 (s, 1H), 7.65 (m, 2H), 7.45 (m, 5H), 7.25 (s, 1H), 6.95 (s, 1H). | MS 315.1 (M⁺ + H). |
| 278. | 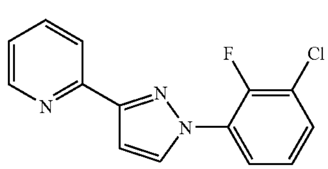 | 8.40 (d, 1H), 7.90 (m, 2H), 7.80 (d, 1H), 7.70 (t, 1H), 7.50 (t, 1H), 7.30 (m, 2H), 7.10 (s, 1H). | MS 275.1 (M⁺ + H). |

| EXAMPLE | Structure | ¹H NMR (δ) | MS (ESI) |
|---|---|---|---|
| 279. | 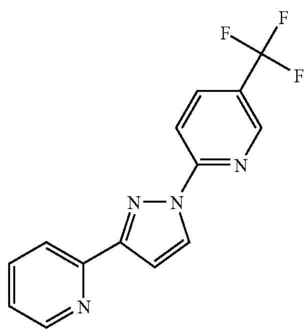 | 8.60 (s, 1H), 8.40 (m, 2H), 7.95 (d, 1H), 7.90 (d, 1H), 7.85 (t, 1H), 7.65 (d, 1H), 7.35 (m, 1H), 6.95 (d, 1H). | MS 291.3 (M⁺ + H). |
| 280. | 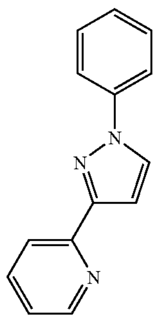 | 8.60 (d, 1H), 7.99 (t, 1H), 7.85 (s, 1H), 7.47 (t, 1H), 7.42 (m, 4H), 7.39 (d, 2H), 6.99 (s, 1H). | MS 222.0 (M⁺ + H). |
| 281. | 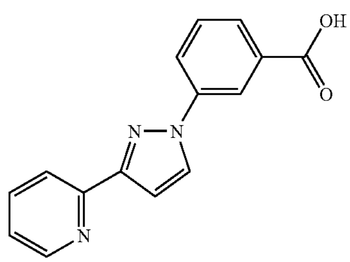 | 8.45 (d, 1H), 7.90 (m, 1H), 7.86 (m, 1H), 7.83 (d, 1H), 7.78 (m, 1H), 7.57 (d, 1H), 7.50 (m, 2H), 7.37 (m, 1H), 6.93 (m, 1H). | MS 267.0 (M⁺ + H). |
| 282. | 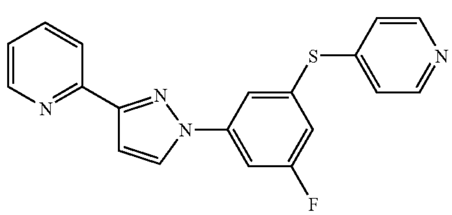 | 8.68 (d, 2H), 8.54 (d, 1H), 7.95 (m, 1H), 7.90 (s, 1H), 7.72 (d, 2H), 7.61 (m, 3H), 7.40 (m, 1H), 7.37 (s, 1H), 7.02 (s, 1H). | MS 349.0 (M⁺ + H). |
| 283. | 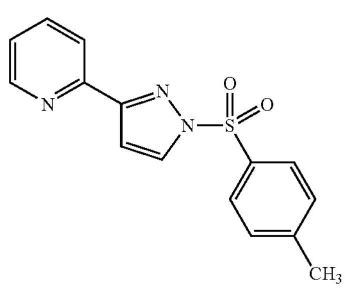 | 8.68 (d, 1H), 8.63 (s, 1H), 8.04 (m, 3H), 7.90 (t, 1H), 7.49 (d, 2H), 7.42 (t, 1H), 7.19 (s, 1H), 2.38 (s, 3H) | MS 299.65 (M⁺ + H). |

Other variations or modifications, which will be obvious to those skilled in the art, are within the scope and teachings of this invention. This invention is not to be limited except as set forth in the following claims.

What is claimed is:

1. A compound which is selected from the group consisting of:

3-(4-pyridin-2-yl-1H-pyrazol-1-yl)benzonitrile;
2-[1-(3-fluorophenyl)-1H-pyrazol-4-yl]pyridine;
3-(1-pyridin-2-yl-1H-pyrazol-4-yl)benzonitrile;
2-[4-(3-methoxyphenyl)-1H-pyrazol-1-yl]pyridine;
3-(3-pyridin-2-yl-1H-pyrazol-1-yl)benzonitrile;
3-(1-pyridin-2-yl-1H-pyrazol-3-yl)benzonitrile;
2-[1-(3-bromophenyl)-1H-pyrazol-4-yl]pyridine;
3-fluoro-5-(3-pyridin-2-yl-1H-pyrazol-1-yl)benzonitrile;
3-fluoro-5-(5-methyl-3-pyridin-2-yl-1H-pyrazol-1-yl)benzonitrile;
2-[1-(2,5-difluorophenyl)-1H-pyrazol-3-yl]pyridine;
3-(3,5-dimethyl-4-pyridin-2-yl-1H-pyrazol-1-yl)benzonitrile;
2-[1-(2,3,5,6-tetrafluoro-phenyl)-1H-pyrazol-3-yl]pyridine;
2-[1-(3,5-difluoro-phenyl)-1H-pyrazol-3-yl]-pyridine;
2-(1-pentafluorophenyl-1H-pyrazol-3-yl)-pyridine;
2-[1-(4-methoxy-phenyl)-1H-pyrazol-3-yl]-pyridine;
2-[1-(2,3,5,6-tetrafluoro-4-methyl-phenyl)-1H-pyrazol-3-yl]-pyridine;
2-[1-(3-nitro-phenyl)-1H-pyrazol-3-yl]-pyridine;
3-fluoro-5-(4-pyridin-2-yl-1H-pyrazol-1-yl)benzonitrile;
2-{1-[3-fluoro-5-(pyridin-3-yloxy)phenyl]-1H-pyrazol-4-yl}pyridine;
4-(4-pyridin-2-yl-1H-pyrazol-1-yl)pyridine-2-carbonitrile;
2-[1-(4-nitro-phenyl)-1H-pyrazol-3-yl]-pyridine;
3-(1-pyridin-2-yl-1H-pyrazol-3-yl)benzonitrile;
2-[4-(3-methylphenyl)-1H-pyrazol-1-yl]pyridine;
2-[1-(3-fluoro-phenyl)-1H-pyrazol-4-yl]-pyridine;
2-[1-(3,4-dimethyl-phenyl)-1H-pyrazol-4-yl]-pyridine;
2-[1-(4-phenoxy-phenyl)-1H-pyrazol-4-yl]-pyridine;
2-[1-(3-methoxy-phenyl)-1H-pyrazol-4-yl]-pyridine;
2-[1-(2-benzyl-phenyl)-1H-pyrazol-4-yl]-pyridine;
2-[1-(4-isopropoxy-phenyl)-1H-pyrazol-4-yl]-pyridine;
2-[1-(3-ethyl-phenyl)-1H-pyrazol-4-yl]-pyridine;
2-[1-(3-trifluoromethoxy-phenyl)-1H-pyrazol-4-yl]-pyridine;
2-[1-(2-fluoro-5-trifluoromethyl-phenyl)-1H-pyrazol-4-yl]-pyridine;
2-[1-(3-tert-butyl-phenyl)-1H-pyrazol-4-yl]-pyridine;
2-[1-(2,3,5-trifluorophenyl)-1H-pyrazol-3-yl]pyridine;
3-(3-pyridin-2-yl-1H-pyrazol-1-yl)-5-(trifluoromethyl)benzonitrile;
3-[(5-chloropyridin-3-yl)oxy]-5-(3-pyridin-2-yl-1H-pyrazol-1-yl)benzonitrile;
2-(3-pyridin-2-yl-1H-pyrazol-1-yl)isonicotinonitrile;
2-[1-(3,5-dibromophenyl)-1H-pyrazol-3-yl]pyridine;
3-bromo-5-(3-pyridin-2-yl-1H-pyrazol-1-yl)benzonitrile;
2-{4-[3-fluoro-5-(pyridin-3-yloxy)phenyl]-1H-pyrazol-1-yl}pyridine;
2-[1-(3-bromo-5-fluorophenyl)-1H-pyrazol-3-yl]pyridine;
3-[(3-pyridin-2-yl-1H-pyrazol-1-yl)methyl]benzonitrile;
2-[1-(2,4-difluorophenyl)-1H-pyrazol-3-yl]pyridine;
4-[(4-pyridin-2-yl-1H-pyrazol-1-yl)methyl]benzonitrile;
3-[(4-pyridin-2-yl-1H-pyrazol-1-yl)methyl]benzonitrile;
6-(4-pyridin-2-yl-1H-pyrazol-1-yl)nicotinonitrile;
2-[(4-pyridin-2-yl-1H-pyrazol-1-yl)methyl]benzonitrile;
2-[1-(3,5-bis-trifluoromethyl-phenyl)-1H-pyrazol-3-yl]-pyridine;
2-[4-(4-fluorophenyl)-1H-pyrazol-1-yl]pyridine;
4-(1-pyridin-2-yl-1H-pyrazol-4-yl)benzonitrile;
2-{4-[3-(trifluoromethyl)phenyl]-1H-pyrazol-1-yl}pyridine;
2-{4-[4-(trifluoromethyl)phenyl]-1H-pyrazol-1-yl}pyridine;
2-[4-(3-fluorophenyl)-1H-pyrazol-1-yl]pyridine;
2-[1-(3-bromo-4-methylphenyl)-1H-pyrazol-4-yl]pyridine;
2-[1-(4-bromo-3-methyl-phenyl)-1H-pyrazol-4-yl]-pyridine;
2-[1-(4-sec-butyl-phenyl)-1H-pyrazol-4-yl]-pyridine;
2-[1-(4-propyl-phenyl)-1H-pyrazol-4-yl]-pyridine;
2-[1-(4-cyclohexyl-phenyl)-1H-pyrazol-4-yl]-pyridine;
2,2-dimethyl-propionic acid 4-(4-pyridin-2-yl-pyrazol-1-yl)-phenyl ester;
2,2-dimethyl-propionic acid 4-(4-pyrimidin-4-yl-pyrazol-1-yl)-phenyl ester;
2-[1-(2-propyl-phenyl)-1H-pyrazol-4-yl]-pyridine;
dimethyl-carbamic acid 4-(4-pyridin-2-yl-pyrazol-1-yl)-phenyl ester;
2-[1-(2,6-dimethyl-phenyl)-1H-pyrazol-4-yl]-pyridine;
2-[1-(2-fluoro-4-methyl-phenyl)-1H-pyrazol-4-yl]-pyridine;
2-[1-(3-bromo-2-methyl-phenyl)-1H-pyrazol-4-yl]-pyridine;
4-(3-pyridin-2-yl-1H-pyrazol-1-yl)benzoic acid;
2-{1-[3-(pyridin-4-yloxy)phenyl]-1H-pyrazol-3-yl}pyridine;
2-(3-pyridin-2-yl-1H-pyrazol-1-yl)-5-(trifluoromethyl)pyridine;
2-(1-phenyl-1H-pyrazol-3-yl)pyridine;
3-(3-pyridin-2-yl-1H-pyrazol-1-yl)benzoic acid;
2-{1-[3-fluoro-5-(pyridin-4-ylthio)phenyl]-1H-pyrazol-3-yl}pyridine; and
2-{1-[(4-methylphenyl)sulfonyl]-1H-pyrazol-3-yl}pyridine;

or a pharmaceutically acceptable salt thereof.

2. A pharmaceutical composition which comprises the compound of claim 1, or a pharmaceutically acceptable salt thereof, and a pharmaceutically acceptable carrier.

* * * * *